US012594244B2

(12) United States Patent
Collman et al.

(10) Patent No.: US 12,594,244 B2
(45) Date of Patent: *Apr. 7, 2026

(54) THERAPEUTIC COMPOSITIONS FOR TREATMENT OF HUMAN IMMUNODEFICIENCY VIRUS

(71) Applicant: Gilead Sciences, Inc., Foster City, CA (US)

(72) Inventors: Benjamin Micah Collman, San Mateo, CA (US); Lei Hong, Cupertino, CA (US); Joanna M. Koziara, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/343,371

(22) Filed: Sep. 29, 2025

(65) Prior Publication Data

US 2026/0027061 A1 Jan. 29, 2026

Related U.S. Application Data

(63) Continuation of application No. 19/207,799, filed on May 14, 2025, which is a continuation of application No. 18/909,687, filed on Oct. 8, 2024, now abandoned, which is a continuation of application No. 18/587,695, filed on Feb. 26, 2024, now abandoned, which is a continuation of application No. 18/349,859, filed on Jul. 10, 2023, now abandoned, which is a continuation of application No. 17/738,803, filed on May 6, 2022, now Pat. No. 11,744,802, which is a continuation of application No. 16/987,081, filed on Aug. 6, 2020, now abandoned, which is a continuation of application No. 16/713,380, filed on Dec. 13, 2019, now abandoned, which is a continuation of application No. 15/346,335, filed on Nov. 8, 2016, now Pat. No. 10,548,846.

(60) Provisional application No. 62/399,999, filed on Sep. 26, 2016, provisional application No. 62/253,042, filed on Nov. 9, 2015.

(51) Int. Cl.

| | |
|---|---|
| ***A61K 31/5365*** | (2006.01) |
| ***A61K 9/00*** | (2006.01) |
| ***A61K 9/20*** | (2006.01) |
| ***A61K 9/24*** | (2006.01) |
| ***A61K 9/28*** | (2006.01) |
| ***A61K 31/513*** | (2006.01) |
| ***A61K 31/537*** | (2006.01) |
| ***A61K 31/553*** | (2006.01) |
| ***A61K 31/675*** | (2006.01) |
| ***A61P 31/18*** | (2006.01) |

(52) U.S. Cl.

CPC ............ *A61K 9/209* (2013.01); *A61K 9/0053* (2013.01); *A61K 9/2013* (2013.01); *A61K 9/2027* (2013.01); *A61K 9/2054* (2013.01); *A61K 9/2086* (2013.01); *A61K 9/2095* (2013.01); *A61K 9/28* (2013.01); *A61K 9/2833* (2013.01); *A61K 31/513* (2013.01); *A61K 31/5365* (2013.01); *A61K 31/537* (2013.01); *A61K 31/553* (2013.01); *A61K 31/675* (2013.01); *A61P 31/18* (2018.01)

(58) Field of Classification Search

CPC .... A61K 9/209; A61K 9/0053; A61K 9/2013; A61K 9/2027; A61K 9/2054; A61K 9/2086; A61K 9/2095; A61K 9/28; A61K 9/2833; A61K 31/513; A61K 31/5365; A61K 31/537; A61K 31/553; A61K 31/675; A61P 31/18

See application file for complete search history.

(56) References Cited

U.S. PATENT DOCUMENTS

| | | | |
|---|---|---|---|
| 7,390,791 | B2 | 6/2008 | Becker et al. |
| 7,803,788 | B2 | 9/2010 | Becker et al. |
| 8,592,397 | B2 | 11/2013 | Dahl et al. |
| 8,598,185 | B2 | 12/2013 | Dahl et al. |
| 8,716,264 | B2 | 5/2014 | Dahl et al. |
| 8,754,065 | B2 | 6/2014 | Liu et al. |
| 8,841,310 | B2 | 9/2014 | Stoffels |
| 9,018,192 | B2 | 4/2015 | Dahl et al. |
| 9,216,996 | B2 | 12/2015 | Jin et al. |
| 9,296,769 | B2 | 3/2016 | Liu et al. |
| 9,457,036 | B2 | 10/2016 | Dahl et al. |
| 9,545,414 | B2 | 1/2017 | Dahl et al. |
| 9,663,528 | B2 | 5/2017 | Desai et al. |
| 9,682,084 | B2 | 6/2017 | Carra et al. |
| 9,708,342 | B2 | 7/2017 | Carra et al. |
| 9,732,092 | B2 | 8/2017 | Jin et al. |

(Continued)

FOREIGN PATENT DOCUMENTS

| | | |
|---|---|---|
| WO | WO-2004024078 A2 | 3/2004 |
| WO | WO-2006030807 A1 | 3/2006 |

(Continued)

OTHER PUBLICATIONS

Ahmed, N. et al. (2015) "BHIVA Guidelines for the Treatment of HIV-1-Positive Adults With Antiretroviral Therapy 2015" British HIV Association 1-5.

(Continued)

*Primary Examiner* — Jessica Worsham

(57) ABSTRACT

A solid oral dosage form is provided, comprising a compound of Formula I or a pharmaceutically acceptable salt thereof, tenofovir alafenamide or a pharmaceutically acceptable salt thereof, and emtricitabine or a pharmaceutically acceptable salt thereof.

29 Claims, 6 Drawing Sheets

(56) References Cited

U.S. PATENT DOCUMENTS

| | | | |
|---|---|---|---|
| 10,035,809 | B2 | 7/2018 | Bacon et al. |
| 10,098,886 | B2 | 10/2018 | Carra et al. |
| 10,385,067 | B2 | 8/2019 | Carra et al. |
| 10,548,846 | B2 | 2/2020 | Collman et al. |
| 11,744,802 | B2 | 9/2023 | Collman et al. |
| 2002/0119443 | A1 | 8/2002 | Becker et al. |
| 2003/0219727 | A1 | 11/2003 | Becker et al. |
| 2005/0124583 | A1 | 6/2005 | Becker et al. |
| 2005/0124584 | A1 | 6/2005 | Becker et al. |
| 2005/0124585 | A1 | 6/2005 | Becker et al. |
| 2006/0024659 | A1 | 2/2006 | Becker et al. |
| 2007/0099902 | A1 | 5/2007 | Dahl et al. |
| 2007/0219243 | A1 | 9/2007 | Kearney et al. |
| 2008/0200435 | A1 | 8/2008 | Stoffels |
| 2010/0285122 | A1 | 11/2010 | Oliyai et al. |
| 2013/0243857 | A1 | 9/2013 | Oliyai et al. |
| 2014/0142070 | A1 | 5/2014 | Delaet et al. |
| 2014/0213556 | A1 | 7/2014 | Dahl et al. |
| 2014/0221355 | A1 | 8/2014 | Lazerwith et al. |
| 2014/0349971 | A1 | 11/2014 | Stoffels |
| 2015/0018359 | A1 | 1/2015 | Desai et al. |
| 2015/0111856 | A1 | 4/2015 | Dahl et al. |
| 2015/0150810 | A1 | 6/2015 | Oliyai et al. |
| 2015/0283135 | A1 | 10/2015 | Stoffels |
| 2016/0016973 | A1 | 1/2016 | Carra et al. |
| 2016/0194335 | A1 | 7/2016 | Jin et al. |
| 2017/0000807 | A1 | 1/2017 | Koziara et al. |
| 2017/0027967 | A1 | 2/2017 | Koziara et al. |
| 2017/0079999 | A1 | 3/2017 | Dahl et al. |
| 2017/0114074 | A1 | 4/2017 | Jin et al. |
| 2017/0189337 | A1 | 7/2017 | Collman et al. |
| 2017/0197985 | A1 | 7/2017 | Carra et al. |
| 2018/0022757 | A1 | 1/2018 | Chiu et al. |
| 2018/0065986 | A1 | 3/2018 | Carra et al. |
| 2018/0215769 | A1 | 8/2018 | Jin et al. |
| 2019/0015420 | A1 | 1/2019 | Carra et al. |
| 2021/0052502 | A1 | 2/2021 | Collman et al. |

FOREIGN PATENT DOCUMENTS

| | | | |
|---|---|---|---|
| WO | WO-2006116764 | A1 | 11/2006 |
| WO | WO-2008/043829 | A2 | 4/2008 |
| WO | WO-2013/115916 | A1 | 8/2013 |
| WO | WO-2013/116720 | A1 | 8/2013 |
| WO | WO-2014/100323 | A1 | 6/2014 |
| WO | WO-2015/022351 | A1 | 2/2015 |
| WO | WO-2015/039348 | A1 | 3/2015 |
| WO | WO-2015/196116 | A1 | 12/2015 |
| WO | WO-2015/196137 | A1 | 12/2015 |
| WO | WO-2017/004012 | A1 | 1/2017 |
| WO | WO-2017/083304 | A1 | 5/2017 |
| WO | WO-2020/091197 | A1 | 5/2020 |

OTHER PUBLICATIONS

Aulton, M.E. (1988) "Tablets and Compaction" Pharmaceutics: The Science of Dosage Form Design 27(2):410-412.

British Medical Association and Royal Pharmaceutical Society of Great Britain (2016) "British National Formulary" 557-566.

Business Wire (2015) "European Medicines Agency Validates Gilead's Marketing Application for Fixed-Dose Combination of Emtricitabine and Tenofovir Alafenamide for HIV Treatment" 1-2.

Business Wire (2015) Gilead Submits New Drug Application to U.S. Food and Drug Administration for Single Tablet Regimen for HIV Containing Rilpivirine, Emtricitabine and Tenofovir Alafenamide (R/F/TAF) 1-3.

Business Wire (2016) "U.S. Food and Drug Administration Approves Descovy (Emtricitabine, Tenofovir Alafenamide), Gilead's Third TAF-Based HIV Therapy" 1-4.

Clayden, P. et al. (2015) "HIV, Hepatitis C Virus (HCV), And Tuberculosis (TB) Drugs, Diagnostics, Vaccines, Preventive Technologies, Research Toward a Cure, and Immune-Based and Gene Therapies in Development" 2015 Pipeline Report 1-183.

EMA Viread Authorization (2017) "Product Details" European Medicines Agency.

Eron, Joe et al. (2016) "Retesting of suspected low-level HIV-1 viral load blips: A new paradigm to prevent extra clinic visits and unnecessary patient anxiety" Abstract, Oct. 28, 2016 New Orleans.

EU Clinical Trials Reigster (2020) "A Phase 3, Randomized, Double-Blind Study to Evaluate the Safety and Efficacy of GS-9883/Emtricitabine/Tenofovir Alafenamide Versus Dolutegravir + Emtricitabine/Tenofovir Alafenamide in HIV-1 Infected, Antiretroviral Treatment-Naive Adults".

Examination Report dated Aug. 15, 2018 for New Zealand Appl. No. 741957.

Examination Report dated Nov. 5, 2019 for Australian Appl. No. 2016354007.

Extended European Search Report dated Mar. 11, 2020 for European Appl. No. 19186760.5.

Gallant Joel et al. (2016) Abstract "Novel INSTI GS-9883 10 Day Monotherapy in HIV-1 Infected Subjects" ASM2016.

Gallant, Joel et al. (2016) "Novel Integrase Strand Transfer Inhibitor Bictegravir 10 Day Monotherapy in HIV-1-Infected Patients" ASM-Microbe2016.

Jeraj, Z. (2020) "Experimental Report" 1-5.

Johnson, L. (2015) "Gilead's New Four-in-One HIV Pill, Genvoya, Wins US Approval" Medical Xpress.

Jones, Gregg et al. (2016) Poster #413 "Bictegravir (GS-9883), a Novel HIV-1 Integrase Strand Transfer Inhibitor (INSTI) with Optimized In Vitro Resistance Profile".

Kulkarni, R. et al. (2014) "The Combined Anti-HIV-1 Activies of Emtricitabine and Tenofovir plus the Integrase Inhibitor Elvitegravir or Raltegravir Show High Levels of Synergy In Vitro" Antimicrobial Agents and Chemotherapy 58(10):6145-6150.

Lazerwith, Scott E. (2016) Poster #414 "Discovery of Bictegravir (GS-9883), a Novel, Unboosted, Once-Daily HIV-1 Integrase Strand Transfer Inhibitor (INSTI) with Improved Pharmacokinetics and In Vitro Resistance Profile".

Lazerwith, Scott E. et al. Abstract "Discovery of GS-9883, an HIV-1 Integrase Strand Transfer Inhibitor (INSTI) with Improved Pharmacokinetics and In Vitro Resistance Profile".

Moss et al. (2012) Divalent metals and pH alter raltegravir disposition in vitro. American Society for Microbiology doi:10.1128/AAC.06407-11.

Notice of Final Rejection dated Mar. 19, 2020 for Korean Appl. No. 10-2018-7015929.

Notice of Opposition dated May 27, 2020 for European Patent No. 3346995 (Dr. Richard Cooke).

Notice of Opposition dated May 27, 2020 for European Patent No. 3346995 (Teva Pharmaceutical Industries Ltd.).

Notice of Opposition dated May 28, 2020 for European Patent No. 3346995 (Sandoz GmbH).

Notice of Preliminary Rejection dated Sep. 4, 2019 for Korean Appl. No. 10-2018-7015929.

ODEFSEY Approval Package (2016) "Center for Drug Evaluation and Research".

Office Action dated Sep. 18, 2018 for Bolivian Appl. No. SP260-2016.

Office Action dated Oct. 3, 2018 for Panamanian Appl. No. 92163.

Office Action dated Nov. 13, 2018 for Pakistani Appl. No. 696/2016.

Office Action dated Jan. 21, 2019 for European Appl. No. 16798063.0.

Office Action dated Mar. 25, 2019 for Bolivian Appl. No. SP260-2016.

Office Action dated Sep. 22, 2019 for Gulf Cooperation Council Appl. No. 2016-32320.

Office Action dated Mar. 27, 2020 for Chinese Appl. No. 201680065167.3.

Office Action for El Salvadorian Appl. No. 2018005682.

Office Action for Eurasian Appl. No. 201890654.

Opposition dated Jun. 20, 2017 for Colombian Appl. No. 15-265.717.

Park, T. et al. (2015) "Review of Integrase Strand Transfer Inhibitors for the Treatment of Human Immunodeficiency Virus Infection" Expert Rev. Anti Infect. Ther. 13(10):1195-1212.

(56) References Cited

OTHER PUBLICATIONS

Patel, Parul et al. (2014) "Relative bioavailability of a paediatric granule formulation of the HIV intergrase inhibitor dolutegravir in healthy adult subjects." Antiviral Therapy (19):229-233.
Patrick, M. (2015) "Analyzing Gilead Sciences' Research and Development in 3Q15" Market Realist 1-2.
Sax, P. et al. (2014) "Tenofovir Alafenamide Vs. Tenofovir Disoproxil Fumarate in Single Tablet Regimens for Initial HIV-1 Therapy: A Randomized Phase 2 Study" J Acquir Immune Defic Syndr 67(1):52-58.
Sax, Paul E. (2016) "Randomized Trial of Bictegravir or Dolutegravir with FTC/TAF for Initial HIV Therapy" CROI BIC Sep. 8, 2016.
Search Report—Intl Search Report—Written Opinion dated Jan. 24, 2007 for PCT/US2016/060989.
Shah, B. et al. (2014) "Dolutegravir: A new Integrase Strand Transfer Inhibitor for the Treatment of HIV" Pharmacotherapy 34(5):506-520.
Shende, P. et al. (2012) "Multi-layer Tablet: Current Scenario and Recent Advances" International Journal of Drug Delivery 4(4):418-426.
Thomson Reuters Drug News (2011) "Gilead and Tibotec finalize agreement on single-tablet HIV regimen" http://drugnews.thomson-pharma.com/ddn/article.do?id=113441&source=CompanyCommunication§ion=AIDS#.
TIVICAY Product Label (Revised Sep. 2018) GlaxoSmithKline, 44 Pages.
TRIUMEQ Product Label (Revised Nov. 2017) GlaxoSmithKline, 48 Pages.
Tsiang, M. et al. "Antiviral Activity of GS-9883, a Potent Next Generation HIV-1 Integrase Strand Transfer Inhibitor" (ASM-Microbe20161).
Tsiang, M. et al. "GS-9883, a Novel HIV-1 Integrase Strand Transfer Inhibitor (INSTI) with Optimized In Vitro Resistance Profile" (ASMMicrobe20162).
Tsiang, M. et al. (2016) Poster #416 "Antiviral Activity of Bictegravir (GS-9883), a Potent Next Generation HIV-1 Integrase Strand Transfer Inhibitor".
U.S. National Library of Medicine (2019) "Safety and Efficacy of Switching to a FDC of GS-9883/F/TAF From E/C/F/TAF, E/C/F/TDF, or ATV+RTV+FTC/TDF in Virologically Supressed HIV-1 Infected Women" ClinicalTrials.gov. 1-8.
USAN (2016) "Statement on a Nonproprietary Name Adopted by the USAN Council".
Viread Draft Labeling (2001) Center for Drug Evaluation and Research 1-26.
White, Kristen et al. (2016) "Potent Activity of Bictegravir (BIC; GS-9883), a Novel Unboosted; HIV-1 Integrase Strand Transfer Inhibitor (INSTI), Against Patient Isolates; with INSTI-Resistance" EU Workshop HIV Hepatitis.
White, Kristen et al. (2016) Poster "The Integrase Strand Transfer Inhibitor Bictegravir has; a Long Integrase/DNA Dissociation Half-life".
White, Kristen et al. (2016) The Integrase Strand Transfer Inhibitor Bictegravir has a Long Integrase/DNA Dissociation Half-life.
White, Kritsten et al. (2017) "Bictegravir Dissociation Half-life from HIV-1 G140S+Q148H Integrase/DNA Complexes " CROI BIC.
World Health Organization (2007) "Guidance on the Establishment of New INN Stems" 1-2.
World Health Organization (2013) "The Use of Stems in the Selection of International Nonproprietary Names (INN) for Pharmaceutical Substances" 1-192.
World Health Organization Drug Information (2015) "International Nonproprietary Names for Pharmacuetical Substances (INN)" 29(2):1-107.
Yoshinaga, T. et al. (2015) "Antivrial Characteristics of GSK1265744, an HIV Integrase Inhibitor Dosed Orally or by Long-Acting Injection" Antimicrobial Agents and Chemotherapy 59(1):397-406.
Zhang et al. (2017) "Clinical Pharmacology of the HIV Integrase Strand Transfer Inhibitor Bictegravir" CROI BIC Sep. 26, 2016.
ClinicalTrials.gov Archive. (2014) "A Phase 1b Randomized, Double-Blinded, Sequential Cohort Placebo-Controlled Study of the Safety, Pharmacokinetics, and Antiviral Activity of GS-9883 in HIV-1 Infected Subjects", https://clinicaltrials.gov/archive/NCT02275065/2014_10_26, 3 pages.
European Medicines Agency, Committee for Medicinal Products for Human Use. (2018) "Assessment report—Biktarvy", 104 pages.
ClinicalTrials.gov Archive. (2015) "A Phase 2, Randomized, Double-Blinded Study of the Safety and Efficacy of GS-9883 + Emtricitabine/Tenofovir Alafenamide Versus Dolutegravir + Emtricitabine/Tenofovir Alafenamide in HIV-1 Infected, Antiretroviral Treatment-Naive Adults", https://clinicaltrials.gov/archive/NCT02397694/2015_03_24, 4 pages.
Exam Report dated Jul 26, 2019 for Indian Appl. No. 201817013772.
Examination Report dated Mar. 24, 2021 for Australian Appl. No. 2020200995, 5 pages.
Kommavaparu, P. et al. (2015) "Preparation and characterization of rilpivirine solid dispersions with the application of enhanced solubility and dissolution rate", Beni-Suef University Journal of Basic and Applied Sciences 4, pp. 71-79.
European Medicines Agency, Committee for Medicinal Products for Human Use. (2015) "Assessment report—Genvoya", extract, pp. 1-20.
ZIGA. (2021) Experimental Report, Sandoz GmbH, 8 pages.
Smith, S. et al. (2018) "Efficacies of Cabotegravir and Bictegravir against drug-resistant HIV-1 integrase mutant", Retrovirology 15(37), 18 pages.
Acosta, R. et al. (2021) "In Vitro Forgiveness of Oral and Long-Acting INSTI-Containing Regiments at Drug Concentrations Simulating Variable Adherence", 18th European AIDS Conference, 1 page.
Lozano, A. et al. (2020) "Failure to bictegravir and development of resistance mutations in an antiretroviral-experienced patient", Antiviral Research 179, 104717, pp. 1-4.
Chamberlain N. et al. (2021) "Case Report: Emergent Resistance in a Treatment-Naïve Person With Human Immunodeficiency Virus Under Bictegravir-Based Therapy", Open Forum Infectious Diseases, pp. 1-3.
Song I. et al. (2009) Poster—Pharmacokinetic (PK) and Pharmacodynamic (PD) Relationship of S/GSK1349572, a Next Generation Integrase Inhibitor (INI), in HIV-1 Infected Patients, 5th International AIDS (IAS) Conference on HIV Pathogenesis, Treatment and Prevention, 1 page.
ERON. (2009) Report—New Drugs, New strategies, 5th International AIDS (IAS) Conference on HIV Pathogenesis, Treatment and Prevention, 5 pages.
Notice of Preliminary Rejection dated Dec. 23, 2021 for Korean Appl. No. 10-2020-7025458, 7 pages.
Office Action dated May 24, 2022 for Taiwanese Appl. No. 110129951, 23 pages.
Office Action dated Aug. 18, 2022 for Korean Appl. No. 10-2020-7025458, 7 pages.
Office Action and Search Report dated Jul. 27, 2022 for Chinese Appl. No. 202110669391.6, 18 pages.
Examination Report dated Nov. 23, 2022 for Canadian Appl. No. 2948021, 5 pages.
Office Action dated Jan. 31, 2023 for Korean Appl. No. 10-2020-7025458, 5 pages.
Notice of Preliminary Rejection dated Mar. 23, 2023 for Korean Appl. No. 10-2023-7001933, 6 pages.
Patentee's Response to Oppositions dated Jan. 11, 2021 for European Patent No. EP3346995, 24 pages.
Brief Communication and Further Submissions from Opponent Dr. Richard Cooke dated Mar. 9, 2021 for European Patent No. EP3346995, 6 pages.
Brief Communication and Further Submissions from Opponent Sandoz GmbH dated Mar. 24, 2021 for European Patent No. EP3346995, 12 pages.
Brief Communication and Further Submissions from Opponent Teva Pharmaceutical Industries Ltd. dated Mar. 26, 2021 for European Patent No. EP3346995, 10 pages.
Summons to Attend Oral Proceedings and Preliminary Opinion dated Jun. 24, 2021 for European Patent No. EP3346995, 19 pages.

(56) References Cited

OTHER PUBLICATIONS

Further Submissions from Opponent Sandoz GmbH dated Dec. 23, 2021 for European Patent No. EP3346995, 6 pages.
Patentee's Response to Summons and Preliminary Opinion dated Jan. 24, 2022 for European Patent No. EP3346995, 12 pages.
Summons to Attend Oral Proceedings dated Apr. 5, 2022 for European Patent No. EP3346995, 18 pages.
Further Submissions and Response to Preliminary Opinion from Opponent Teva Pharmaceutical Industries Ltd. dated Aug. 25, 2022 for European Patent No. EP3346995, 10 pages.
Further Submissions from Opponent Dr. Richard Cooke dated Aug. 26, 2022 for European Patent No. EP3346995, 6 pages.
Further Submissions from Opponent Sandoz GmbH dated Aug. 26, 2022 for European Patent No. EP3346995, 3 pages.
Patentee's Response to Summons and Written Submissions dated Aug. 26, 2022 for European Patent No. EP3346995, 5 pages.
Interlocutory Decision and Minutes of the Oral Proceedings dated Dec. 23, 2022 for European Patent No. EP3346995, 101 pages.
JAVOR. (2023) Experimental Report, Novartis, 4 pages.
Therapeutic Goods Administration. (2017) Australian Public Assessment Report for emtricitabine / rilpivirine / tenofovir / alafenamide fumarate—Proprietary Product Name: Odefsey, 44 pages.
Song, I. et al. (2012) "Effect of Food on the Pharmacokinetics of the Integrase Inhibitor Dolutegravir" Antimicrobial Agents and Chemotherapy 56(3):1627-1629.
Grounds of Appeal from Opponent Teva Pharmaceutical Industries Ltd. dated Apr. 25, 2023 for European Patent No. EP3346995, 28 pages.
Grounds of Appeal from Opponent Dr. Richard Cooke dated May 2, 2023 for European Patent No. EP3346995, 1 1 pages.
Grounds of Appeal from Opponent Sandoz GmbH dated Apr. 28, 2023 for European Patent No. EP3346995, 15 pages.
Reply to Patentee from Opponent Dr. Richard Cooke dated May 22, 2023 for European Patent No. EP3346995, 6 pages.
Patentee's Grounds of Appeal dated May 2, 2023 for European Patent No. EP3346995, 3 pages.
Reply to Patentee from Opponent Teva Pharmaceutical Industries Ltd dated Aug. 8, 2023 for European Patent No. EP3346995, 4 pages.
Reply to Patentee from Opponent Sandoz GmbH dated Sep. 8, 2023 for European Patent No. EP3346995, 4 pages.
Patentee's Reply to Opponents' Grounds of Appeal dated Sep. 18, 2023 for European Patent No. EP3346995, 92 pages.
Rejoinder (Response to Patentee Reply to Grounds of Appeal) from Opponent Teva Pharmaceutical Industries Ltd dated Dec. 27, 2023 for European Patent No. EP3346995, 7 pages.
Patentee's Reply to Rejoinder dated Mar. 12, 2024 for European Patent No. EP3346995, 6 pages.
Summons to Attend Oral Proceedings dated Apr. 24, 2024 for European Patent No. EP3346995, 2 pages.
Board of Appeals Preliminary Opinion dated Dec. 3, 2024 for European Patent No. EP3346995, 14 pages.
Patentee's Reply to Preliminary Opinion dated Jan. 30, 2025 for European Patent No. EP3346995, 3 pages.
Minutes of the Oral Proceedings dated Mar. 13, 2025 for European Patent No. EP3346995, 4 pages.
Decision of Technical Board of Appeal dated May 26, 2025 for European Patent No. EP3346995, 30 pages.
European Medicines Agency. (2003) ICH Topic Q1A (R2), "Note for Guidance on Stability Testing: Stability Testing of New Drug Substances and Products", 20 pages.
Shuter. (2008) "Forgiveness of non-adherence to HIV-1 antiretroviral therapy", Journal of Antimicrobial Chemotherapy 61:769-773.
European Medicines Agency. (2014) Extract of the EPAR for Triumeq®, 2 pages.
European Medicines Agency. (2007) Extract of the EPAR for Celsentri®, 3 pages.
Daneshmend et al. (1984) "Influence of food on the pharmacokinetics of ketoconazole", Antimicrobial Agents and Chemotherapy 25(1):1-3.
Wills. (1984) "Influence of food on the bioavailability of trimoprostil: an overview", Journal of Clinical Pharmacology 24:194-201.
Scallion et al. (2009) "Effects of food intake on the pharmacokinetics of diclofenac potassium soft gelatin capsules: a single-dose, randomized, two-way crossover study", Clinical Therapeutics 31(10):2233-2241.

THERAPEUTIC COMPOSITIONS FOR TREATMENT OF HUMAN IMMUNODEFICIENCY VIRUS

CROSS-REFERENCE TO THE RELATED APPLICATIONS

This patent application is a Continuation of U.S. application Ser. No. 19/207,799 filed on May 14, 2025, which is a Continuation of U.S. application Ser. No. 18/909,687, filed on Oct. 8, 2024, which is a Continuation of U.S. application Ser. No. 18/587,695, filed Feb. 26, 2024, which is a Continuation of U.S. application Ser. No. 18/349,859, filed Jul. 10, 2023, which is a Continuation of Ser. No. 17/738,803, filed May 6, 2022, issued as U.S. Pat. No. 11,744,802, which is a Continuation of U.S. application Ser. No. 16/987,081, filed Aug. 6, 2020, which is a Continuation of U.S. application Ser. No. 16/713,380, filed Dec. 13, 2019, which is a Continuation of U.S. application Ser. No. 15/346,335, filed Nov. 8, 2016, issued as U.S. Pat. No. 10,548,846, which claims priority to U.S. Application Ser. No. 62/253,042, filed Nov. 9, 2015 and of U.S. application Ser. No. 62/399,999, filed Sep. 26, 2016. The contents of each of these applications are hereby incorporated herein in their entirety.

TECHNICAL FIELD

Pharmaceutical formulations suitable for treating viral infections such as HIV are provided, in particular solid oral dosage forms including the compound of Formula I, emtricitabine and tenofovir alafenamide.

BACKGROUND

Human immunodeficiency virus, type 1 (HIV-1) infection is a life-threatening and serious disease of major public health significance, with approximately 35 million people infected worldwide (Joint United Nations Programme on HIV/AIDS (UNAIDS). Global report: UNAIDS report on the global AIDS epidemic, 2013). Standard of care for the treatment of HIV-1 infection uses combination antiretroviral therapy (ART) to suppress viral replication to below detectable limits, increase CD4 cell counts, and halt disease progression.

There is also a need for medications to serve populations with limited treatment options (e.g., children, women, and the elderly). In certain situations, these populations may have difficulty maintaining treatment because of pill burden (number of pills to take each day, as well as different combinations of pills) or the size of the pills themselves, once they are coformulated into a multidrug composition. For example, there is currently no fixed dose combination registered for once a day dosing (i.e. QD) for very young children (e.g., younger than age 12 years).

A goal of antiretroviral therapy is to achieve viral suppression in the HIV infected patient. Treatment guidelines published by the United States Department of Health and Human Services provide that achievement of viral suppression requires the use of combination therapies, i.e. several drugs from at least two or more drug classes. In addition, decisions regarding the treatment of HIV infected patients are complicated when the patient requires treatment for other medical conditions (e.g., metformin, rifampin, HCV antivirals, hormonal contraceptives, etc.). Because the standard of care requires the use of multiple different drugs to suppress HIV, as well as to treat other conditions the patient may be experiencing, the potential for drug-drug interaction is a criterion for selection of a drug regimen. As such, there is a need for antiretroviral therapies having a decreased potential for drug-drug interactions (e.g., those that affect transporters (e.g., OCT-2) or activate receptors (e.g., PXR).

SUMMARY

All the compositions and oral dosage forms herein include a compound of Formula I, (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide, having the following structure:

(I)

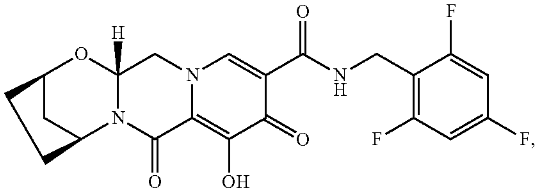

or a pharmaceutically acceptable salt thereof.

In certain embodiments, the pharmaceutically acceptable salt of the compound of Formula I is a compound of Formula II, sodium (2R,5S,13aR)-7,9-dioxo-10-((2,4,6-trifluorobenzyl) carbamoyl)-2,3,4,5,7,9,13,13a-octahydro-2,5-methanopyrido[1',2':4,5]pyrazino[2,1-b][1,3]oxazepin-8-olate, having the following structure:

(II)

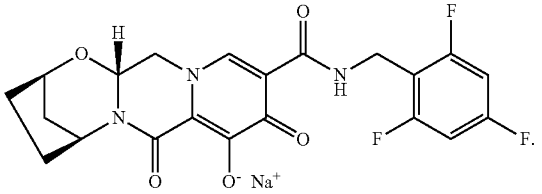

The inventors have successfully formulated an oral dosage form containing the compound of Formula I, tenofovir alafenamide and emtricitabine. This oral dosage form is suitable for use in medicine, and in particular in treating viral infections such as HIV.

In one aspect, a solid oral dosage form comprising the compound of Formula I or a pharmaceutically acceptable salt thereof, tenofovir alafenamide or a pharmaceutically acceptable salt thereof, and emtricitabine or a pharmaceutically acceptable salt thereof is provided. In certain embodiments, the dosage form comprises 50 mg of the compound of Formula I or a pharmaceutically acceptable salt thereof, 25 mg tenofovir alafenamide or a pharmaceutically acceptable salt thereof, and 200 mg emtricitabine. For instance, in certain embodiments, the dosage form comprises 50 mg of the compound of Formula I as a pharmaceutically acceptable salt thereof, 25 mg tenofovir alafenamide as a pharmaceutically acceptable salt thereof, and 200 mg emtricitabine. In certain embodiments, the dosage form comprises 52 mg of the compound of Formula II, 28 mg tenofovir alafenamide hemifumarate, and 200 mg emtricitabine.

In another aspect, a solid oral dosage form comprising 75 mg of the compound of Formula I as a pharmaceutically acceptable salt thereof. 25 mg tenofovir alafenamide as a pharmaceutically acceptable salt thereof, and 200 mg emtricitabine is provided. In certain embodiments, a solid oral dosage form comprising 75 mg of the compound of Formula I or a pharmaceutically acceptable salt thereof. 25 mg tenofovir alafenamide or a pharmaceutically acceptable salt thereof, and 200 mg emtricitabine is provided. In certain embodiments, a solid oral dosage form comprising 78 mg of the compound of Formula II. 28 mg tenofovir alafenamide hemifumarate, and 200 mg emtricitabine is provided.

The inventors have found that it is possible to formulate solid oral dosage forms that are pharmaceutically acceptable (i.e. pharmacologically efficacious and physically acceptable) while reducing the total amount of excipients necessary to achieve an acceptable pharmacokinetic profile. Accordingly, in one aspect a solid oral dosage form is provided, comprising 50 mg of the compound of Formula I or a pharmaceutically acceptable salt thereof, 25 mg tenofovir alafenamide or a pharmaceutically acceptable salt thereof, and 200 mg emtricitabine or a pharmaceutically acceptable salt thereof, wherein the dosage form has a total weight of less than 850 mg (e.g., less than 800 mg or less than 730 mg or less than 700 mg).

In another one aspect a solid oral dosage form is provided, comprising 75 mg of the compound of Formula I or a pharmaceutically acceptable salt thereof, 25 mg tenofovir alafenamide or a pharmaceutically acceptable salt thereof, and 200 mg emtricitabine or a pharmaceutically acceptable salt thereof, wherein the dosage form has a total weight of less than 850 mg (e.g., less than 800 mg or less than 700 mg).

In another aspect, a coated tablet comprising 50 mg of the compound of Formula I or a pharmaceutically acceptable salt thereof, 25 mg tenofovir alafenamide or a pharmaceutically acceptable salt thereof, and 200 mg emtricitabine or a pharmaceutically acceptable salt thereof is provided.

In another aspect, a coated tablet comprising 75 mg of the compound of Formula I or a pharmaceutically acceptable salt thereof. 25 mg tenofovir alafenamide or a pharmaceutically acceptable salt thereof, and 200 mg emtricitabine or a pharmaceutically acceptable salt thereof is provided.

In another aspect, a tablet comprising 52 mg of the compound of Formula II, 28 mg tenofovir alafenamide hemifumarate, and 200 mg emtricitabine is provided.

In another aspect, a tablet comprising 78 mg of the compound of Formula II, 28 mg tenofovir alafenamide hemifumarate, and 200 mg emtricitabine is provided.

In another aspect, a tablet comprising (a) 50 mg of the compound of Formula I or a pharmaceutically acceptable salt thereof, (b) 25 mg tenofovir alafenamide or a pharmaceutically acceptable salt thereof, and (c) 200 mg emtricitabine or a pharmaceutically acceptable salt thereof is provided, wherein (a) and (b) are segregated, and wherein the tablet has a total weight of less than about 1.5 g (e.g., less than about 1 g). Typically, (a) and (b) are present within separate layers in a multilayer tablet.

In another aspect, a tablet comprising (a) 75 mg of the compound of Formula I or a pharmaceutically acceptable salt thereof, (b) 25 mg tenofovir alafenamide or a pharmaceutically acceptable salt thereof, and (c) 200 mg emtricitabine or a pharmaceutically acceptable salt thereof is provided, wherein (a) and (b) are segregated, and wherein the tablet has a total weight of less than about 1.5 g (e.g., less than about 1 g). Typically, (a) and (b) are present within separate layers in a multilayer tablet.

In another aspect, a tablet comprising from 6.5-11.0% w/w of the compound of Formula I or a pharmaceutically acceptable salt thereof, 3.0-4.5% w/w tenofovir alafenamide or a pharmaceutically acceptable salt thereof, and 25-30% w/w emtricitabine or a pharmaceutically acceptable salt thereof is provided, where the weight percentages denote a proportion of the whole tablet. In some embodiments, (a) the compound of Formula I is present as of the compound of Formula II and/or (b) the tenofovir alafenamide is present as tenofovir alafenamide hemifumarate.

In another aspect, a tablet comprising from 9.5-11.5% w/w of the compound of Formula I or a pharmaceutically acceptable salt thereof. 2.5-4.5% w/w tenofovir alafenamide or a pharmaceutically acceptable salt thereof, and 26-33% w/w emtricitabine or a pharmaceutically acceptable salt thereof is provided, where the weight percentages denote a proportion of the whole tablet. In some embodiments, (a) the compound of Formula I is present as of the compound of Formula II and/or (b) the tenofovir alafenamide is present as tenofovir alafenamide hemifumarate.

The inventors have found that the use of a fixed dose combination may assist in achieving appropriate pharmacokinetic parameters and/or adequate tablet stability. In addition, the use of a multilayer tablet as a particular type of fixed dose combination may also provide pharmacokinetic and/or stability benefits. Accordingly, in another aspect a fixed dose combination tablet comprising (a) the compound of Formula I or a pharmaceutically acceptable salt thereof, (b) tenofovir alafenamide or a pharmaceutically acceptable salt thereof, and (c) emtricitabine or a pharmaceutically acceptable salt thereof is provided. Additionally, multilayer tablet comprising (a) the compound of Formula I or a pharmaceutically acceptable salt thereof, (b) tenofovir alafenamide or a pharmaceutically acceptable salt thereof, and (c) emtricitabine or a pharmaceutically acceptable salt thereof is provided.

In another aspect, a kit comprising (a) a tablet comprising the compound of Formula I or a pharmaceutically acceptable salt thereof, tenofovir alafenamide or a pharmaceutically acceptable salt thereof, and emtricitabine or a pharmaceutically acceptable salt thereof, and (b) a desiccant (e.g. silica gel) is provided.

Methods of producing solid oral dosage forms such as tablets are also provided, as discussed in more detail below.

In addition, methods for treating patients are provided, which are also discussed in more detail below.

DETAILED DESCRIPTION

Figure 1:
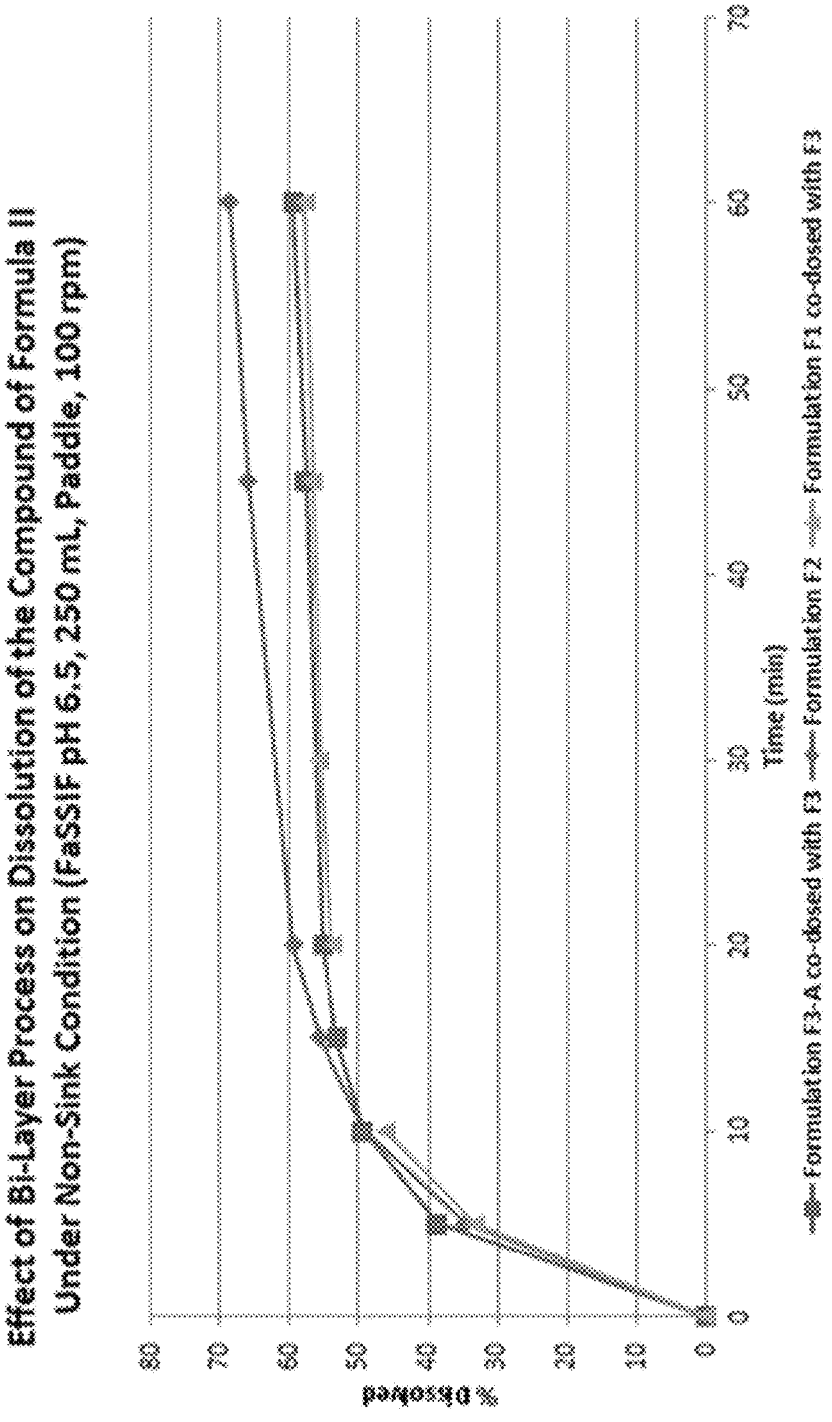
FIG. 1 shows the results of studies carried out on Formulations F1, F2, and F3 to assess the dissolution of 78 mg of the Compound of Formula II as a single agent compared to a bi-layer using fasted simulated intestinal fluid as a dissolution medium.

Typically, the oral dosage forms disclosed herein comprise three active pharmaceutical ingredients: the compound of Formula I (or a pharmaceutically acceptable salt thereof), tenofovir alafenamide (or a pharmaceutically acceptable salt thereof), and emtricitabine (or a pharmaceutically acceptable salt thereof).

(2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (2R,5S,13aR)-8-Hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide (Formula I), is a potent HIV integrase inhibitor with in vitro activity against wild type HIV-1. It has the following formula (see WO2014/100323):

(I)

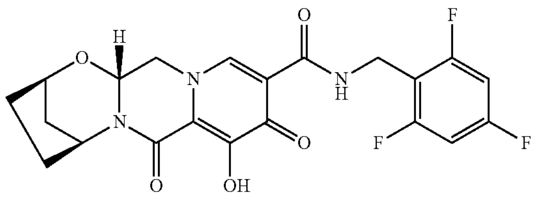

Its IUPAC name (2R,5S,13aR)-8-hydroxy-7,9-dioxo-N-(2,4,6-trifluorobenzyl)-2,3,4,5,7,9,13,13a-octahydro-2,5-methanopyrido[1',2':4,5]pyrazino[2,1-b][1,3]oxazepine-10-carboxamide. Its CAS name is 2,5-Methanopyrido[1',2':4,5]pyrazino[2,1-b][1,3]oxazepine-10-carboxamide, 2,3,4,5,7,9,13,13a-octahydro-8-hydroxy-7,9-dioxo-N-[(2,4,6-trifluorophenyl)methyl]-, (2R,5S,13aR). The compound of Formula I is a weak acid with pKa of 8.6. The aqueous solubility of the compound of Formula I free acid is pH-dependent, with solubility increasing with increasing pH, with a maximum at pH 10.5. The chemical stability of the compound of Formula I is also pH dependent, with maximum stability at pH 4. The compound of Formula I is considered a BCS Class 2 compound, with low solubility and high permeability.

Solid oral dosage forms disclosed herein include the compound of Formula I, usually in the form of a pharmaceutically acceptable salt. The compound of Formula I can be present within an oral dosage form in solvated or unsolvated form, and references to "Formula I" include both of these forms. Typically, the compound of Formula I is in the form of the compound of Formula II, having the formula below:

(II)

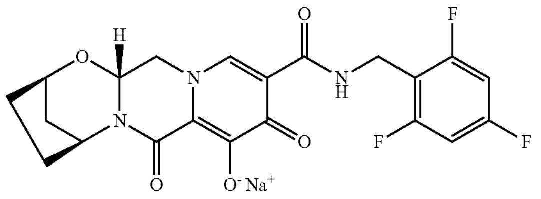

In certain specific embodiments, solid oral dosage forms containing 50 mg of the compound of Formula I, e.g., as about 52 mg of the compound of Formula II, are provided.

In certain specific embodiments, solid oral dosage forms containing 75 mg of the compound of Formula I, e.g., as about 78 mg of the compound of Formula II, are provided.

As used herein, and in the absence of a specific reference to a particular pharmaceutically acceptable salt and/or solvate of the compound of Formula I (e.g. Formula II), any dosages, whether expressed in e.g., milligrams or as a % by weight, should be taken as referring to the amount of the compound of Formula I free acid, i.e. the amount of:

(I)

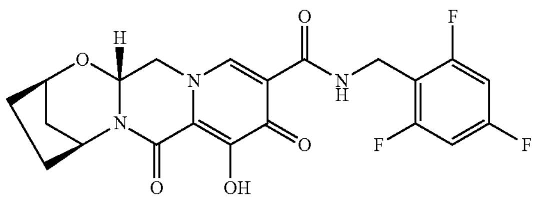

For example, therefore, a reference to "50 mg of the compound of Formula I or a pharmaceutically acceptable salt and/or solvate thereof" means an amount of the compound of Formula I or a pharmaceutically acceptable salt and/or solvate thereof which provides the same amount of the compound of Formula I as 50 mg of the compound of Formula I free acid.

For example, therefore, a reference to "75 mg of the compound of Formula I or a pharmaceutically acceptable salt and/or solvate thereof" means an amount of the compound of Formula I or a pharmaceutically acceptable salt and/or solvate thereof which provides the same amount of the compound of Formula I as 75 mg of the compound of Formula I free acid.

Tenofovir Alafenamide

Tenofovir alafenamide (TAF) is a nucleotide reverse transcriptase inhibitor having the formula below (see WO02/08241 A2):

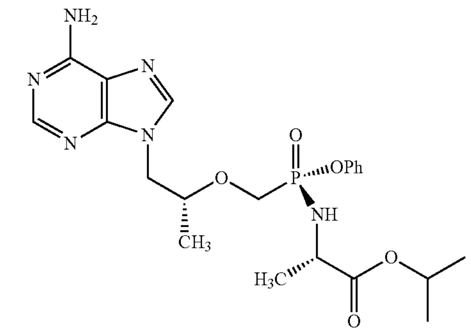 [SMILES: CC(C)OC(=O)[C@H](C)N[P@](=O)(CO[C@H](C)Cn1cnc2c(N)ncnc21)Oc1ccccc1]

Its IUPAC name is(S)-isopropyl-2-(((S)-((((R)-1-(6-amino-9H-purin-9-yl) propan-2-yl)oxy)methyl) (phenoxy) phosphoryl)amino) propanoate. It is also referred to as {9-[(R)-2-[[(S)-[[(S)-1-(isopropoxycarbonyl)ethyl]amino] phenoxyphosphinyl]-methoxy]propyl]adenine}. Tenofovir alafenamide is a weak base, with a pKa of 3.9. Its solubility increases with decreasing pH, with a maximum solubility at about pH 3. Tenofovir alafenamide is considered a BCS Class 3 compound, with high equilibrium solubility and lower apparent permeability.

Solid oral dosage forms disclosed herein include tenofovir alafenamide, usually in the form of a pharmaceutically acceptable salt. Tenofovir alafenamide can be present within an oral dosage form in solvated or unsolvated form, and references to "tenofovir alafenamide" include both of these forms. In particular, tenofovir alafenamide may be associated with fumarate, such as monofumarate or hemifumarate. Typically, tenofovir alafenamide is in the form of tenofovir alafenamide hemifumarate having the formula below (see WO 2013/025788 A1):

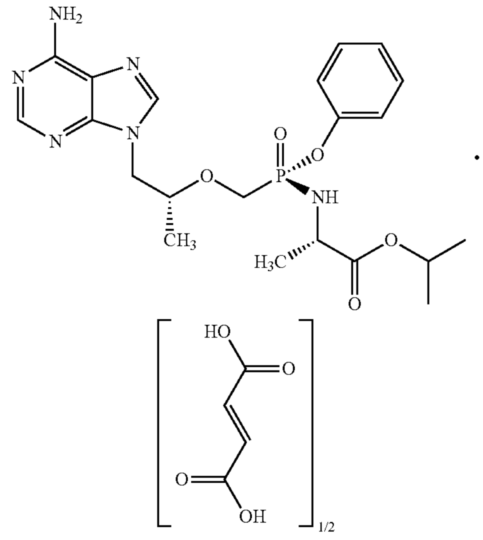

As used herein, and in the absence of a specific reference to a particular pharmaceutically acceptable salt and/or solvate of tenofovir alafenamide, any dosages, whether expressed in e.g. milligrams or as a % by weight, should be taken as referring to the amount of tenofovir alafenamide, i.e. the amount of:

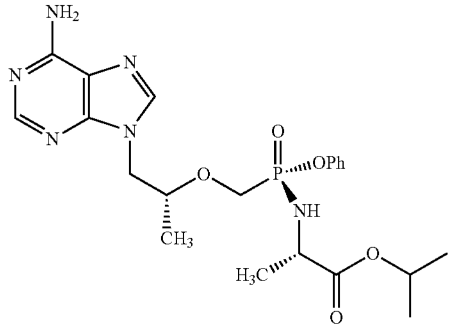 [SMILES: CC(C)OC(=O)[C@H](C)N[P@](=O)(CO[C@H](C)Cn1cnc2c(N)ncnc21)Oc1ccccc1]

For example, therefore, a reference to "25 mg tenofovir alafenamide or a pharmaceutically acceptable salt and/or solvate thereof" means an amount of tenofovir alafenamide or a pharmaceutically acceptable salt and/or solvate thereof which provides the same amount of tenofovir alafenamide as 25 mg of tenofovir alafenamide free base.

The amount of tenofovir alafenamide in a solid oral dosage form provided herein is generally between 10 mg and 30 mg, for instance within the range of 20 mg to 30 mg, and more typically between 24 mg and 28 mg. In certain specific embodiments, solid oral dosage forms containing 25 mg of tenofovir alafenamide e.g., as about 28 mg of tenofovir alafenamide hemifumarate, are provided.

Emtricitabine

Emtricitabine (FTC) is a nucleoside reverse transcriptase inhibitor having the formula below:

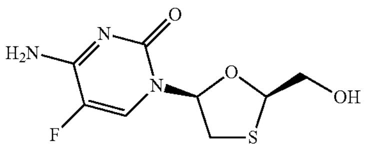 [SMILES: Nc1nc(=O)n([C@@H]2CS[C@H](CO)O2)cc1F]

Its IUPAC name is 4-amino-5-fluoro-1-[(2R,5S)-2-(hydroxymethyl)-1,3-oxathiolan-5-yl]-1,2-dihydropyrimidin-2-one. It is also referred to as 5-fluoro-1-[(2R,5S)-2-(hydroxymethyl)-1,3-oxathiolan-5-yl]cytosine. It is currently authorised as part of EMTRIVAR (emtricitabine 200 mg), TRUVADA® (emtricitabine 200 mg, tenofovir disoproxil fumarate 300 mg), ATRIPLA® (emtricitabine 200 mg, efavirenz 600 mg, tenofovir disoproxil fumarate 300 mg) and STRIBILD® (emtricitabine 200 mg, cobicistat 150 mg, tenofovir disoproxil fumarate 300 mg, elvitegravir 150 mg) and COMPLERA®/EVIPLERA® (rilpivirine 25 mg, emtricitabine 200 mg, tenofovir disoproxil fumarate 300 mg).

Emtricitabine is a free base, exhibiting a pKa of 2.65. Solubility is enhanced under acidic conditions. It is considered a BCS Class 1 compound, with high solubility and high permeability.

Solid oral dosage forms disclosed herein include emtricitabine, optionally as a pharmaceutically acceptable salt. Emtricitabine can be present within an oral dosage form in solvated or unsolvated form, and references to "emtricitabine" include both of these forms. Typically, emtricitabine is present as a free base.

As used herein, and in the absence of a specific reference to a particular pharmaceutically acceptable salt and/or solvate of emtricitabine, any dosages, whether expressed in e.g., milligrams or as a % by weight, should be taken as referring to the amount of emtricitabine, i.e. the amount of:

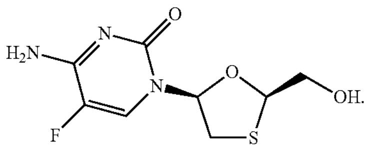 [SMILES: Nc1nc(=O)n([C@@H]2CS[C@H](CO)O2)cc1F]

For example, therefore, a reference to "200 mg emtricitabine or a pharmaceutically acceptable salt and/or solvate thereof" means an amount of emtricitabine or a pharmaceutically acceptable salt and/or solvate thereof which provides the same amount of emtricitabine as 200 mg of emtricitabine free base.

The amount of emtricitabine in a solid oral dosage form provided herein is generally between 180 mg and 220 mg, for instance between 190 mg and 210 mg, and more typically between 195 mg and 205 mg. In certain specific embodiments, solid oral dosage forms containing 200 mg of emtricitabine are provided.

Solid Oral Dosage Forms

The inventors have successfully formulated the compound of Formula I, emtricitabine and tenofovir alafenamide in a single, stable dosage form that is pharmacologically efficacious and physically acceptable. The solid oral dosage forms disclosed herein are intended for pharmaceutical use in human subjects. Accordingly, they must be of an appropriate size and weight for oral human administration (e.g., they should have a total weight of less than about 1.5 g, e.g., less than about 1.0 g), in addition to being therapeutically efficacious.

In certain embodiments, formulations of the three active ingredients into a solid oral dosage form which has a total weight of less than about 1.0 g are provided, for instance less than about 800 mg, or even less than about 750 mg, or even less than 700 mg. This is advantageous given that TRIUMEQ® (abacavir sulfate equivalent to 600 mg of abacavir, dolutegravir sodium equivalent to 50 mg of dolutegravir, and 300 mg of lamivudine) has a total weight of more than about 1000 mg, based on the weight of the active ingredients in each tablet (due to the amount of excipients that are required to produce a pharmaceutically acceptable tablet). The provision of a relatively small dosage form (in particular a tablet) represents a clinical advantage because it may be expected to increase patient convenience and thus compliance as compared to larger dosage forms which are more burdensome for patients to swallow. In specific embodiments, the solid oral dosage form disclosed herein has a total weight of between 700 and 750 mg. In certain embodiments, the solid oral dosage form disclosed herein has a total weight of between 700 and 725 mg, or about 700 mg. In specific embodiments, the solid oral dosage form disclosed herein has a total weight of between about 50 and about 750 mg, between about 100 and about 750 mg, between about 200 and about 750 mg, or between about 250 and about 750 mg. The presently disclosed dosage forms may comprise less than 600 mg of excipients, such as less than 500 mg of excipients, or less than 450 mg of excipients. For example, solid oral dosage forms disclosed herein may comprise between 300 and 600 mg of excipients, or between 350 mg and 500 mg of excipients, or between 400 mg and 500 mg of excipients. Most typically, solid oral dosage forms disclosed herein comprise between 425 mg and 450 mg of excipients. In such embodiments, the dosage forms comprise as active ingredients (a) 50 mg of the compound of Formula I or a pharmaceutically acceptable salt thereof, (b) 25 mg tenofovir alafenamide or a pharmaceutically acceptable salt thereof, and (c) 200 mg emtricitabine or a pharmaceutically acceptable salt thereof. In certain embodiments, the dosage forms comprise as active ingredients (a) 52 mg of the compound of Formula II, (b) 28 mg tenofovir alafenamide hemifumarate, and (c) 200 mg emtricitabine. In some embodiments, the dosage forms comprise as active ingredients (a) 75 mg of the compound of Formula I or a pharmaceutically acceptable salt thereof, (b) 25 mg tenofovir alafenamide or a pharmaceutically acceptable salt thereof, and (c) 200 mg emtricitabine or a pharmaceutically acceptable salt thereof. In certain embodiments, the dosage forms comprise as active ingredients (a) 78 mg of the compound of Formula II. (b) 28 mg tenofovir alafenamide hemifumarate, and (c) 200 mg emtricitabine.

The solid oral dosage forms disclosed herein will typically be in the form of a fixed dose combination tablet. This is because the inventors have found that the use of fixed dose combination tablets may assist in optimizing the pharmacokinetic properties of the active ingredients, particularly the total exposure of the compound of Formula I or a pharmaceutically acceptable salt thereof, as measured by area under the curve (AUC) and $C_{max}$. In particular embodiments, the solid oral dosage forms disclosed herein are in the form of a multilayer tablet. In certain embodiments, the use of a fixed dose combinations, e.g., multilayer tablets, may affect the dissolution profile of one or more of the active ingredients within the dosage form, and is therefore likely to have an impact on the in vivo pharmacokinetics of the dosage form. In particular, it has been observed that the dissolution of the compound of Formula I (e.g., as Formula II) varies depending on whether the tablet is in a fixed dose combination formulation with tenofovir alafenamide and emtricitabine and/or whether the tablet is a monolayer or multilayer tablet. It has also been observed that the presence of certain excipients in the multilayer tablet formulation (or absence of others) affects the dissolution profile of one or more of the active ingredients within the dosage form. The provision of a tablet with particular pharmacokinetic parameters, e.g., pharmacokinetic parameters is a particular advantage afforded by the present disclosure.

In one embodiment, a multilayer tablet comprising (a) the compound of Formula I or a pharmaceutically acceptable salt thereof, (b) tenofovir alafenamide or a pharmaceutically acceptable salt thereof, and (c) emtricitabine or a pharmaceutically acceptable salt thereof is provided. Typically, each layer contains at least one of (a), (b), and (c). For instance, in certain embodiments, the tablet comprises a first layer comprising (a) the compound of Formula I or a pharmaceutically acceptable salt thereof, and a second layer comprising (b) tenofovir alafenamide or a pharmaceutically acceptable salt thereof, and further comprises (c) emtricitabine or a pharmaceutically acceptable salt thereof. In such embodiments, typically the first layer is substantially free of tenofovir alafenamide or a pharmaceutically acceptable salt thereof, and/or the second layer is substantially free of the compound of Formula I or a pharmaceutically acceptable salt thereof. In one embodiment the first layer is substantially free of tenofovir alafenamide or a pharmaceutically acceptable salt thereof (e.g., the first layer contains less than 1% by weight tenofovir alafenamide or a pharmaceutically acceptable salt thereof), and the second layer is substantially free of the compound of Formula I or a pharmaceutically acceptable salt thereof (e.g. the second layer contains less than 1% by weight of the compound of Formula I or a pharmaceutically acceptable salt thereof).

A particular embodiment provides a tablet, wherein the first layer comprises the compound of Formula I or a pharmaceutically acceptable salt thereof (e.g., Formula II) and is substantially free of tenofovir alafenamide or a pharmaceutically acceptable salt thereof (e.g., the first layer contains less than 1% by weight tenofovir alafenamide or a pharmaceutically acceptable salt thereof), and the second layer comprises tenofovir alafenamide or a pharmaceutically acceptable salt thereof and emtricitabine or a pharmaceutically acceptable salt thereof and is substantially free of the compound of Formula I or a pharmaceutically acceptable salt thereof (e.g., the second layer contains less than 1% by weight of the compound of Formula I or a pharmaceutically acceptable salt thereof). In a particular embodiment, a tablet is provided, wherein the first layer comprises 52 mg of the compound of Formula II and is substantially free of tenofovir alafenamide or a pharmaceutically acceptable salt thereof (e.g., the first layer contains less than 1% by weight tenofovir alafenamide or a pharmaceutically acceptable salt thereof), and the second layer comprises 28 mg tenofovir alafenamide hemifumarate and 200 mg emtricitabine and is substantially free of the compound of Formula I or a pharmaceutically acceptable salt thereof (e.g., the second layer contains less than 1% by weight of the compound of Formula I or a pharmaceutically acceptable salt thereof), wherein the first layer has a total weight of less than about 400 mg, such as about 325 mg, and the second layer has a total weight of less than about 450 mg, such as about 380 mg. In one embodiment, the layer containing tenofovir alafenamide or a pharmaceutically acceptable salt thereof does not contain lactose and/or starch. In one embodiment, the layer containing the compound of Formula I or a pharmaceutically acceptable salt thereof does not contain lactose, crospovidone and/or sodium stearyl fumarate.

A particular embodiment provides a tablet, wherein the first layer comprises the compound of Formula I or a pharmaceutically acceptable salt thereof (e.g., Formula II) and is substantially free of emtricitabine or a pharmaceutically acceptable salt thereof (e.g., the first layer contains less than 1% by weight emtricitabine or a pharmaceutically acceptable salt thereof), and (b) the second layer comprises tenofovir alafenamide or a pharmaceutically acceptable salt thereof and emtricitabine or a pharmaceutically acceptable salt thereof and is substantially free of the compound of Formula I or a pharmaceutically acceptable salt thereof (e.g., the second layer contains less than 1% by weight of the compound of Formula I or a pharmaceutically acceptable salt thereof). In a particular embodiment, a tablet is provided, wherein (a) the first layer comprises 52 mg of the compound of Formula II and is substantially free of emtricitabine or a pharmaceutically acceptable salt thereof (e.g., the first layer contains less than 1% by weight emtricitabine or a pharmaceutically acceptable salt thereof), and (b) the second layer comprises 28 mg tenofovir alafenamide hemifumarate and 200 mg emtricitabine and is substantially free of the compound of Formula I or a pharmaceutically acceptable salt thereof (e.g., the second layer contains less than 1% by weight of the compound of Formula I or a pharmaceutically acceptable salt thereof), wherein the first layer has a total weight of less than about 400 mg, such as about 325 mg, and the second layer has a total weight of less than about 450 mg, such as about 380 mg. In one embodiment, the layer containing emtricitabine or a pharmaceutically acceptable salt thereof does not contain lactose and/or starch. In one embodiment, the layer containing the compound of Formula I or a pharmaceutically acceptable salt thereof does not contain lactose, crospovidone and/or sodium stearyl fumarate.

A particular embodiment provides a tablet, wherein the first layer comprises the compound of Formula I or a pharmaceutically acceptable salt thereof (e.g., Formula II) and is substantially free of tenofovir alafenamide and emtricitabine or a pharmaceutically acceptable salt thereof (e.g., the first layer contains less than 1% by weight each of tenofovir alafenamide and emtricitabine or a pharmaceutically acceptable salt thereof), and (b) the second layer comprises tenofovir alafenamide or a pharmaceutically acceptable salt thereof and emtricitabine or a pharmaceutically acceptable salt thereof and is substantially free of the compound of Formula I or a pharmaceutically acceptable salt thereof (e.g., the second layer contains less than 1% by weight of the compound of Formula I or a pharmaceutically acceptable salt thereof). In a particular embodiment, a tablet is provided, wherein (a) the first layer comprises 52 mg of the compound of Formula II and is substantially free of tenofovir alafenamide and emtricitabine or a pharmaceutically acceptable salt thereof (e.g., the first layer contains less than 1% by weight tenofovir alafenamide and emtricitabine or a pharmaceutically acceptable salt thereof), and (b) the second layer comprises 28 mg tenofovir alafenamide hemifumarate and 200 mg emtricitabine and is substantially free of the compound of Formula I or a pharmaceutically acceptable salt thereof (e.g., the second layer contains less than 1% by weight of the compound of Formula I or a pharmaceutically acceptable salt thereof), wherein the first layer has a total weight of less than about 400 mg, such as about 325 mg, and the second layer has a total weight of less than about 450 mg, such as about 380 mg. In one embodiment, the layer containing tenofovir alafenamide and emtricitabine or a pharmaceutically acceptable salt thereof does not contain lactose and/or starch. In one embodiment, the layer containing the compound of Formula I or a pharmaceutically acceptable salt thereof does not contain lactose, crospovidone and/or sodium stearyl fumarate.

In a particular embodiment, a tablet is provided, wherein (a) the first layer comprises 78 mg of the compound of Formula II and is substantially free of tenofovir alafenamide or a pharmaceutically acceptable salt thereof (e.g., the first layer contains less than 1% by weight tenofovir alafenamide or a pharmaceutically acceptable salt thereof), and (b) the second layer comprises 28 mg tenofovir alafenamide hemifumarate and 200 mg emtricitabine and is substantially free of the compound of Formula I or a pharmaceutically acceptable salt thereof (e.g., the second layer contains less than 1% by weight of the compound of Formula I or a pharmaceutically acceptable salt thereof), wherein the first layer has a total weight of less than about 400 mg, such as about 355 mg, and the second layer has a total weight of less than about 450 mg, such as about 380 mg. In one embodiment, the layer containing tenofovir alafenamide or a pharmaceutically acceptable salt thereof does not contain lactose and/or starch.

Unless otherwise specified, the terms "first layer", "second layer", "third layer" and so forth do not specify a particular order or orientation of the multilayer tablet formulations disclosed herein. Rather, these terms are used to distinguish the sections of the composition from each other and to specify the characteristics or components of each section or compartment. By way of example, in an embodiment, a tablet is provided wherein a first layer comprises 52 mg of the compound of Formula II and is substantially free of tenofovir alafenamide or a pharmaceutically acceptable salt thereof (e.g., the first layer contains less than 1% by weight tenofovir alafenamide or a pharmaceutically acceptable salt thereof), and (b) the second layer comprises 28 mg tenofovir alafenamide hemifumarate and 200 mg emtricitabine and is substantially free of the compound of Formula I or a pharmaceutically acceptable salt thereof (e.g., the second layer contains less than 1% by weight of the compound of Formula I or a pharmaceutically acceptable salt thereof), wherein the first layer has a total weight of less than about 400 mg, such as about 325 mg, and the second layer has a total weight of less than about 450 mg, such as about 380 mg. The first layer may be synthesized first or may be synthesized second. The first layer may be on the bottom or may be on the top or may be on a side. The term "first layer" is not limiting as to order and orientation.

The tablets disclosed herein are typically immediate release tablets. In one embodiment, a tablet is provided which releases at least 50% of the compound of Formula I or a pharmaceutically acceptable salt thereof in about 20 minutes, measured using USP apparatus II, in 333 mL of fasted state simulated intestinal fluid, pH 6.5, at 37° C., and paddle speed of 100 rpm. In certain embodiments, the tablets disclosed herein release at least 60% of the compound of Formula I or a pharmaceutically acceptable salt thereof in 20 minutes, measured using USP apparatus II, in 333 mL of 50 mM fasted state simulated intestinal fluid, at 37° C., and paddle speed of 100 rpm. In some embodiments, a tablet that releases at least 70% of the compound of Formula I in 60 minutes is provided, measured using USP Apparatus II, in 333 mL of fasted state simulated intestinal fluid at 37° C., and paddle speed of 100 rpm.

Tablets disclosed herein will generally have a hardness within the range 14-20 kP, and, in certain specific embodiments, have a hardness of 17 kP. Hardness can conveniently be assessed by driving an anvil to compress a tablet at a constant loading rate until it fractures, operating in accordance with USP <1217> (using e.g., a TBH 220. ERWEKA GmbH. Heusenstamm Germany hardness tester).

Tablets disclosed herein will generally have a friability of <1% by weight. Friability can be assessed according to USP <1216>.

The core of a tablet provided herein may have a hardness of between 14-20 kP, and a friability of <1% by weight.

Tablets will typically include one or more excipients. Excipients should be compatible with the other ingredients of the formulation and physiologically innocuous to the recipient thereof. Examples of suitable excipients are well known to the person skilled in the art of tablet formulation and may be found e.g., in *Handbook of Pharmaceutical Excipients* (eds. Rowe, Sheskey & Quinn), 6th edition 2009. As used herein the term "excipients" is intended to refer to inter alia basifying agents, solubilisers, glidants, fillers, binders, lubricant, diluents, preservatives, surface active agents, dispersing agents and the like. The term also includes agents such as sweetening agents, flavoring agents, coloring agents, preserving agents, and coating agents. Such components will generally be present in admixture within the tablet.

Examples of solubilisers include, but are not limited to, ionic surfactants (including both ionic and non-ionic surfactants) such as sodium lauryl sulphate, cetyltrimethylammonium bromide, polysorbates (such as polysorbate 20 or 80), poloxamers (such as poloxamer 188 or 207), and macrogols. In a particular embodiment, a tablet that comprises the compound of Formula I or a pharmaceutically acceptable salt thereof, includes a polysorbate, in particular polysorbate 20. In certain specific embodiments, the amount of polysorbate 20 in a tablet disclosed herein is less than about 5 mg, such as less than about 1 mg, or about 0.5 mg.

Examples of lubricants, glidants and flow aids include, but are not limited to, magnesium stearate, calcium stearate, stearic acid, hydrogenated vegetable oil, glyceryl palmitostearate, glyceryl behenate, sodium stearyl fumarate, colloidal silicon dioxide, and talc. The amount of lubricant in a tablet is generally between about 0.5-5% by weight. In certain embodiments, the amount of lubricant in a tablet is about 1.5% by weight. In certain specific embodiments, tablets disclosed herein include magnesium stearate. In certain other embodiments, the tablets disclosed herein do not include sodium stearyl fumarate. In certain embodiments, the tablet includes less than about 10 mg magnesium stearate, or less than about 7.5 mg magnesium stearate. In certain embodiments, the tablet includes less than about 9 mg magnesium stearate, or less than about 8.75 mg magnesium stearate. In certain embodiments, the tablet includes about 5 mg to about 10 mg magnesium stearate, or about 6 mg to about 9 mg magnesium stearate, or about 7 mg to about 9 mg magnesium stearate, or about 8 mg to about 9 mg magnesium stearate, or about 8.1 mg, about 8.2 mg, about 8.3 mg, about 8.4 mg, about 8.5 mg, about 8.6 mg, about 8.7 mg, about 8.8 mg or about 8.9 mg magnesium stearate.

Examples of disintegrants include, but are not limited to, starches, celluloses, cross-linked PVP (crospovidone), sodium starch glycolate, croscarmellose sodium, etc. In certain embodiments, the tablets disclosed herein include croscarmellose sodium. In certain other embodiments, the tablets disclosed herein do not include crospovidone. In certain embodiments, the tablet includes less than about 50 mg croscarmellose sodium, or less than about 25 mg croscarmellose sodium. In certain embodiments, the tablet includes about 30 mg to about 60 mg croscarmellose sodium, or about 40 mg to about 60 mg croscarmellose sodium, or about 45 mg to about 55 mg croscarmellose sodium, or about 45 mg, about 46 mg, about 47 mg, about 48 mg, about 49 mg, about 50 mg, about 51 mg, about 52 mg or about 53 mg, or about 54 mg, or about 55 mg croscarmellose sodium.

Examples of fillers (also known as bulking agents or diluents) include, but are not limited to, starches, maltodextrins, polyols (such as lactose), and celluloses. In certain embodiments, tablets provided herein may microcrystalline cellulose. In certain other embodiments, tablets provided herein do not contain lactose. In certain embodiments, tablets provided herein include less than about 300 mg microcrystalline cellulose, in particular less than about 250 mg microcrystalline cellulose, and/or less than about 225 mg microcrystalline cellulose. In certain embodiments, tablets provided herein include less than about 500 mg microcrystalline cellulose, or less than about 450 mg microcrystalline cellulose, or less than about 400 mg microcrystalline cellulose, or less than about 375 mg microcrystalline cellulose. In certain embodiments, tablets provided herein include about 250 mg to about 500 mg microcrystalline cellulose, or about 300 mg to about 450 mg microcrystalline cellulose, or about 300 mg to about 400 mg microcrystalline cellulose, or about 325 mg to about 375 mg microcrystalline cellulose, or about 350 mg to about 370 mg microcrystalline cellulose. In certain embodiments, tablets provided herein include about 300 mg, or about 310 mg, or about 320 mg, or about 330 mg, or about 340 mg, or about 350 mg, or about 360 mg, or about 370 mg, or about 380 mg, or about 390 mg, or about 400 mg microcrystalline cellulose.

Examples of binders include, but are not limited to, cross-linked PVP, HPMC, sucrose, starches, etc.

In certain embodiments, tablets provided herein are uncoated. In certain other embodiments, tablets provided herein are coated (in which case they include a coating). Although uncoated tablets may be used, it is more usual in the clinical setting to provide a coated tablet, in which case a conventional non-enteric coating may be used. Film coatings are known in the art and can be composed of hydrophilic polymer materials, but are not limited to, polysaccharide materials, such as hydroxypropylmethyl cellulose (HPMC), methylcellulose, hydroxyethyl cellulose (HEC), hydroxypropyl cellulose (HPC), poly(vinylalcohol-co-ethylene glycol) and other water soluble polymers. Though in certain embodiments the water soluble material included in the film coating of the embodiments disclosed herein includes a single polymer material, in certain other embodiments it is formed using a mixture of more than one polymer. In certain embodiments, the coating is yellow or brown. Suitable coatings include, but are not limited to, polymeric film coatings such as those comprising polyvinyl alcohol e.g. "Opadry® II" (which includes part-hydrolysed PVA, titanium dioxide, macrogol 3350 (PEG) and talc, with optional colouring such as iron oxide (e.g., iron oxide red or iron oxide black) or indigo carmine or iron oxide yellow or FD&C yellow #6). The amount of coating is generally between about 2-4% of the core's weight, and in certain specific embodiments, about 3%. Unless specifically stated otherwise, where the dosage form is coated, it is to be understood that a reference to % weight of the tablet means that of the total tablet, i.e. including the coating.

Pharmacokinetics

In certain embodiments, the pharmaceutical compositions disclosed herein result in increased systemic exposure ($AUC_{inf}$; $C_{max}$) for the compound of Formula I or a pharmaceutically acceptable salt thereof. In particular embodiments, the multilayer tablet formulations disclosed herein result in increased systemic exposure for the compound of Formula I or a pharmaceutically acceptable salt thereof compared to a single agent tablet formulation of the compound of Formula I or a pharmaceutically acceptable salt thereof. In certain embodiments, the multilayer tablet formulation results in an increase of at least about 20% in the systemic exposure of the compound of Formula I or a pharmaceutically acceptable salt thereof compared to a single agent tablet formulation of the compound of Formula I or a pharmaceutically acceptable salt thereof. In some embodiments, the increase in systemic exposure is at least about 25% or at least about 30%. In some embodiments, the increase in systemic exposure is about 30%.

$C_{max}$ $C_{max}$ is the maximum observed plasma/serum concentration of drug.

In particular embodiments, a pharmaceutical composition comprising a tablet containing 75 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $C_{max}$ of the compound of Formula I in fasted patients of from about 5300 to about 8900 ng/mL, e.g., about 7100 ng/mL.

In certain specific embodiments, a pharmaceutical composition comprising a tablet containing 75 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $C_{max}$ of emtricitabine in fasted patients of from about 1700 to about 2800 ng/mL, e.g., about 2300 ng/mL.

In certain specific embodiments, a pharmaceutical composition comprising a tablet containing 75 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $C_{max}$ of tenofovir alafenamide in fasted patients of from about 190 to about 320 ng/mL, e.g., about 250 ng/mL.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $C_{max}$ of the Compound of Formula I of from about from about 4200 ng/mL to about 8000 ng/mL, regardless of whether the subject was fed or fasted.

In particular embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $C_{max}$ of the compound of Formula I in fasted patients of from about 4200 ng/mL to about 6500 ng/mL, or from about 4700 ng/mL to about 5300 ng/mL, or from about 4700 ng/mL to about 5800 ng/mL, or from about 5000 ng/mL to about 5500 ng/mL.

In particular embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $C_{max}$ of the compound of Formula I in fed patients of from about 4500 ng/mL to about 8000 ng/mL, or from about 4800 ng/mL to about 7900 ng/mL, or from about 5300 ng/mL to about 6900 ng/mL, or from about 5600 ng/mL to about 6600 ng/mL.

In certain specific embodiments, a pharmaceutical composition comprising a tablet containing 50 mg of the compound of Formula I or a pharmaceutically acceptable salt thereof, 200 ing emtricitabine or a pharmaceutically acceptable salt thereof, and 25 mg tenofovir alafenamide or a pharmaceutically acceptable salt thereof provide a plasma $C_{max}$ of emtricitabine of from about from about 1770 ng/mL to about 2800 ng/mL, regardless of whether the subject was fed or fasted.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $C_{max}$, of emtricitabine in fasted patients of from about 1770 ng/mL to about 2800 ng/mL, or from about 2000 ng/mL to about 2600 ng/mL, or from about 2000 ng/mL to about 2500 ng/mL, or from about 2100 ng/mL to about 2400 ng/mL.

In particular embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $C_{max}$ of emtricitabine in fed patients of from about 1000 ng/mL to about 3000 ng/mL, or from about 1500 ng/mL to about 2000 ng/m from about 1700 ng/mL to about 2200 ng/mL L, or from about 1800 ng/mL to about 2100 ng/mL.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $C_{max}$ of tenofovir alafenamide of from about from about 185 ng/mL to about 315 ng/mL, regardless of whether the subject was fed or fasted.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $C_{max}$ of tenofovir alafenamide in fasted patients of from about 185 ng/mL to about 315 ng/mL, or from about 200 ng/mL to about 300 ng/mL, or from about 210 ng/mL to about 290 ng/mL, or from about 220 ng/mL to about 275 ng/mL, or from about 230 ng/mL to about 265 ng/mL, or from about 240 ng/mL to about 260 ng/mL.

In particular embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $C_{max}$ of tenofovir alafenamide in fed patients of from about 150 ng/mL to about 350 ng/mL, or from about 185 ng/mL to about 300 ng/m from about 210 ng/mL to about 280 ng/mL L, or from about 250 ng/mL to about 265 ng/mL.

$AUC_{inf}$ $AUC_{inf}$ is the area under the plasma/serum concentration versus time curve extrapolated to infinite time, calculated as $AUC_{0\text{-}last}+(C_{last}/\lambda_Z)$.

In certain specific embodiments, a pharmaceutical composition comprising a tablet containing 75 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{inf}$ of the compound of Formula I in fed patients of from about 117000 to about 196000 h·ng/mL, e.g., about 157000 h·ng/mL.

In certain specific embodiments, a pharmaceutical composition comprising a tablet containing 75 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{inf}$ of emtricitabine in fed patients of from about 8700 to about 14500 h·ng/mL, e.g., about 2300 h·ng/mL.

In certain specific embodiments, a pharmaceutical composition comprising a tablet containing 75 mg of the compound of Formula I or a pharmaceutically acceptable salt thereof. 200 mg emtricitabine or a pharmaceutically acceptable salt thereof, and 25 mg tenofovir alafenamide or a pharmaceutically acceptable salt thereof provide a plasma $AUC_{inf}$ of tenofovir alafenamide in fed patients of from about 150 and 260 h·ng/mL, e.g., about 210 h·ng/mL.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{inf}$ of the Compound of Formula I of from about from about 84450 h·ng/mL to about 141000 h·ng/mL, regardless of whether the subject was fed or fasted.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{inf}$ of the compound of Formula I in fasted patients of from about 84450 h·ng/mL to about 141000 h·ng/mL, or from about 90000 h·ng/mL to about 135000 h·ng/mL, or from about 95000 h·ng/mL to about 130000 h·ng/mL, or from about 100000 h·ng/mL to about 125000 h·ng/mL, or from about 110000 h·ng/mL to about 120000 h·ng/mL.

In particular embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{inf}$ of the compound of Formula I in fed patients of from about 100000 h·ng/mL to about 200000 ng/mL, or from about 112000 h·ng/mL to about 175000 ng/mL, or from about 126000 h·ng/mL to about 155000 ng/mL, or from about 133000 h·ng/mL to about 147000 ng/mL.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{inf}$ of emtricitabine of from about from about 8100 h·ng/mL, to about 13600 h·ng/mL, regardless of whether the subject was fed or fasted.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{inf}$ of emtricitabine in fasted patients of from about 8100 h·ng/mL to about 13600 h·ng/mL, or from about 8700 h·ng/mL to about 13000 h·ng/mL, or from about 92000 h·ng/mL to about 12500 h·ng/mL, or from about 9700 h·ng/mL to about 12000 h·ng/mL, or from about 10000 h·ng/mL to about 11400 h·ng/mL.

In particular embodiments, a pharmaceutical composition comprising a tablet containing 50 mg of the compound of Formula I or a pharmaceutically acceptable salt thereof. 200 mg emtricitabine or a pharmaceutically acceptable salt thereof, and 25 mg tenofovir alafenamide or a pharmaceutically acceptable salt thereof provide a plasma $AUC_{inf}$ of emtricitabine in fed patients of from about 7500 h·ng/mL to about 15000 ng/mL, or from about 8300 h·ng/mL to about 14000 ng/mL, or from about 9500 h·ng/mL to about 12000 ng/mL, or from about 9900 h·ng/mL to about 11600 ng/mL.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{inf}$ of tenofovir alafenamide of from about from about 200 h·ng/mL to about 500 h·ng/mL, regardless of whether the subject was fed or fasted.

In certain specific embodiments, a pharmaceutical composition comprising a tablet containing 50 mg of the compound of Formula I or a pharmaceutically acceptable salt thereof. 200 mg emtricitabine or a pharmaceutically acceptable salt thereof, and 25 mg tenofovir alafenamide or a pharmaceutically acceptable salt thereof provide a plasma $AUC_{inf}$ of tenofovir alafenamide in fasted patients of from about 200 h·ng/mL to about 265 h·ng/mL, or from about 200 h·ng/mL to about 300 h·ng/mL, or from about 210 h·ng/mL to about 290 h·ng/mL, or from about 220 h·ng/mL to about 270 h·ng/mL, or from about 230 h·ng/mL to about 265 h·ng/mL.

In particular embodiments, a pharmaceutical composition comprising a tablet containing 50 mg of the compound of Formula I or a pharmaceutically acceptable salt thereof. 200 mg emtricitabine or a pharmaceutically acceptable salt thereof, and 25 mg tenofovir alafenamide or a pharmaceutically acceptable salt thereof provide a plasma $AUC_{inf}$ of tenofovir alafenamide in fed patients of from about 200 h·ng/mL to about 500 ng/mL, or from about 230 h·ng/mL to about 400 ng/mL, or from about 260 h·ng/mL to about 350 ng/mL, or from about 275 h·ng/mL to about 370 ng/mL.

$AUC_{last}$ $AUC_{last}$ is the area under the plasma/serum concentration versus time curve from time zero to the last quantifiable concentration.

In certain specific embodiments, a pharmaceutical composition comprising a tablet containing 75 mg of the compound of Formula I or a pharmaceutically acceptable salt thereof. 200 mg emtricitabine or a pharmaceutically acceptable salt thereof, and 25 mg tenofovir alafenamide or a pharmaceutically acceptable salt thereof provide a plasma AUC last of the compound of Formula I in fed patients of from about 114000 to about 190000 h·ng/mL, e.g., about 152000 h·ng/mL.

In certain specific embodiments, a pharmaceutical composition comprising a tablet containing 75 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{last}$ of emtricitabine in fed patients of from about 8600 to about 14000 h·ng/mL, e.g., about 11000 h·ng/mL.

In certain specific embodiments, a pharmaceutical composition comprising a tablet containing 75 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{last}$ of tenofovir alafenamide in fed patients of from about 150 and 260 h·ng/mL, e.g., about 210 h·ng/mL.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{last}$ of the compound of Formula I of from about from about 81700 h·ng/mL to about 140000 h·ng/mL, regardless of whether the subject was fed or fasted.

In certain specific embodiments, a pharmaceutical composition comprising a tablet containing 50 mg of the compound of Formula I or a pharmaceutically acceptable salt thereof. 200 mg emtricitabine or a pharmaceutically acceptable salt thereof, and 25 mg tenofovir alafenamide or a pharmaceutically acceptable salt thereof provide a plasma AUC last of the compound of Formula I in fasted patients of from about 81700 h·ng/mL to about 140000 h·ng/mL, from about 87000 h·ng/mL to about 131000 h·ng/mL, from about 92000 h·ng/mL to about 130000 h·ng/mL, from about 98100 h·ng/mL to about 120000 h·ng/mL, from about 104000 h·ng/mL to about 115000 h·ng/mL.

In particular embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{last}$ of the compound of Formula I in fed patients of from about 100000 h·ng/mL to about 200000 ng/mL, or from about 108000 h·ng/mL to about 170000 ng/mL, or from about 122000 h·ng/mL to about 150000 ng/mL, or from about 128000 h·ng/mL to about 142000 ng/mL.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{last}$ of emtricitabine of from about from about 7500 h·ng/mL to about 15000 h·ng/mL, regardless of whether the subject was fed or fasted.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{last}$ of the emtricitabine in fasted patients of from about 8000 h·ng/mL to about 13400 h·ng/mL, from about 8500 h·ng/mL to about 12800 h·ng/mL, from about 9000 h·ng/mL to about 12300 h·ng/mL, from about 9500 h·ng/mL to about 11000 h·ng/mL, from about 10000 h·ng/mL to about 11200 h·ng/mL.

In particular embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{last}$ of emtricitabine in fed patients of from about 7500 h·ng/mL to about 15000 ng/mL, or from about 8000 h·ng/mL to about 14000 ng/mL, or from about 9000 h·ng/mL to about 12000 ng/mL, or from about 9700 h·ng/mL to about 11300 ng/mL.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{last}$ of tenofovir alafenamide of from about from about 165 h·ng/mL to about 400 h·ng/mL, regardless of whether the subject was fed or fasted.

In certain specific embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{last}$ of the tenofovir alafenamide in fasted patients of from about 165 h·ng/mL to about 390 h·ng/mL, from about 186 h·ng/mL to about 227 h·ng/mL, from about 196 h·ng/mL to about 217 h·ng/mL.

In particular embodiments, a pharmaceutical composition comprising a tablet containing 50 mg of the compound of Formula I or a pharmaceutically acceptable salt thereof, 200 mg emtricitabine or a pharmaceutically acceptable salt thereof, and 25 mg tenofovir alafenamide or a pharmaceutically acceptable salt thereof provide a plasma $AUC_{last}$ of tenofovir alafenamide in fed patients of from about 200 h·ng/mL to about 400 ng/mL, or from about 230 h·ng/mL to about 390 ng/mL, or from about 260 h·ng/mL to about 345 ng/mL, or from about 275 h·ng/mL to about 330 ng/mL.

$C_{last}$ $C_{last}$ is the last observed quantifiable plasma/serum concentration of the drug.

$C_{max}$, $C_{last}$ $AUC_{inf}$, and $AUC_{last}$ are standard pharmacokinetic parameters that can be estimated manually or by using modelling software well known in the art, such as the Pharsight WinNonlin package using a non-compartmental model. The general basis for calculation of these quantities is well-known (e.g., see Rowland & Tozer (2010) *Clinical Pharmacokinetics and Pharmacodynamics: Concepts and Applications* ISBN 978-0781750097, or Jambhekar & Breen (2012) Basic Pharmacokinetics ISBN 978-0853699804). Typically the parameters will be assessed as the average (e.g., geometric or arithmetic mean) from within a group of at least 12 (and normally between 24 and 36) healthy human adults. Parameters should be measured in accordance with standards and practices which would be acceptable to a pharmaceutical regulatory agency such as FDA, EMA, MHLW, or WHO. The values may be based on measurements taken at appropriate intervals following the time of tablet ingestion, such as every hour, or at increasingly sparse sampling intervals, such as 1, 3, 5, 7, 9, 11, 13, 15, 20, and 24 hours after ingestion. They can be assessed either following a single-dose of drug or at steady state, but will typically be assessed following a single-dose.

It is well known in the bioavailability and bioequivalence arts how to determine whether any particular tablet meets regulatory requirements for equivalent bioavailability and pharmacokinetic bioequivalence e.g., see: Niazi (2014) *Handbook of Bioequivalence Testing,* 2nd Edition, ISBN 978-1482226379*; Guidance for Industry Bioavailability and Bioequivalence Studies for Orally Administered Drug Products—General Considerations* FDA March 2003; and *Guideline On The Investigation Of Bioequivalence*, EMEA 2010 CPMP/EWP/QWP/1401/98 Rev. 1/Corr**. To ensure statistical power a study to measure the $C_{max}$, $AUC_{last}$ and $AUC_{inf}$ values will be performed in multiple subjects e.g., in a group of at least 12 (and normally between 24 and 36) healthy human adults.

Because determining the $C_{max}$, $AUC_{last}$ and $AUC_{inf}$ values is necessarily destructive these parameters will not be determined directly for the dosage form (in particular the tablet) in question, but rather for a dosage form made by the same manufacturing process with the same components. Thus a batch of a dosage form (e.g., tablets) can be made by a particular process, and the 90% confidence interval of $C_{max}$, $AUC_{last}$ and AUCH will be assessed on a sample of those tablets. If these values meet the 80-125% requirement noted above then tablets made by the manufacturing process in question are tablets of the present invention.

A fixed dose combination tablet is provided comprising (a) the compound of Formula I or a pharmaceutically acceptable salt thereof (e.g. Formula II), (b) tenofovir alafenamide or a pharmaceutically acceptable salt thereof, and (c) emtricitabine or a pharmaceutically acceptable salt thereof.

In an embodiment, a multilayer tablet is provided, comprising (a) the compound of Formula I or a pharmaceutically acceptable salt thereof (e.g. Formula II), (b) tenofovir alafenamide or a pharmaceutically acceptable salt thereof, and (c) emtricitabine or a pharmaceutically acceptable salt thereof.

In an embodiment, the multilayer tablet disclosed herein comprises (a) a first layer comprising the compound of Formula I or a pharmaceutically acceptable salt thereof, (b) a second layer containing tenofovir alafenamide or a pharmaceutically acceptable salt thereof, and (c) further comprises emtricitabine or a pharmaceutically acceptable salt thereof.

In an embodiment of the multilayer tablet disclosed herein, (a) the first layer is substantially free of tenofovir alafenamide or a pharmaceutically acceptable salt thereof, and/or (b) the second layer is substantially free of the compound of Formula I or a pharmaceutically acceptable salt thereof.

In an embodiment of the multilayer tablet disclosed herein, (a) the first layer is substantially free of emtricitabine or a pharmaceutically acceptable salt thereof, and/or (b) the second layer is substantially free of the compound of Formula I or a pharmaceutically acceptable salt thereof.

In an embodiment of the multilayer tablet disclosed herein, (a) the first layer is substantially free of emtricitabine or a pharmaceutically acceptable salt thereof and tenofovir alafenamide or a pharmaceutically acceptable salt thereof, and/or (b) the second layer is substantially free of the compound of Formula I or a pharmaceutically acceptable salt thereof.

In an embodiment, the multilayer tablet disclosed herein comprises (a) a first layer comprising the compound of Formula I or a pharmaceutically acceptable salt thereof. (b) a second layer containing emtricitabine or a pharmaceutically acceptable salt thereof, and (c) further comprises tenofovir alafenamide or a pharmaceutically acceptable salt thereof.

In an embodiment of the multilayer tablet disclosed herein, (a) the first layer is substantially free of emtricitabine or a pharmaceutically acceptable salt thereof, and/or (b) the second layer is substantially free of the compound of Formula I or a pharmaceutically acceptable salt thereof.

In an embodiment of the multilayer tablet disclosed herein, (a) the first layer comprises the compound of Formula I or a pharmaceutically acceptable salt thereof and is substantially free of tenofovir alafenamide or a pharmaceutically acceptable salt thereof, and (b) the second layer comprises tenofovir alafenamide or a pharmaceutically acceptable salt thereof and emtricitabine or a pharmaceutically acceptable salt thereof and is substantially free of the compound of Formula I or a pharmaceutically acceptable salt thereof.

In an embodiment of the multilayer tablet disclosed herein, the first layer is substantially free of emtricitabine.

In one embodiment, the multilayer tablet disclosed herein comprises 50±6 mg of the compound of Formula I. In one embodiment, the multilayer tablet disclosed herein comprises 200±20 mg of emtricitabine. In one embodiment, the multilayer tablet disclosed herein comprises 25±3 mg of tenofovir alafenamide.

In one embodiment, the multilayer tablet disclosed herein comprises 75±6 mg of the compound of Formula I. In one embodiment, the multilayer tablet disclosed herein comprises 200±20 mg of emtricitabine. In one embodiment, the multilayer tablet disclosed herein comprises 25±3 mg of tenofovir alafenamide.

In one embodiment, the multilayer tablet disclosed herein comprises 52±6 mg of the compound of Formula II. In one embodiment, the multilayer tablet disclosed herein comprises 200±20 mg of emtricitabine. In one embodiment, the multilayer tablet disclosed herein comprises 28±3 mg of tenofovir alafenamide hemifumarate.

In one embodiment, the multilayer tablet disclosed herein comprises 78±6 mg of the compound of Formula II. In one embodiment, the multilayer tablet disclosed herein comprises 200±20 mg of emtricitabine. In one embodiment, the multilayer tablet disclosed herein comprises 28±3 mg of tenofovir alafenamide hemifumarate.

In one embodiment, a first layer of the multilayer tablet disclosed herein comprises one or more excipients, for example one or more diluents, disintegrants, binders, or lubricants.

In one embodiment, a first layer of the multilayer tablet comprises croscarmellose sodium. In one embodiment, a first layer of the multilayer tablet comprises croscarmellose sodium, microcrystalline cellulose, and magnesium stearate.

In one embodiment a tablet is provided wherein less than about 25 weight percent of a first layer is the compound of Formula I or a pharmaceutically acceptable salt thereof. In one embodiment a tablet is provided wherein less than about 20 weight percent of a first layer is the compound of Formula I or a pharmaceutically acceptable salt thereof. In one embodiment a tablet is provided wherein less than about 16 weight percent of a first layer is the compound of Formula I or a pharmaceutically acceptable salt thereof. In one embodiment a tablet is provided wherein about 5 to about 20 weight percent, or about 10 to about 18 weight percent, or about 14 to about 18 weight percent of a first layer is the compound of Formula I or a pharmaceutically acceptable salt thereof. In one embodiment a tablet is provided wherein about 16 weight percent of a first layer is the compound of Formula I or a pharmaceutically acceptable salt thereof.

In one embodiment a tablet is provided wherein the first layer comprises 52±2.8 mg of the compound of Formula II and wherein the total weight of the first layer is at least about 290 mg.

In one embodiment a tablet is provided wherein the first layer comprises 52±2.8 mg of the compound of Formula II and wherein the total weight of the first layer is at least about 300 mg.

In one embodiment a tablet is provided wherein the first layer comprises 52±2.8 mg of the compound of Formula II and wherein the total weight of the first layer is at least about 310 mg.

In one embodiment a tablet is provided wherein the first layer comprises 52±2.8 mg of the compound of Formula II and wherein the total weight of the first layer is at least about 320 mg.

In one embodiment a tablet is provided wherein the first layer comprises 52±2.8 mg of the compound of Formula II and wherein the total weight of the first layer is at least about 330 mg.

In one embodiment a tablet is provided wherein the first layer comprises 52±2.8 mg of the compound of Formula II and wherein the total weight of the first layer is at least about 340 mg.

In one embodiment a tablet is provided wherein the first layer comprises 52±2.8 mg of the compound of Formula II and wherein the total weight of the first layer is at least about 350 mg.

In one embodiment a tablet is provided wherein the first layer comprises 52±2.8 mg of the compound of Formula II and wherein the total weight of the first layer is at least about 360 mg.

In one embodiment a tablet is provided wherein the first layer comprises 52±2.8 mg of the compound of Formula II and wherein the total weight of the first layer is at least about 290 mg and is less than about 360 mg.

In one embodiment a tablet is provided wherein the first layer comprises 52±2.8 mg of the compound of Formula II and wherein the total weight of the first layer is at least about 300 mg and is less than about 350 mg.

In one embodiment a tablet is provided wherein the first layer comprises 52±2.8 mg of the compound of Formula II and wherein the total weight of the first layer is at least about 310 mg and is less than about 330 mg.

In one embodiment, the first layer of the multilayer tablet has a total weight of 323±75 mg, or 323±25 mg, or 323±10 mg, or 323 mg.

In one embodiment, the first layer of the multilayer tablet comprises:

| Ingredient | Mass (mg) |
|---|---|
| The compound of Formula I or a salt thereof | 40-60 |
| Microcrystalline cellulose | 200-400 |
| Croscarmellose sodium | 1-40 |
| Magnesium stearate | 1-10 |

In one embodiment, the first layer of the multilayer tablet comprises:

| Ingredient | Mass (mg) |
|---|---|
| the compound of Formula II | 30-60 |
| Microcrystalline cellulose | 200-400 |
| Croscarmellose sodium | 1-40 |
| Magnesium stearate | 2-8 |

In one embodiment, the first layer of the multilayer tablet comprises

| Ingredient | Mass (mg) |
|---|---|
| the compound of Formula II | 50 ± 6 |
| Microcrystalline cellulose | 250 ± 20 |
| Croscarmellose sodium | 20 ± 5 |
| Magnesium stearate | 5 ± 1.5 |

In one embodiment, the first layer of the multilayer tablet consists of:

| Ingredient | Mass (mg) |
|---|---|
| the compound of Formula II | 52 ± 5.6 |
| Microcrystalline cellulose | 246 ± 10 |
| Croscarmellose sodium | 19 ± 2.5 |
| Magnesium stearate | 5 ± 0.75 |

In one embodiment, the first layer of the multilayer tablet consists of:

| Ingredient | Mass (mg) |
|---|---|
| the compound of Formula II | 52 ± 2.8 |
| Microcrystalline cellulose | 246 ± 5 |
| Croscarmellose sodium | 19 ± 1.75 |
| Magnesium stearate | 5 ± 0.5 |

In one embodiment, the first layer of the multilayer tablet consists of:

| Ingredient | Mass (mg) |
|---|---|
| the compound of Formula II | 52.5 |
| Microcrystalline cellulose | 246.3 |
| Croscarmellose sodium | 19.4 |
| Magnesium stearate | 4.9 |

In one embodiment, the first layer of the multilayer tablet includes:

| Ingredient | Mass (mg) |
|---|---|
| Intergranular | |
| the compound of Formula I or a pharmaceutically acceptable salt thereof | 52.5 ± 1.6 |
| Microcrystalline cellulose | 214 ± 7.3 |
| Croscarmellose sodium | 19 ± 0.6 |
| Magnesium stearate | 2.4 ± 0.5 |
| Extragranular | |
| Microcrystalline cellulose | 32 ± 1 |
| Magnesium stearate | 2.4 ± 0.5 |
| Total layer weight | 323 |

In one embodiment, the first layer of the multilayer tablet includes:

| Ingredient | Mass (mg) |
|---|---|
| Intergranular | |
| the compound of Formula II | 52.5 ± 1.6 |
| Microcrystalline cellulose | 214 ± 7.3 |
| Croscarmellose sodium | 19 ± 0.6 |
| Magnesium stearate | 2.4 ± 0.5 |
| Extragranular | |
| Microcrystalline cellulose | 32 ± 1 |
| Magnesium stearate | 2.4 ± 0.5 |
| Total layer weight | 323 |

In one embodiment, the first layer of the multilayer tablet consists of:

| Ingredient | Mass (mg) |
|---|---|
| Intergranular | |
| the compound of Formula II | 52.5 ± 1.6 |
| Microcrystalline cellulose | 214 ± 6.4 |
| Croscarmellose sodium | 19.4 ± 0.6 |
| Magnesium stearate | 2.45 ± 0.5 |
| Extragranular | |
| Microcrystalline cellulose | 32.3 ± 1 |
| Magnesium stearate | 2.45 ± 0.5 |
| Total layer weight | 323 |

In one embodiment, the first layer of the multilayer tablet includes

| Ingredient | Mass (mg) |
|---|---|
| Intergranular | |
| the compound of Formula I, or a pharmaceutically acceptable salt therof | 52.5 ± 1.6 |
| Microcrystalline cellulose | 214 ± 6.4 |
| Croscarmellose sodium | 19.4 ± 0.6 |
| Magnesium stearate | 2.43 ± 0.5 |
| Extragranular | |
| Microcrystalline cellulose | 32.3 ± 1 |
| Magnesium stearate | 2.43 ± 0.5 |
| Total layer weight | 323 |

In one embodiment, the first layer of the multilayer tablet includes:

| Ingredient | Mass (mg) |
|---|---|
| Intergranular | |
| the compound of Formula II | 52.5 ± 1.6 |
| Microcrystalline cellulose | 214 ± 6.4 |
| Croscarmellose sodium | 19.4 ± 0.6 |
| Magnesium stearate | 2.43 ± 0.5 |
| Extragranular | |
| Microcrystalline cellulose | 32.3 ± 1 |
| Magnesium stearate | 2.43 ± 0.5 |
| Total layer weight | 323 |

In one embodiment a tablet is provided wherein less than about 30 weight percent of the first layer is the compound of Formula I or a pharmaceutically acceptable salt thereof. In one embodiment a tablet is provided wherein less than about 25 weight percent of the first layer is the compound of Formula I or a pharmaceutically acceptable salt thereof. In one embodiment a tablet is provided wherein less than about 22 weight percent of the first layer is the compound of Formula I or a pharmaceutically acceptable salt thereof. In one embodiment a tablet is provided wherein about 15 to about 27 weight percent, or about 17 to about 25 weight percent, or about 19 to about 23 weight percent of the first layer is the compound of Formula I or a pharmaceutically acceptable salt thereof. In one embodiment a tablet is provided wherein about 21 weight percent of the first layer is the compound of Formula I or a pharmaceutically acceptable salt thereof.

In one embodiment a tablet is provided wherein the first layer comprises 78±2.8 mg of the compound of Formula II and wherein the total weight of the first layer is at least about 320 mg.

In one embodiment a tablet is provided wherein the first layer comprises 78±2.8 mg of the compound of Formula II and wherein the total weight of the first layer is at least about 330 mg.

In one embodiment a tablet is provided wherein the first layer comprises 78±2.8 mg of the compound of Formula II and wherein the total weight of the first layer is at least about 340 mg.

In one embodiment a tablet is provided wherein the first layer comprises 78±2.8 mg of the compound of Formula II and wherein the total weight of the first layer is at least about 350 mg.

In one embodiment a tablet is provided wherein the first layer comprises 78±2.8 mg of the compound of Formula II and wherein the total weight of the first layer is at least about 360 mg.

In one embodiment a tablet is provided wherein the first layer comprises 78±2.8 mg of the compound of Formula II and wherein the total weight of the first layer is at least about 370 mg.

In one embodiment a tablet is provided wherein the first layer comprises 78±2.8 mg of the compound of Formula II and wherein the total weight of the first layer is at least about 380 mg.

In one embodiment a tablet is provided wherein the first layer comprises 78±2.8 mg of the compound of Formula II and wherein the total weight of the first layer is at least about 390 mg.

In one embodiment a tablet is provided wherein the first layer comprises 78±2.8 mg of the compound of Formula II and wherein the total weight of the first layer is at least about 320 mg and is less than about 390 mg.

In one embodiment a tablet is provided wherein the first layer comprises 78±2.8 mg of the compound of Formula II and wherein the total weight of the first layer is at least about 330 mg and is less than about 380 mg.

In one embodiment a tablet is provided wherein the first layer comprises 78±2.8 mg of the compound of Formula II and wherein the total weight of the first layer is at least about 350 mg and is less than about 360 mg.

In one embodiment, the first layer of the multilayer tablet has a total weight of 353±75 mg, or 353±25 mg, or 353±10 mg, or 353 mg.

In one embodiment, the first layer of the multilayer tablet comprises:

| Ingredient | Mass (mg) |
|---|---|
| The compound of Formula I or a salt thereof | 40-85 |
| Microcrystalline cellulose | 200-400 |
| Croscarmellose sodium | 1-40 |
| Magnesium stearate | 1-10 |

In one embodiment, the first layer of the multilayer tablet comprises:

| Ingredient | Mass (mg) |
|---|---|
| The compound of Formula II | 30-90 |
| Microcrystalline cellulose | 200-400 |
| Croscarmellose sodium | 1-40 |
| Magnesium stearate | 2-8 |

In one embodiment, the first layer of the multilayer tablet comprises

| Ingredient | Mass (mg) |
|---|---|
| The compound of Formula II | 80 ± 6 |
| Microcrystalline cellulose | 250 ± 20 |
| Croscarmellose sodium | 20 ± 5 |
| Magnesium stearate | 5 ± 1.5 |

In one embodiment, the first layer of the multilayer tablet consists of:

| Ingredient | Mass (mg) |
|---|---|
| The compound of Formula II | 78 ± 5.6 |
| Microcrystalline cellulose | 250 ± 10 |
| Croscarmellose sodium | 20 ± 2.5 |
| Magnesium stearate | 5 ± 0.75 |

-continued

In one embodiment, the first layer of the multilayer tablet consists of:

| Ingredient | Mass (mg) |
|---|---|
| the compound of Formula II | 78 ± 2.8 |
| Microcrystalline cellulose | 247 ± 5 |
| Croscarmellose sodium | 21 ± 1.75 |
| Magnesium stearate | 5 ± 0.5 |

In one embodiment, the first layer of the multilayer tablet consists of:

| Ingredient | Mass (mg) |
|---|---|
| the compound of Formula II | 78.7 |
| Microcrystalline cellulose | 247.8 |
| Croscarmellose sodium | 21.2 |
| Magnesium stearate | 5.3 |

In one embodiment, the first layer of the multilayer tablet consists of:

| Ingredient | Mass (mg) |
|---|---|
| Intergranular | |
| the compound of Formula II | 78.7 |
| Microcrystalline cellulose | 212.5 |
| Croscarmellose sodium | 21.2 |
| Magnesium stearate | 2.65 |
| Extragranular | |
| Microcrystalline cellulose | 35.3 |
| Magnesium stearate | 2.65 |
| Total layer weight | 353 |

In one embodiment, the second layer of the multilayer tablet does not comprise lactose. In one embodiment, the second layer of the multilayer tablet does not comprise starch. In one embodiment, the second layer of the multilayer tablet comprises neither lactose nor starch.

In one embodiment, the second layer of the multilayer tablet comprises one or more excipients, for example, one or more diluents, disintegrants, binders, or lubricants.

In one embodiment, the second layer of the multilayer tablet comprises microcrystalline cellulose and croscarmellose sodium.

In one embodiment, the second layer of the multilayer tablet comprises microcrystalline cellulose, croscarmellose sodium and magnesium stearate.

In one embodiment, the second layer of the multilayer tablet comprises 20-40 mg of croscarmellose sodium. In one embodiment, the second layer of the multilayer tablet comprises 105-125 mg of microcrystalline cellulose. In one embodiment, the second layer of the multilayer tablet comprises 1-8 mg of magnesium stearate.

In one embodiment, the second layer of the multilayer tablet does not comprise lactose. In one embodiment, the second layer of the multilayer tablet does not comprise starch. In one embodiment, the second layer of the multilayer tablet comprises neither lactose nor starch.

In one embodiment, the second layer of the multilayer tablet has a total weight of less than 600 mg, or less than 500 mg, or less than 400 mg, or less than 380 mg. In one embodiment, the second layer of the multilayer tablet has a total weight of 377 mg±50 mg or 377 mg±25 mg, or 377 mg±5 mg, or 377 mg.

In one embodiment, over 50% by weight of the second layer of the multilayer tablet is emtricitabine or a salt thereof and tenofovir alafenamide or a salt thereof. In one embodiment, over 55% by weight of the second layer of the multilayer tablet is emtricitabine or a salt thereof and tenofovir alafenamide or a salt thereof. In one embodiment, over 60% by weight of the second layer of the multilayer tablet is emtricitabine or a salt thereof and tenofovir alafenamide or a salt thereof. In one embodiment, about 55% to about 65% by weight of the second layer of the multilayer tablet is emtricitabine or a salt thereof and tenofovir alafenamide or a salt thereof. In one embodiment, over 60% by weight of the second layer of the multilayer tablet is emtricitabine and tenofovir alafenamide hemifumarate. In one embodiment, about 55% to about 65% by weight of the second layer of the multilayer tablet is emtricitabine and tenofovir alafenamide hemifumarate.

In one embodiment, the second layer of the multilayer tablet contains less than 250 mg of excipients, for example less than 200 mg, or less than 150 mg.

In one embodiment, at least 50% by weight of the second layer of the multilayer tablet is emtricitabine. In one embodiment, at least 53% by weight of the second layer of the multilayer tablet is emtricitabine. In one embodiment, about 45% to about 65% by weight of the second layer of the multilayer tablet is emtricitabine. In one embodiment, about 50% to about 60% by weight of the second layer of the multilayer tablet is emtricitabine. In one embodiment, about 51% to about 53% by weight of the second layer of the multilayer tablet is emtricitabine.

In one embodiment, at least 4% by weight of the second layer of the multilayer tablet is tenofovir alafenamide hemifumarate. In one embodiment, at least 6% by weight of the second layer of the multilayer tablet is tenofovir alafenamide hemifumarate. In one embodiment, at least 7% by weight of the second layer of the multilayer tablet is tenofovir alafenamide hemifumarate. In one embodiment, about 5% to about 10% by weight of the second layer of the multilayer tablet is tenofovir alafenamide hemifumarate. In one embodiment, about 6% to about 9% by weight of the second layer of the multilayer tablet is tenofovir alafenamide hemifumarate. In one embodiment, about 7% to about 8% by weight of the second layer of the multilayer tablet is tenofovir alafenamide hemifumarate. In one embodiment, about 7% by weight of the second layer of the multilayer tablet is tenofovir alafenamide hemifumarate.

In one embodiment, less than 20% by weight of the second layer of the multilayer tablet is croscarmellose sodium. In one embodiment, less than 10% by weight of the second layer of the multilayer tablet is croscarmellose sodium. In one embodiment, about 5% to about 10% by weight of the second layer of the multilayer tablet is croscannellose sodium. In certain embodiments, the use of about 5 to 7% (e.g., about 6%) croscarmellose sodium by weight of the second layer may provide enhanced dissolution of the compound of Formula I or a pharmaceutically acceptable salt thereof, relative to other disintegrants e.g., polyvinylpyrrolidone (crospovidone). In certain embodiments, the use of about 5 to 10% croscarmellose sodium by weight of the second layer may provide enhanced dissolution of the compound of Formula I or a pharmaceutically acceptable salt thereof, relative to other disintegrants e.g., polyvinylpyrrolidone (crospovidone).

In one embodiment, less than 50% by weight of the second layer of the multilayer tablet is microcrystalline cellulose. In one embodiment, less than 40% by weight of the second layer of the multilayer tablet is microcrystalline cellulose. In one embodiment, less than 31% by weight of the second layer of the multilayer tablet is microcrystalline cellulose.

In one embodiment, less than 5% by weight of the second layer of the multilayer tablet is magnesium stearate. In one embodiment, less than 3% by weight of the second layer of the multilayer tablet is magnesium stearate. In one embodiment, less than 2% by weight of the second layer of the multilayer tablet is magnesium stearate. In one embodiment, about 0.5% to about 1.5% by weight of the second layer of the multilayer tablet is magnesium stearate. In certain embodiments, the use of about 1% to about 2% (e.g., about 1.5%) magnesium stearate by weight of the second layer may provide enhanced dissolution of the compound of Formula I or a pharmaceutically acceptable salt thereof, relative to other lubricants e.g., sodium stearyl fumarate.

In one embodiment, the total weight of the second layer is less than 150% of the total weight of the first layer. In one embodiment, the total weight of the second layer is less than 125% of the total weight of the first layer. In one embodiment, the total weight of the second layer is less than 116% of the total weight of the first layer. In one embodiment, the total weight of the second layer is less than 106% of the total weight of the first layer.

In one embodiment, the second layer of the multilayer tablet comprises:

| Ingredient | Mass (mg) |
|---|---|
| Emtricitabine or a salt thereof | 150-250 |
| Tenofovir alafenamide or a salt thereof | 20-35 |
| Microcrystalline cellulose | 90-130 |
| Croscarmellose sodium | 20-35 |
| Magnesium stearate | 1-7 |

In one embodiment, the second layer of the multilayer tablet comprises:

| Ingredient | Mass (mg) |
|---|---|
| Emtricitabine | 170-230 |
| Tenofovir alafenamide hemifumarate | 22-32 |
| Microcrystalline cellulose | 100-120 |
| Croscarmellose sodium | 20-35 |
| Magnesium stearate | 1-7 |

In one embodiment, the second layer of the multilayer tablet consists of:

| Ingredient | Mass (mg) |
|---|---|
| Emtricitabine | 200 ± 20 |
| Tenofovir alafenamide hemifumarate | 28 ± 3 |
| Microcrystalline cellulose | 113 ± 9 |
| Croscarmellose sodium | 30 ± 3 |
| Magnesium stearate | 5.6 ± 1.1 |

In one embodiment, the second layer of the multilayer tablet consists of:

| Ingredient | Mass (mg) |
|---|---|
| Emtricitabine | 200 ± 10 |
| Tenofovir alafenamide hemifumarate | 28 ± 1.4 |
| Microcrystalline cellulose | 113 ± 4 |
| Croscarmellose sodium | 30 ± 1.4 |
| Magnesium stearate | 5.6 ± 0.5 |

In one embodiment, the second layer of the multilayer tablet consists of:

| Ingredient | Mass (mg) |
|---|---|
| Emtricitabine | 200 |
| Tenofovir alafenamide hemifumarate | 28.1 |
| Microcrystalline cellulose | 113.2 |
| Croscarmellose sodium | 30.2 |
| Magnesium stearate | 5.7 |

In one embodiment, the second layer of the multilayer tablet consists of:

| Ingredient | Mass (mg) |
|---|---|
| Intergranular | |
| Emtricitabine | 200.00 |
| Tenofovir alafenamide hemifumarate | 28.1 |
| Microcrystalline cellulose | 113.2 |
| Croscarmellose sodium | 30.2 |
| Magnesium stearate | 2.85 |
| Extragranular | |
| Magnesium stearate | 2.85 |
| Total layer weight | 377 |

In one embodiment, the second layer of the multilayer tablet includes.

| Ingredient | Mass (mg) |
|---|---|
| Emtricitabine | 200 ± 20 |
| Tenofovir alafenamide | 25 ± 3 |
| Microcrystalline cellulose | 115 ± 9 |
| Croscarmellose sodium | 30 ± 3 |
| Magnesium stearate | 3.8 ± 1.1 |

In one embodiment, the second layer of the multilayer tablet includes:

| Ingredient | Mass (mg) |
|---|---|
| Emtricitabine | 200 ± 20 |
| Tenofovir alafenamide hemifumarate | 28 ± 3 |
| Microcrystalline cellulose | 115 ± 9 |
| Croscarmellose sodium | 30 ± 3 |
| Magnesium stearate | 3.8 ± 1.1 |

In one embodiment, the second layer of the multilayer tablet includes:

| Ingredient | Mass (mg) |
|---|---|
| Emtricitabine | 200 ± 10 |
| Tenofovir alafenamide hemifumarate | 28 ± 1.4 |
| Microcrystalline cellulose | 115 ± 4 |
| Croscarmellose sodium | 30 ± 1.4 |
| Magnesium stearate | 3.8 ± 0.5 |

In one embodiment, the second layer of the multilayer tablet includes:

| Ingredient | Mass (mg) |
|---|---|
| Emtricitabine | 200 |
| Tenofovir alafenamide hemifumarate | 28.1 |
| Microcrystalline cellulose | 115 |
| Croscarmellose sodium | 30.2 |
| Magnesium stearate | 3.8 |

In one embodiment, the second layer of the multilayer tablet includes:

| Ingredient | Mass (mg) |
|---|---|
| Intergranular | |
| Emtricitabine | 200 |
| Tenofovir alafenamide hemifumarate | 28 |
| Microcrystalline cellulose | 115 |
| Croscarmellose sodium | 30.2 |
| Magnesium stearate | 1.9 |
| Extragranular | |
| Magnesium stearate | 1.9 |
| Total layer weight | 377 |

In one embodiment, the second layer of the multilayer tablet includes:

| Ingredient | Mass (mg) |
|---|---|
| Emtricitabine | 200 |
| Tenofovir alafenamide hemifumarate | 28 |
| Microcrystalline cellulose | 113.2 |
| Croscarmellose sodium | 30.2 |
| Magnesium stearate | 5.7 |

In one embodiment, the second layer of the multilayer tablet includes:

| Ingredient | Mass (mg) |
|---|---|
| Emtricitabine | 200 |
| Tenofovir alafenamide hemifumarate | 28 |
| Microcrystalline cellulose | 115 |
| Croscarmellose sodium | 30.2 |
| Magnesium stearate | 3.8 |

In one embodiment, the second layer of the multilayer tablet includes:

| Ingredient | Mass (mg) |
|---|---|
| Intergranular | |
| Emtricitabine | 200 |
| Tenofovir alafenamide hemifumarate | 28 |
| Microcrystalline cellulose | 113.2 |

-continued

| Ingredient | Mass (mg) |
|---|---|
| Croscarmellose sodium | 30.2 |
| Magnesium stearate | 2.85 |
| Extragranular | |
| Magnesium stearate | 2.85 |
| Total layer weight | 377 |

In one embodiment of the multilayer tablet formulations disclosed herein, the first layer is in contact with the second layer.

In one embodiment, the first layer is produced first, followed be the second layer. That is, in one embodiment, the first layer is prepared and pressed into a first layer, followed by the second layer being prepared and being pressed with the first layer into a multilayer tablet. In one embodiment, the second layer is produced first, followed be the first laver. That is, in one embodiment, the second layer is prepared and pressed into a second layer, followed by the first layer being prepared and being pressed with the second layer into a multilayer tablet.

As used herein, when describing the multilayer tablets disclosed herein, the terms “first layer” and “second layer” are not intended to indicate the method by which the tablets are produced, in particular the order in which the layers are obtained.

In certain embodiments, the multilayer tablet further comprises additional layers. In certain embodiments, the additional layer or layers are located between the first and second layers. In certain embodiments, the additional layer or layers are located on either side of the first and/or second layer, such that they are an outside layer of the table and/or are disposed between the first and/or second layer and a coating layer. In some embodiments, the additional layer or layers encapsulate the first and second layers.

In one embodiment, the multilayer tablet further comprises a third layer that is between and that separates the first layer and the second layer. In one embodiment, the third layer of the multilayer tablet comprises lactose monohydrate, or microcrystalline cellulose, or a mixture thereof.

In one embodiment, the multilayer tablet further comprises a film coating. In one embodiment, the multilayer tablet further comprises about 14 mg to about 28 mg of a film coating. In one embodiment, the multilayer tablet further comprises about 19 mg to about 23 mg of a film coating. In one embodiment, the multilayer tablet further comprises about 21 mg of a film coating. In one embodiment the film coating comprises polyvinyl alcohol, polyethylene glycol, tale, titanium dioxide, and black iron oxide. In one embodiment the film coating consists of 21±7 mg of Opadry II Brown 85F165072. In one embodiment the film coating consists of 21±7 mg of Opadry II Yellow 85F92259.

In one embodiment, the multilayer tablet further includes a film coating. In one embodiment, the multilayer tablet further comprises about 1.9% to about 3.9% w/w of a film coating. In one embodiment, the multilayer tablet further comprises about 2.5% to about 3.5% w/w of a film coating. In one embodiment, the multilayer tablet further comprises about 3% of a film coating. In one embodiment the film coating includes polyvinyl alcohol, polyethylene glycol, tale, titanium dioxide, iron oxide red, and black iron oxide. In one embodiment the film coating includes 36%-40% polyvinyl alcohol, 18%-22% polyethylene glycol. 13%-16% talc, 20%-24% titanium dioxide, 2%-3% iron oxide red, and 0.5%-0.7% black iron oxide.

In one embodiment a tablet is provided comprising about 6.4-8.5% w/w of the compound of Formula II, about 25-32% w/w mg emtricitabine, about 3.5-4.5% w/w mg tenofovir alafenamide hemifumarate, about 46-57% w/w mg microcrystalline cellulose, about 5.9-8.5% w/w mg croscannellose sodium, and about 1.0-2.0% w/w mg magnesium stearate.

In one embodiment a tablet is provided comprising 52±6 mg of the compound of Formula II. 200±20 mg emtricitabine, 28±3 mg tenofovir alafenamide hemifumarate, 360±30 mg Microcrystalline cellulose, 50±8 mg Croscarmellose sodium, and 10.5±3 mg magnesium stearate and wherein the total weight of the tablet is at least about 685 mg.

In one embodiment a tablet is provided comprising 52±6 mg of the compound of Formula II. 200±10 mg emtricitabine. 28±1.5 mg tenofovir alafenamide hemifumarate, 360±15 mg Microcrystalline cellulose. 50±4 mg Croscarmellose sodium, and 10.5±1.5 mg magnesium stearate and wherein the total weight of the tablet is at least about 685 mg and is less than about 715 mg.

In one embodiment a tablet is provided comprising 52±6 mg of the compound of Formula II, 200±20 mg emtricitabine, 28±3 mg Tenofovir alafenamide hemifumarate, 360±30 mg Microcrystalline cellulose, 50±8 mg Croscarmellose sodium, and 8.6±3 mg magnesium stearate and wherein the total weight of the tablet is at least about 685 mg.

In one embodiment a tablet is provided comprising 52±6 mg of the compound of Formula II, 200±10 mg emtricitabine. 28±1.5 mg Tenofovir alafenamide hemifumarate, 360±15 mg Microcrystalline cellulose, 50±4 mg Croscarmellose sodium, and 8.6±1.5 mg magnesium stearate and wherein the total weight of the tablet is at least about 685 mg and is less than about 715 mg.

In one embodiment, the tablet has a total weight of 700±75 mg, or 700±25 mg, or 700±10 mg, or 700 mg. In one embodiment, the tablet is uncoated and has a total weight of about 700±75 mg, or about 700±25 mg, or about 700±10 mg, or about 700 mg. In one embodiment, the tablet has a total weight of about 720±75 mg, or about 720±25 mg, or about 720±10 mg, or about 720 mg, or about 721 mg, or about 722 mg, or about 723 mg, or about 724 mg, or about 725 mg, or about 726 mg, or about 727 mg, or about 728 mg, or about 729 mg, or about 730 mg.

In one embodiment a tablet is provided comprising 80±6 mg of the compound of Formula II, 200±20 mg emtricitabine, 28±3 mg Tenofovir alafenamide hemifumarate, 360±30 mg Microcrystalline cellulose. 50±8 mg Croscarmellose sodium, and 11±3 mg magnesium stearate and wherein the total weight of the tablet is at least about 715 mg.

In one embodiment a tablet is provided comprising 78±2.3 mg of the compound of Formula II, 200±10 mg emtricitabine, 28±1.5 mg Tenofovir alafenamide hemifumarate, 361±15 mg Microcrystalline cellulose, 51±4 mg Croscarmellose sodium, and 11±1.5 mg magnesium stearate and wherein the total weight of the tablet is at least about 715 mg and is less than about 745 mg.

In one embodiment, the tablet has a total weight of 730±75 mg, or 730±25 mg, or 730±10 mg, or 730 mg. In one embodiment, the tablet has a total weight of about 750±75 mg, or about 750±25 mg, or about 750±10 mg, or about 750 mg, or about 751 mg, or about 752 mg, or about 753 mg, or about 754 mg, or about 755 mg.

In one embodiment, a tablet is provided comprising:

| Ingredient | Mass (mg) |
|---|---|
| The compound of Formula II | 52 ± 6 |
| Emtricitabine | 200 ± 20 |
| Tenofovir alafenamide hemifumarate | 28 ± 3 |
| Microcrystalline cellulose | 360 ± 30 |
| Croscarmellose sodium | 50 ± 8 |
| Magnesium stearate | 10.5 ± 3 |

In one embodiment, a tablet is provided comprising:

| Ingredient | Mass (mg) |
|---|---|
| The compound of Formula II | 52.5 ± 3 |
| Emtricitabine | 200 ± 10 |
| Tenofovir alafenamide hemifumarate | 28.1 ± 1.5 |
| Microcrystalline cellulose | 360 ± 15 |
| Croscarmellose sodium | 50 ± 4 |
| Magnesium stearate | 10.5 ± 1.5 |

In one embodiment, a tablet is provided including:

| Ingredient | Mass (mg) |
|---|---|
| The compound of Formula I, or a pharmaceutically acceptable salt thereof | 50 ± 5 |
| Emtricitabine | 200 ± 20 |
| Tenofovir alafenamide, or a pharmaceutically acceptable salt thereof | 25 ± 3 |
| Microcrystalline cellulose | 360 ± 30 |
| Croscarmellose sodium | 50 ± 8 |
| Magnesium stearate | 8.6 ± 3 |

In one embodiment, a tablet is provided including:

| Ingredient | Mass (mg) |
|---|---|
| The compound of Formula I, or a pharmaceutically acceptable salt thereof | 50 ± 2.5 |
| Emtricitabine | 200 ± 10 |
| Tenofovir alafenamide, or a pharmaceutically acceptable salt thereof | 25 ± 1.5 |
| Microcrystalline cellulose | 360 ± 15 |
| Croscarmellose sodium | 50 ± 4 |
| Magnesium stearate | 8.6 ± 1.5 |

In one embodiment, a tablet is provided including:

| Ingredient | Mass (mg) |
|---|---|
| The compound of Formula I, or a pharmaceutically acceptable salt thereof | 52 ± 6 |
| Emtricitabine | 200 ± 20 |
| Tenofovir alafenamide hemifumarate | 28 ± 3 |
| Microcrystalline cellulose | 360 ± 30 |
| Croscarmellose sodium | 50 ± 8 |
| Magnesium stearate | 8.6 ± 3 |

In one embodiment, a tablet is provided including:

| Ingredient | Mass (mg) |
|---|---|
| The compound of Formula II | 52 ± 6 |
| Emtricitabine | 200 ± 20 |
| Tenofovir alafenamide hemifumarate | 28 ± 3 |
| Microcrystalline cellulose | 360 ± 30 |
| Croscarmellose sodium | 50 ± 8 |
| Magnesium stearate | 8.6 ± 3 |

-continued

In one embodiment, a tablet is provided including:

| Ingredient | Mass (mg) |
|---|---|
| The compound of Formula II | 52.5 ± 3 |
| Emtricitabine | 200 ± 10 |
| Tenofovir alafenamide hemifumarate | 28.1 ± 1.5 |
| Microcrystalline cellulose | 360 ± 15 |
| Croscarmellose sodium | 50 ± 4 |
| Magnesium stearate | 8.6 ± 1.5 |

In one embodiment, a tablet is provided comprising a first layer consisting of:

| Ingredient | Mass (mg) |
|---|---|
| The compound of Formula II | 50 ± 6 |
| Microcrystalline cellulose | 250 ± 20 |
| Croscarmellose sodium | 20 ± 5 |
| Magnesium stearate | 5 ± 1.5 |

and a second layer consisting of

| Ingredient | Mass (mg) |
|---|---|
| Emtricitabine | 200 ± 20 |
| Tenofovir alafenamide hemifumarate | 28 ± 3 |
| Microcrystalline cellulose | 113 ± 9 |
| Croscarmellose sodium | 30 ± 3 |
| Magnesium stearate | 5.6 ± 1.1 |

In one embodiment, a tablet is provided comprising a first lay or including:

| Ingredient | Mass (mg) |
|---|---|
| The compound of Formula I, or a pharmaceutically acceptable salt thereof | 50 ± 6 |
| Microcrystalline cellulose | 250 ± 20 |
| Croscarmellose sodium | 20 ± 5 |
| Magnesium stearate | 5 ± 1.5 |

and a second layer including:

| Ingredient | Mass (mg) |
|---|---|
| Emtricitabine | 200 ± 20 |
| Tenofovir alafenamide, or a pharmaceutically acceptable salt thereof | 25 ± 3 |
| Microcrystalline cellulose | 113 ± 9 |
| Croscarmellose sodium | 30 ± 3 |
| Magnesium stearate | 4 ± 1.1 |

In one embodiment, a tablet is provided comprising a first layer including:

| Ingredient | Mass (mg) |
|---|---|
| The compound of Formula I, or a pharmaceutically acceptable salt thereof | 50 ± 6 |
| Microcrystalline cellulose | 250 ± 20 |
| Croscarmellose sodium | 20 ± 5 |
| Magnesium stearate | 5 ± 1.5 |

and a second layer including

| Ingredient | Mass (mg) |
|---|---|
| Emtricitabine | 200 ± 20 |
| Tenofovir alafenamide hemifumarate | 28 ± 3 |
| Microcrystalline cellulose | 113 ± 9 |
| Croscarmellose sodium | 30 ± 3 |
| Magnesium stearate | 4 ± 1.1 |

In one embodiment, a tablet is provided comprising a first layer including:

| Ingredient | Mass (mg) |
|---|---|
| The compound of Formula II | 50 ± 6 |
| Microcrystalline cellulose | 250 ± 20 |
| Croscarmellose sodium | 20 ± 5 |
| Magnesium stearate | 5 ± 1.5 |

and a second layer including.

| Ingredient | Mass (mg) |
|---|---|
| Emtricitabine | 200 ± 20 |
| Tenofovir alafenamide hemifumarate | 28 ± 3 |
| Microcrystalline cellulose | 113 ± 9 |
| Croscarmellose sodium | 30 ± 3 |
| Magnesium stearate | 4 ± 1.1 |

In one embodiment, a tablet is provided comprising a first layer consisting of

| Ingredient | Mass (mg) |
|---|---|
| The compound of Formula II | 52 ± 2.8 |
| Microcrystalline cellulose | 246 ± 5 |
| Croscarmellose sodium | 19 ± 1.75 |
| Magnesium stearate | 5 ± 0.5 |

and a second layer consisting of:

| Ingredient | Mass (mg) |
|---|---|
| Emtricitabine | 200 ± 10 |
| Tenofovir alafenamide hemifumarate | 28 ± 1.4 |
| Microcrystalline cellulose | 113 ± 4 |
| Croscarmellose sodium | 30 ± 1.4 |
| Magnesium stearate | 5.6 ± 0.5 |

In one embodiment, a tablet is provided comprising a first layer including:

| Ingredient | Mass (mg) |
|---|---|
| The compound of Formula I, or a pharmaceutically acceptable salt therof | 50 ± 3 |
| Microcrystalline cellulose | 246 ± 5 |
| Croscarmellose sodium | 19 ± 1.75 |
| Magnesium stearate | 5 ± 0.5 |

and a second layer including:

| Ingredient | Mass (mg) |
|---|---|
| Emtricitabine | 200 ± 10 |
| Tenofovir alafenamide, or a pharmacetuically acceptable salt thereof | 25 ± 3 |
| Microcrystalline cellulose | 113 ± 4 |
| Croscarmellose sodium | 30 ± 1.4 |
| Magnesium stearate | 4 ± 0.5 |

In one embodiment, a tablet is provided comprising a first layer including:

| Ingredient | Mass (mg) |
|---|---|
| The compound of Formula II | 52 ± 2.8 |
| Microcrystalline cellulose | 246 ± 5 |
| Croscarmellose sodium | 19 ± 1.75 |
| Magnesium stearate | 5 ± 0.5 |

and a second layer including:

| Ingredient | Mass (mg) |
|---|---|
| Emtricitabine | 200 ± 10 |
| Tenofovir alafenamide hemifumarate | 28 ± 1.4 |
| Microcrystalline cellulose | 113 ± 4 |
| Croscarmellose sodium | 30 ± 1.4 |
| Magnesium stearate | 4 ± 0.5 |

In one embodiment, a tablet is provided comprising:

| Ingredient | Mass (mg) |
|---|---|
| The compound of Formula II | 80 ± 6 |
| Emtricitabine | 200 ± 20 |
| Tenofovir alafenamide hemifumarate | 28 ± 3 |
| Microcrystalline cellulose | 360 ± 30 |
| Croscarmellose sodium | 50 ± 8 |
| Magnesium stearate | 11 ± 3 |

In one embodiment, a tablet is provided comprising:

| Ingredient | Mass (mg) |
|---|---|
| The compound of Formula II | 78.6 ± 2.3 |
| Emtricitabine | 200 ± 10 |
| Tenofovir alafenamide hemifumarate | 28.1 ± 1.5 |
| Microcrystalline cellulose | 361 ± 15 |
| Croscarmellose sodium | 51 ± 4 |
| Magnesium stearate | 11 ± 1.5 |

In one embodiment, a tablet is provided comprising a first layer consisting of.

| Ingredient | Mass (mg) |
|---|---|
| The compound of Formula II | 80 ± 6 |
| Microcrystalline cellulose | 250 ± 20 |
| Croscarmellose sodium | 20 ± 5 |
| Magnesium stearate | 5 ± 1.5 |

and a second layer consisting of:

| Ingredient | Mass (mg) |
|---|---|
| Emtricitabine | 200 ± 20 |
| Tenofovir alafenamide hemifumarate | 28 ± 3 |
| Microcrystalline cellulose | 113 ± 9 |
| Croscarmellose sodium | 30 ± 3 |
| Magnesium stearate | 5.6 ± 1.1 |

In one embodiment, a tablet is provided comprising a first layer consisting of

| Ingredient | Mass (mg) |
|---|---|
| The compound of Formula II | 78 ± 2.8 |
| Microcrystalline cellulose | 247 ± 5 |
| Croscarmellose sodium | 21 ± 1.75 |
| Magnesium stearate | 5 ± 0.5 |

and a second layer consisting of:

| Ingredient | Mass (mg) |
|---|---|
| Emtricitabine | 200 ± 10 |
| Tenofovir alafenamide hemifumarate | 28 ± 1.4 |
| Microcrystalline cellulose | 113 ± 4 |
| Croscarmellose sodium | 30 ± 1.4 |
| Magnesium stearate | 5.6 ± 0.5 |

In one embodiment, a tablet is provided comprising a first layer including:

| | % w/w (in tablet) |
|---|---|
| The compound of Formula I, or a pharmaceutically acceptable salt thereof | 5-10 |
| Microcrystalline cellulose | 26-44 |
| Croscarmellose sodium | 2-4 |
| Magnesium stearate | 0.5-0.9 |

and a second layer including:

| | % w/w (in tablet) |
|---|---|
| Emtricitabine | 21-36 |
| Tenofovir alafenamide, or a pharmaceutically acceptable salt thereof | 3-5 |
| Microcrystalline cellulose | 12-20 |
| Croscarmellose sodium | 3-6 |
| Magnesium stearate | 0.3-0.7 |

and optionally a film coating.

In one embodiment, a tablet is provided comprising a first layer including:

| | % w/w (in tablet) |
|---|---|
| The compound of Formula II | 5-10 |
| Microcrystalline cellulose | 26-44 |
| Croscarmellose sodium | 2-4 |
| Magnesium stearate | 0.5-0.9 |

and a second layer including:

| | % w/w (in tablet) |
|---|---|
| Emtricitabine | 21-36 |
| Tenofovir alafenamide hemifumarate | 3-5 |
| Microcrystalline cellulose | 12-20 |
| Croscarmellose sodium | 3-6 |
| Magnesium stearate | 0.3-0.7 |

and optionally a film coating.

In one embodiment, a tablet is provided comprising a first layer including:

| | % w/w (in tablet) |
|---|---|
| The compound of Formula I, or a pharmaceutically acceptable salt thereof | 6-9 |
| Microcrystalline cellulose | 30-40 |
| Croscarmellose sodium | 2.4-3.2 |
| Magnesium stearate | 0.6-0.8 |

and a second layer including:

| | % w/w (in tablet) |
|---|---|
| Emtricitabine | 24-33 |
| Tenofovir alafenamide, or a pharmaceutically acceptable salt thereof | 3.4-4.6 |
| Microcrystalline cellulose | 14-19 |
| Croscarmellose sodium | 3.6-4.9 |
| Magnesium stearate | 0.6-0.8 |

and optionally a film coating.

In one embodiment, a tablet is provided comprising a first layer including:

| | % w/w (in tablet) |
|---|---|
| The compound of Formula II | 6-9 |
| Microcrystalline cellulose | 30-40 |
| Croscarmellose sodium | 2.4-3.2 |
| Magnesium stearate | 0.6-0.8 |

and a second layer including:

| | % w/w (in tablet) |
|---|---|
| Emtricitabine | 24-33 |
| Tenofovir alafenamide hemifumarate | 3.4-4.6 |
| Microcrystalline cellulose | 14-19 |
| Croscarmellose sodium | 3.6-4.9 |
| Magnesium stearate | 0.6-0.8 |

and optionally a film coating.

| | % w/w (in tablet) |
|---|---|
| The compound of Formula II | 7-8 |
| Microcrystalline cellulose | 32-37 |
| Croscarmellose sodium | 2.7-2.9 |
| Magnesium stearate | 0.6-0.8 |

and a second layer including.

| | % w/w (in tablet) |
|---|---|
| Emtricitabine | 26-30 |
| Tenofovir alafenamide hemifumarate | 3.7-4.6 |
| Microcrystalline cellulose | 15-17 |
| Croscarmellose sodium | 4.0-4.5 |
| Magnesium stearate | 0.5-0.6 |

and optionally a film coating.

In one embodiment, a tablet is provided comprising a first layer including:

| | % w/w (in tablet) |
|---|---|
| The compound of Formula II | 7-8 |
| Microcrystalline cellulose | 33-36 |
| Croscarmellose sodium | 2.7-2.8 |
| Magnesium stearate | 0.7-0.8 |

and a second layer including

| | % w/w (in tablet) |
|---|---|
| Emtricitabine | 27-29 |
| Tenofovir alafenamide hemifumarate | 3.8-4.2 |
| Microcrystalline cellulose | 16-17 |
| Croscarmellose sodium | 4.1-4.4 |
| Magnesium stearate | 0.5-0.8 |

and optionally a film coating.

| | % w/w (in tablet) |
|---|---|
| The compound of Formula II | 7.5 |
| Microcrystalline cellulose | 35.2 |
| Croscarmellose sodium | 2.8 |
| Magnesium stearate | 0.7 |

and a second layer including:

| | % w/w (in tablet) |
|---|---|
| Emtricitabine | 28.6 |
| Tenofovir alafenamide hemifumarate | 4.0 |
| Microcrystalline cellulose | 16.4 |
| Croscarmellose sodium | 4.3 |
| Magnesium stearate | 0.5 |

and optionally a film coating.

In one embodiment, a tablet is provided comprising a first layer including:

| | % w/w (in tablet) |
|---|---|
| The compound of Formula II | 7.5 |
| Microcrystalline cellulose | 35.2 |
| Croscarmellose sodium | 2.8 |
| Magnesium stearate | 0.7 |

and a second layer including:

| | % w/w (in tablet) |
|---|---|
| Emtricitabine | 28.6 |
| Tenofovir alafenamide hemifumarate | 4.0 |
| Microcrystalline cellulose | 16.2 |
| Croscarmellose sodium | 4.3 |
| Magnesium stearate | 0.8 |

and optionally a film coating.

In one embodiment, a tablet is provided comprising a first layer including:

| | % w/w (in layer) |
|---|---|
| Intergranular | |
| The compound of Formula I, or a pharmaceutically accpetable salt thereof | 11-19 |
| Microcrystalline cellulose | 51-86 |
| Croscarmellose sodium | 4-7 |
| Magnesium stearate | 0.5-0.9 |
| Extragranular | |
| Microcrystalline cellulose | 7-12 |
| Magnesium stearate | 0.5-0.9 |

and a second layer including:

| | % w/w (in layer) |
|---|---|
| Intergranular | |
| Emtricitabine | 39-67 |
| Tenofovir alafenamide, or a pharmaceutically acceptable salt thereof | 5-10 |
| Microcrystalline cellulose | 22-38 |
| Croscarmellose sodium | 6-10 |
| Magnesium stearate | 0.3-0.7 |
| Intergranular | |
| Magnesium stearate | 0.3-0.7 |

and optionally a film coating.

In one embodiment, a tablet is provided comprising a first layer including:

| | % w/w (in layer) |
|---|---|
| Intergranular | |
| The compound of Formula II | 11-19 |
| Microcrystalline cellulose | 51-86 |
| Croscarmellose sodium | 4-7 |
| Magnesium stearate | 0.5-0.9 |
| Extragranular | |
| Microcrystalline cellulose | 7-12 |
| Magnesium stearate | 0.5-0.9 |

and a second layer including:

| | % w/w (in layer) |
|---|---|
| Intergranular | |
| Emtricitabine | 39-67 |
| Tenofovir alafenamide hemifumarate | 5-10 |
| Microcrystalline cellulose | 22-38 |
| Croscarmellose sodium | 6-10 |
| Magnesium stearate | 0.3-0.7 |
| Intergranular | |
| Magnesium stearate | 0.3-0.7 |

and optionally a filmi coating.

| | % w/w (in layer) |
|---|---|
| Intergranular | |
| The compound of Formula I, or a pharmaceutically acceptable salt thereof | 13-17 |
| Microcrystalline cellulose | 58-79 |
| Croscarmellose sodium | 4.6-6.3 |
| Magnesium stearate | 0.6-0.8 |
| Extragranular | |
| Microcrystalline cellulose | 5-11 |
| Magnesium stearate | 0.6-0.8 |

and a second layer including:

| | % w/w (in layer) |
|---|---|
| Intergranular | |
| Emtricitabine | 45-61 |
| Tenofovir alafenamide, or a pharmaceutically acceptable salt thereof | 6-9 |
| Microcrystalline cellulose | 25-35 |
| Croscarmellose sodium | 6.5-9.2 |
| Magnesium stearate | 0.4-0.5 |
| Intergranular | |
| Magnesium stearate | 0.4-0.5 |

and optionally a film coating.

In one embodiment, a tablet is provided comprising a first layer including:

| | % w/w (in layer) |
|---|---|
| Intergranular | |
| The compound of Formula II | 13-17 |
| Microcrystalline cellulose | 58-79 |
| Croscarmellose sodium | 4.6-6.3 |
| Magnesium stearate | 0.6-0.8 |
| Extragranular | |
| Microcrystalline cellulose | 5-11 |
| Magnesium stearate | 0.6-0.8 |

and a second layer including:

| | % w/w (in layer) |
|---|---|
| Intergranular | |
| Emtricitabine | 45-61 |
| Tenofovir alafenamide hemifumarate | 6-9 |
| Microcrystalline cellulose | 25-35 |
| Croscarmellose sodium | 6.5-9.2 |
| Magnesium stearate | 0.4-0.5 |
| Intergranular | |
| Magnesium stearate | 0.4-0.5 |

and optionally a film coating.

In one embodiment, a tablet is provided comprising a first layer including:

| | % w/w (in layer) |
|---|---|
| Intergranular | |
| The compound of Formula I, or a pharmaceutically acceptable salt thereof | 14-16 |
| Microcrystalline cellulose | 66-73 |
| Croscarmellose sodium | 5.2-5.8 |
| Magnesium stearate | 0.65-0.75 |
| Extragranular | |
| Microcrystalline cellulose | 8-10 |
| Magnesium stearate | 0.65-0.75 |

and a second layer including:

| | % w/w (in layer) |
|---|---|
| Intergranular | |
| Emtricitabine | 50-56 |
| Tenofovir alafenamide, or a pharmaceutically acceptable salt thereof | 7-8 |
| Microcrystalline cellulose | 28-32 |
| Croscarmellose sodium | 7.5-8.5 |
| Magnesium stearate | 0.45-0.55 |
| Intergranular | |
| Magnesium stearate | 0.45-0.55 |

and optionally a film coating.

In one embodiment, a tablet is provided comprising a first layer including:

| | % w/w (in layer) |
|---|---|
| Intergranular | |
| The compound of Formula II | 14-16 |
| Microcrystalline cellulose | 66-73 |
| Croscarmellose sodium | 5.2-5.8 |
| Magnesium stearate | 0.65-0.75 |
| Extragranular | |
| Microcrystalline cellulose | 8-10 |
| Magnesium stearate | 0.65-0.75 |

and a second layer including:

| | % w/w (in layer) |
|---|---|
| Intergranular | |
| Emtricitabine | 50-56 |
| Tenofovir alafenamide hemifumarate | 7-8 |
| Microcrystalline cellulose | 28-32 |
| Croscarmellose sodium | 7.5-8.5 |
| Magnesium stearate | 0.45-0.55 |
| Intergranular | |
| Magnesium stearate | 0.45-0.55 |

and optionally a filmi coating.

In one embodiment, a tablet is provided comprising a first layer including:

| | % w/w (in layer) |
|---|---|
| Intergranular | |
| The compound of Formula II | 15 |
| Microcrystalline cellulose | 69 |
| Croscarmellose sodium | 5.5 |
| Magnesium stearate | 0.7 |
| Extragranular | |
| Microcrystalline cellulose | 9 |
| Magnesium stearate | 0.7 |

and a second layer including:

| | % w/w (in layer) |
|---|---|
| Intergranular | |
| Emtricitabine | 53 |
| Tenofovir alafenamide hemifumarate | 7.5 |
| Microcrystalline cellulose | 30 |
| Croscarmellose sodium | 8 |
| Magnesium stearate | 0.5 |
| Intergranular | |
| Magnesium stearate | 0.5 |

and optionally a filmi coating.

In one embodiment, a tablet is provided comprising a first layer including:

| | % w/w (in layer) |
|---|---|
| Intergranular | |
| The compound of Formula II | 15 |
| Microcrystalline cellulose | 69 |
| Croscarmellose sodium | 5.5 |
| Magnesium stearate | 0.7 |
| Extragranular | |
| Microcrystalline cellulose | 9 |
| Magnesium stearate | 0.7 |

and a second layer including:

| | % w/w (in layer) |
|---|---|
| Intergranular | |
| Emtricitabine | 53 |
| Tenofovir alafenamide hemifumarate | 7.5 |
| Microcrystalline cellulose | 30 |
| Croscarmellose sodium | 8 |
| Magnesium stearate | 0.7 |
| Intergranular | |
| Magnesium stearate | 0.7 |

and optionally a filmi coating.

In one embodiment, a tablet is provided comprising a first layer including:

| | Mass (mg) | % w/w (in layer) |
|---|---|---|
| Intragranular | | |
| The compound of Formula II | 52.5 | 16.24 |
| Microcrystalline cellulose | 149.9-246.3 | 46.41-76.26 |
| Croscarmellose sodium | 19.4 | 8.00 |
| Magnesium stearate | 1.98-2.45 | 0.6-1.0 |
| Extragranular | | |
| Microcrystalline cellulose | 0-97.0 | 0-30 |
| Magnesium stearate | 1.98-2.45 | 0.6-1.0 |

and a second layer including:

| | Mass (mg) | % w/w (in layer) |
|---|---|---|
| Intergranular | | |
| Emtricitabine | 200.00 | 53.05 |
| Tenofovir alafenamide hemifumarate | 28.1 | 7.45 |
| Microcrystalline cellulose | 113.2 | 30 |
| Croscarmellose sodium | 30.2 | 8.00 |
| Magnesium stearate | 1.93-2.85 | 0.50-0.75 |
| Extragranular | | |
| Magnesium stearate | 1.93-2.85 | 0.50-0.75 |

and optionally a filmi coating.

In one embodiment, a tablet is provided comprising a first layer consisting of.

| | Mass (mg) | % w/w (in layer) |
|---|---|---|
| Intergranular | | |
| The compound of Formula II | 52.5 | 16.24 |
| Microcrystalline cellulose | 149.9-246.3 | 46.41-76.26 |
| Croscarmellose sodium | 19.4 | 8.00 |
| Magnesium stearate | 1.98-2.45 | 0.6-1.0 |
| Extragranular | | |
| Microcrystalline cellulose | 0-97.0 | 0-30 |
| Magnesium stearate | 1.98-2.45 | 0.6-1.0 |

and a second layer consisting of.

| | Mass (mg) | % w/w (in layer) |
|---|---|---|
| Intergranular | | |
| Emtricitabine | 200.00 | 53.05 |
| Tenofovir alafenamide hemifumarate | 28.1 | 7.45 |
| Microcrystalline cellulose | 113.2 | 30 |
| Croscarmellose sodium | 30.2 | 8.00 |
| Magnesium stearate | 1.93-2.85 | 0.50-0.75 |
| Extragranular | | |
| Magnesium stearate | 1.93-2.85 | 0.50-0.75 |

and optionally a filmi coating.

In one embodiment, a tablet is provided comprising a first layer consisting of.

| | Mass (mg) | % w/w (in layer) |
|---|---|---|
| Intergranular | | |
| The compound of Formula II | 78.7 | 22.3 |
| Microcrystalline cellulose | 212.5 | 60.2 |
| Croscarmellose sodium | 21.2 | 6.00 |
| Magnesium stearate | 2.65 | 0.75 |
| Extragranular | | |
| Microcrystalline cellulose | 35.30 | 10.0 |
| Magnesium stearate | 2.65 | 0.75 |

and a second layer consisting of.

| | Mass (mg) | % w/w (in layer) |
|---|---|---|
| Intergranular | | |
| Emtricitabine | 200.00 | 53.05 |
| Tenofovir alafenamide hemifumarate | 28.0 | 7.4 |
| Microcrystalline cellulose | 113.2 | 30 |
| Croscarmellose sodium | 30.2 | 8.00 |
| Magnesium stearate | 2.83 | 0.75 |
| Extragranular | | |
| Magnesium stearate | 2.83 | 0.75 |

and optionally a filmi coating.

In one embodiment, a tablet is provided comprising a first layer consisting of.

| | Mass (mg) | % w/w (in layer) |
|---|---|---|
| Intergranular | | |
| The compound of Formula II | 52.5 | 16.25 |
| Microcrystalline cellulose | 0-246.3 | 0-76.25 |
| Croscarmellose sodium | 19.4 | 8.00 |
| Magnesium stearate | 1.98-2.45 | 0.6-1.0 |
| Extragranular | | |
| Microcrystalline cellulose | 0-97.0 | 0-30 |
| Magnesium stearate | 2.45 | 0.6-1.0 |

and a second layer consisting of:

| | Mass (mg) | % w/w (in layer) |
|---|---|---|
| Intergranular | | |
| Emtricitabine | 200.00 | 53.05 |
| Tenofovir alafenamide hemifumarate | 28.1 | 7.45 |
| Microcrystalline cellulose | 113.2 | 30 |
| Croscarmellose sodium | 30.2 | 8.00 |
| Magnesium stearate | 2.85 | 0.75 |
| Extragranular | | |
| Magnesium stearate | 2.85 | 0.75 |

and a film coating consisting of 21 mg of Opadry II Brown 85F165072 (a combination of polyvinyl alcohol, polyethylene gly col (PEG), tale, titanium dioxide, iron oxide red, and iron oxide black).

In one embodiment, a tablet is provided comprising a first layer including:

| | Mass (mg) | % w/w (in layer) |
|---|---|---|
| Intergranular | | |
| The compound of Formula II | 52.5 | 13-21 |
| Microcrystalline cellulose | 0-246 | 0-59 |
| Croscarmellose sodium | 19 | 5-25 |
| Magnesium stearate | 2.0-2.5 | 0.5-3.2 |
| Extragranular | | |
| Microcrystalline cellulose | 0-97 | 0-30 |
| Magnesium stearate | 2.0-2.5 | 0.5-3.2 |

and a second layer including:

| | Mass (mg) | % w/w (in layer) |
|---|---|---|
| Intergranular | | |
| Emtricitabine | 200 | 35 |
| Tenofovir alafenamide hemifumarate | 28 | 4.9 |
| Microcrystalline cellulose | 113 | 20 |
| Croscarmellose sodium | 30 | 5.2 |
| Magnesium stearate | 2.9 | 0.5 |
| Extragranular | | |
| Magnesium stearate | 2.9 | 0.5 |

and a film coating consisting of 21 mg of Opadry II Brown 85F165072 (a combination of poly vinyl alcohol, polyethylene gly col (PEG), tale, titanium dioxide, iron oxide red, and iron oxide black).

| | Mass (mg) | % w/w (in tablet) |
|---|---|---|
| The compound of Formula II | 47-58 | 6.75-8.25 |
| Microcrystalline cellulose | 222-271 | 32-59 |
| Croscarmellose sodium | 17-21 | 2.5-3.1 |
| Magnesium stearate | 4.4-5.4 | 0.6-0.8 |

and a second layer including:

| | Mass (mg) | % w/w (in tablet) |
|---|---|---|
| Emtricitabine | 180-220 | 26-31 |
| Tenofovir alafenamide hemifumarate | 25-31 | 3.6-4.4 |
| Microcrystalline cellulose | 104-127 | 15-18 |
| Croscarmellose sodium | 27-33 | 2.6-4.7 |
| Magnesium stearate | 3.4-6.0 | 0.4-1.0 |

and optionally a film coating (e.g., Opadry II Brown 85F165072 (a combination of polyvinyl alcohol, polyethylene glycol (PEG), tale, titanium dioxide, iron oxide red, and iron oxide black).

In one embodiment, a tablet is provided comprising a first layer including:

| | Mass (mg) | % w/w (in tablet) |
|---|---|---|
| The compound of Formula II | 52.5 | 7.5 |
| Microcrystalline cellulose | 246 | 35 |
| Croscarmellose sodium | 19 | 2.8 |
| Magnesium stearate | 5 | 0.7 |

and a second layer including:

| | Mass (mg) | % w/w (in tablet) |
|---|---|---|
| Emtricitabine | 200 | 29 |
| Tenofovir alafenamide hemifumarate | 28 | 4 |
| Microcrystalline cellulose | 115 | 16 |
| Croscarmellose sodium | 30 | 4.3 |
| Magnesium stearate | 4 | 0.5 |

and optionally a film coating (e.g., Opadry II Brown 85F165072 (a combination of polyvinyl alcohol, polyethylene glycol (PEG), talc, titanium dioxide, iron oxide red, and iron oxide black).

In one embodiment, a tablet is provided comprising a first layer consisting of:

| | Mass (mg) | % w/w (in layer) |
|---|---|---|
| Intergranular | | |
| The compound of Formula II | 78.6 | 22.3 |
| Microcrystalline cellulose | 212.5 | 60.2 |
| Croscarmellose sodium | 21.2 | 6.00 |
| Magnesium stearate | 2.65 | 0.75 |
| Extragranular | | |
| Microcrystalline cellulose | 35.3 | 10.0 |
| Magnesium stearate | 2.65 | 0.75 |

and a second layer consisting of:

| | Mass (mg) | % w/w (in layer) |
|---|---|---|
| Intergranular | | |
| Emtricitabine | 200.00 | 53.05 |
| Tenofovir alafenamide hemifumarate | 28.1 | 7.45 |
| Microcrystalline cellulose | 113.1 | 30 |
| Croscarmellose sodium | 30.2 | 8.00 |
| Magnesium stearate | 2.85 | 0.75 (0.5-0.75) |
| Extragranular | | |
| Magnesium stearate | 2.83 | 0.75 (0.5-7.5) |

and a film coating consisting of 21.9 mg of Opadry II Yellow 85F92259 (a combination of polyvinyl alcohol, polyethylene glycol (PEG), talc, titanium dioxide and iron yellow).

In one embodiment, a composition is provided including about 75 mg of a compound of Formula I, or a pharmaceutically acceptable salt thereof (e.g., a compound of Formula II), about 25 mg tenofovir alafenamide, or a pharmaceutically acceptable salt thereof, and about 200 mg emtricitabine, or a pharmaceutically acceptable salt thereof, wherein the mean $AUC_{last}$ of each component following a single dose administered to a human is from about 81700 h-ng/mL to about 140000 h-ng/mL of the compound of Formula I, from about 7500 h-ng/mL to about 15000 h-ng/mL of emtricitabine, and from about 165 h-ng/mL to about 400 h-ng/mL of tenofovir alafenamide. In certain embodiments, the composition is administered to the human in a fasted state. In certain embodiments, the composition is a tablet. In certain embodiments, the tablet is a bilayer tablet. In certain embodiments, the tablet is a bilayer tablet, with the Compound of Formula I in one layer and emtricitabine and tenofovir alafenamide in the other layer.

In one embodiment, a composition is provided including a compound of 50 mg Formula I, or a pharmaceutically acceptable salt thereof (e.g., a compound of Formula II). 25 mg tenofovir alafenamide, or a pharmaceutically acceptable salt thereof, and 200 mg emtricitabine, or a pharmaceutically acceptable salt thereof, wherein the mean $AUC_{last}$ of each component following a single dose is from about 87,000 h-ng/mL to about 131,000 h-ng/mL of the compound of Formula I, from about 8500 h-ng/mL to about 12.800 h-ng/mL of emtricitabine, and from about 186 h-ng/mL to about 227 h-ng/mL of tenofovir alafenamide. In certain embodiments, the composition is administered to the human in a fasted state. In certain embodiments, the composition is a tablet. In certain embodiments, the tablet is a bilayer tablet. In certain embodiments, the tablet is a bilayer tablet, with the Compound of Formula I in one layer and emtricitabine and tenofovir alafenamide in the other layer. In certain embodiments, the subject is fasted. In other embodiments, the subject is fed.

In one embodiment, a composition is provided including a compound of Formula I, or a pharmaceutically acceptable salt thereof (e.g., a compound of Formula II), tenofovir alafenamide, or a pharmaceutically acceptable salt thereof, and emtricitabine, or a pharmaceutically acceptable salt thereof, wherein the mean $AUC_{inf}$ of each component following a single dose administered to a human is from about 84450 h-ng/mL to about 141000 h-ng/mL of the compound of Formula I, from about 8100 h-ng/mL to about 136000 h-ng/mL of emtricitabine, and from about 200 h-ng/mL to about 500 h-ng/mL of tenofovir alafenamide. In certain embodiments, the composition is administered to the human in a fasted state. In certain embodiments, the composition is a tablet. In certain embodiments, the tablet is a bilayer tablet. In certain embodiments, the tablet is a bilayer tablet, with the Compound of Formula I in one layer and emtricitabine and tenofovir alafenamide in the other layer. In certain embodiments, the subject is fasted. In other embodiments, the subject is fed.

In one embodiment, a composition is provided including a compound of Formula I (e.g., a compound of Formula II), tenofovir alafenamide, and emtricitabine, wherein the mean $C_{max}$ of each component following a single dose is from about 90.000 h-ng/mL to about 135,000 h-ng/mL of the compound of Formula I, from about 8,700 h-ng/mL to about 13,000 h-ng/mL of emtricitabine, and from about 200 h-ng/mL to about 300 h-ng/mL of tenofovir alafenamide. In certain embodiments, the composition is administered to the human in a fasted state. In certain embodiments, the composition is a tablet. In certain embodiments, the tablet is a bilayer tablet. In certain embodiments, the tablet is a bilayer tablet, with the Compound of Formula I in one layer and emtricitabine and tenofovir alafenamide in the other layer. In certain embodiments, the subject is fasted. In other embodiments, the subject is fed.

In one embodiment, a composition is provided including a compound of Formula I, or a pharmaceutically acceptable salt thereof (e.g., a compound of Formula II), tenofovir alafenamide, or a pharmaceutically acceptable salt thereof, and emtricitabine, or a pharmaceutically acceptable salt thereof, wherein the mean $C_{max}$ of each component following a single dose administered to a human is from about 4200 ng/mL to about 8000 mg/mL of the compound of Formula I, from about 1770 ng/mL to about 2800 ng/mL of emtricitabine, and from about 185 ng/mL to about 315 ng/mL of tenofovir alafenamide. In certain embodiments, the composition is administered to the human in a fasted state. In certain embodiments, the composition is a tablet. In certain embodiments, the tablet is a bilayer tablet. In certain embodiments, the tablet is a bilayer tablet, with the Compound of Formula I in one layer and emtricitabine and tenofovir alafenamide in the other layer. In certain embodiments, the subject is fasted. In other embodiments, the subject is fed.

In one embodiment, a composition is provided including a compound of Formula I, or a pharmaceutically acceptable salt thereof (e.g., a compound of Formula II), tenofovir alafenamide, or a pharmaceutically acceptable salt thereof, and emtricitabine, or a pharmaceutically acceptable salt thereof, wherein the mean $C_{max}$ of each component following a single dose is from about 4700 ng/mL to about 5300 ng/mL of the compound of Formula I, from about 2000 ng/mL, to about 2600 ng/mL of emtricitabine, and from about 200 ng/mL to about 300 ng/mL of tenofovir alafenamide. In certain embodiments, the composition is administered to the human in a fasted state. In certain embodiments, the composition is a tablet. In certain embodiments, the tablet is a bilayer tablet. In certain embodiments, the tablet is a bilayer tablet, with the Compound of Formula I in one layer and emtricitabine and tenofovir alafenamide in the other layer. In certain embodiments, the subject is fasted. In other embodiments, the subject is fed.

In one embodiment, a composition is provided including a compound of Formula I, or a pharmaceutically acceptable salt thereof (e.g., a compound of Formula II), tenofovir alafenamide, or a pharmaceutically acceptable salt thereof, and emtricitabine, or a pharmaceutically acceptable salt thereof, wherein the mean $AUC_{last}$-$AUC_{inf}$, and/or $C_{max}$ of each component following a single dose administered to a human in the fed state is 80-125%, 80-120%, 85-115%, 90-110%, or 95-105% of the mean $AUC_{last}$, $AUC_{inf}$, and/or $C_{max}$ of each component following a single dose administered to a human in the fasted state. In certain embodiments, the composition is a tablet. In certain embodiments, the tablet is a bilayer tablet. In certain embodiments, the tablet is a bilayer tablet, with the Compound of Formula I in one layer and emtricitabine and tenofovir alafenamide in the other layer. In certain embodiments, the subject is fasted. In other embodiments, the subject is fed.

In certain embodiments, the pharmacokinetic profile of the compositions described herein is within acceptable ranges, regardless of whether the subject has eaten prior to taking the medication. Accordingly, in certain embodiments, the compositions described herein can be taken without regard to food intake by the subject. In certain embodiments, food intake is a low fat, moderate fat, or high fat meal.

In one embodiment, a composition comprising 50 mg Compound of Formula I. 25 mg tenofovir alafenamide, and 200 mg emtricitabine is provided, wherein the mean $AUC_{last}$ of a single dose following administration to fed patients is within about 100% to about 160% of the mean $AUC_{last}$ of a single dose following administration to fasted patients. In another embodiment, a composition comprising 50 mg Compound of Formula I. 25 mg tenofovir alafenamide, and 200 mg emtricitabine is provided, wherein the mean $AUC_{last}$ of a single dose following administration to fed patients is within about 100% to about 145% of the mean $AUC_{last}$ of a single dose following administration to fasted patients. In a further embodiment, a composition comprising 50 mg Compound of Formula I, 25 mg tenofovir alafenamide, and 200 mg emtricitabine is provided, wherein the mean $AUC_{last}$ of a single dose following administration to fed patients is within about 100% to about 135% of the mean $AUC_{last}$ of a single dose following administration to fasted patients. In another embodiment, a composition comprising 50 mg Compound of Formula I. 25 mg tenofovir alafenamide, and 200 mg emtricitabine is provided, wherein the mean $AUC_{last}$ of a single dose following administration to fed patients is within about 100% to about 125% of the mean $AUC_{last}$ of a single dose following administration to fasted patients.

In certain embodiments, a composition comprising 50 mg Compound of Formula I, 25 mg tenofovir alafenamide, and 200 mg emtricitabine is provided, wherein the mean $AUC_{last}$ of a single dose following administration to fed patients is within 60% of the mean $AUC_{last}$ of a single dose following administration to fasted patients. In another embodiment, a composition comprising 50 mg Compound of Formula I. 25 mg tenofovir alafenamide, and 200 mg emtricitabine is provided, wherein the mean $AUC_{last}$ of a single dose following administration to fed patients is within 45% of the mean $AUC_{last}$ of a single dose following administration to fasted patients. In a further embodiment, a composition comprising 50 mg Compound of Formula I, 25 mg tenofovir alafenamide, and 200 mg emtricitabine is provided, wherein the mean $AUC_{last}$ of a single dose following administration to fed patients is within 35% of the mean $AUC_{last}$ of a single dose following administration to fasted patients. In another embodiments a composition comprising 50 mg Compound of Formula I, 25 mg tenofovir alafenamide, and 200 mg emtricitabine is provided, wherein the mean $AUC_{last}$ of a single dose following administration to fed patients is within 25% of the mean AUC last of a single dose following administration to fasted patients.

In one embodiment, a composition comprising 50 mg Compound of Formula I, 25 mg tenofovir alafenamide, and 200 mg emtricitabine is provided, wherein the mean $AUC_{inf}$ of a single dose following administration to fed patients is within about 100% to about 160% of the mean $AUC_{inf}$ of a single dose following administration to fasted patients. In another embodiment, a composition comprising 50 mg Compound of Formula I, 25 mg tenofovir alafenamide, and 200 mg emtricitabine is provided, wherein the mean $AUC_{inf}$ of a single dose following administration to fed patients is within about 100% to about 150% of the mean $AUC_{inf}$ of a single dose following administration to fasted patients. In a further embodiment, a composition comprising 50 mg Compound of Formula I. 25 mg tenofovir alafenamide, and 200 mg emtricitabine is provided, wherein the mean $AUC_{inf}$ of a single dose following administration to fed patients is within about 100% to about 135% of the mean $AUC_{inf}$ of a single dose following administration to fasted patients. In another embodiment, a composition comprising 50 mg Compound of Formula I, 25 mg tenofovir alafenamide, and 200 mg emtricitabine is provided, wherein the mean $AUC_{inf}$ of a single dose following administration to fed patients is within about 100% to about 125% of the mean $AUC_{last}$ of a single dose following administration to fasted patients.

In certain embodiments, a composition comprising 50 mg Compound of Formula I, 25 mg tenofovir alafenamide, and 200 mg emtricitabine is provided, wherein the mean $AUC_{inf}$ of a single dose following administration to fed patients is within 60% of the mean $AUC_{inf}$ of a single dose following administration to fasted patients. In another embodiment, a composition comprising 50 mg Compound of Formula I, 25 mg tenofovir alafenamide, and 200 mg emtricitabine is provided, wherein the mean $AUC_{inf}$ of a single dose following administration to fed patients is within 50% of the mean $AUC_{inf}$ of a single dose following administration to fasted patients. In a further embodiment, a composition comprising 50 mg Compound of Formula I. 25 mg tenofovir alafenamide, and 200 mg emtricitabine is provided, wherein the mean $AUC_{inf}$ of a single dose following administration to fed patients is within 35% of the mean $AUC_{inf}$ of a single dose following administration to fasted patients. In another embodiments a composition comprising 50 mg Compound of Formula I. 25 mg tenofovir alafenamide, and 200 mg emtricitabine is provided, wherein the mean $AUC_{inf}$ of a single dose following administration to fed patients is within 25% of the mean $AUC_{inf}$ of a single dose following administration to fasted patients.

In one embodiment, a composition comprising 50 mg Compound of Formula I. 25 mg tenofovir alafenamide, and 200 mg emtricitabine is provided, wherein the mean $C_{max}$ of a single dose following administration to fed patients is within about 100% to about 160% of the mean $C_{max}$ of a single dose following administration to fasted patients. In another embodiment, a composition comprising 50 mg Compound of Formula I, 25 mg tenofovir alafenamide, and 200 mg emtricitabine is provided, wherein the mean $C_{max}$ of a single dose following administration to fed patients is within about 100% to about 130% of the mean $C_{max}$ of a single dose following administration to fasted patients. In a further embodiment, a composition comprising 50 mg Compound of Formula I, 25 mg tenofovir alafenamide, and 200 mg emtricitabine is provided, wherein the mean $C_{max}$ of a single dose following administration to fed patients is within about 100% to about 120% of the mean $C_{max}$ of a single dose following administration to fasted patients. In another embodiment, a composition comprising 50 mg Compound of Formula I, 25 mg tenofovir alafenamide, and 200 mg emtricitabine is provided, wherein the mean $C_{max}$ of a single dose following administration to fed patients is within about 100% to about 115% of the mean $C_{max}$ of a single dose following administration to fasted patients.

In certain embodiments, a composition comprising 50 mg Compound of Formula I, 25 mg tenofovir alafenamide, and 200 mg emtricitabine is provided, wherein the mean $C_{max}$ of a single dose following administration to fed patients is within 60% of the mean $C_{max}$ of a single dose following administration to fasted patients. In another embodiment, a composition comprising 50 mg Compound of Formula I. 25 mg tenofovir alafenamide, and 200 mg emtricitabine is provided, wherein the mean $C_{max}$ of a single dose following administration to fed patients is within 30% of the mean $C_{max}$ of a single dose following administration to fasted patients. In a further embodiment, a composition comprising 50 mg Compound of Formula I. 25 mg tenofovir alafenamide, and 200 mg emtricitabine is provided, wherein the mean $C_{max}$ of a single dose following administration to fed patients is within 20% of the mean $C_{max}$ of a single dose following administration to fasted patients. In another embodiments a composition comprising 50 mg Compound of Formula I. 25 mg tenofovir alafenamide, and 200 mg emtricitabine is provided, wherein the mean $C_{max}$ of a single dose following administration to fed patients is within 15% of the mean $C_{max}$ of a single dose following administration to fasted patients.

Manufacturing Methods

Methods for producing the compositions and dosage forms (in particular tablets) disclosed herein are also provided. In some embodiments, the method comprises (a) compressing the compound of Formula I or a pharmaceutically acceptable salt thereof as a first layer, and (b) compressing the tenofovir alafenamide or a pharmaceutically acceptable salt thereof and emtricitabine or a pharmaceutically acceptable salt thereof as a second layer. For example, in some embodiments, the method comprises (a) compressing the compound of Formula I or a pharmaceutically acceptable salt thereof as a first layer, followed by (b) compressing the tenofovir alafenamide or a pharmaceutically acceptable salt thereof and emtricitabine or a pharmaceutically acceptable salt thereof as a second layer. In other embodiments, the method comprises (a) compressing the tenofovir alafenamide or a pharmaceutically acceptable salt thereof and emtricitabine or a pharmaceutically acceptable salt thereof followed by (b) compressing the compound of Formula I or a pharmaceutically acceptable salt thereof as another layer. In other embodiments, the method comprises (a) compressing the compound of Formula I or a pharmaceutically acceptable salt thereof as one layer followed by (b) compressing the tenofovir alafenamide or a pharmaceutically acceptable salt thereof and emtricitabine or a pharmaceutically acceptable salt thereof as another layer. The first layer and second layer may be compressed separately and subsequently combined. However, more typically, a first layer is formed by compression and subsequently a second layer is compressed onto the first layer. In certain embodiments, the choice of layer order in the tableting of multilayer tablets may have an impact on the properties of the tablets (e.g., the adhesion of the layers within the tablet).

In some embodiments, a tablet is provided wherein the first layer is obtainable by a method of (a) compressing the compound of Formula I or a pharmaceutically acceptable salt thereof as a first layer, and (b) compressing the tenofovir alafenamide or a pharmaceutically acceptable salt thereof and emtricitabine or a pharmaceutically acceptable salt thereof as a second layer. In other embodiments, a tablet is provided wherein the second layer is obtainable by a method of (a) compressing the compound of Formula I or a pharmaceutically acceptable salt thereof as a first layer, and (b) compressing the tenofovir alafenamide or a pharmaceutically acceptable salt thereof and emtricitabine or a pharmaceutically acceptable salt thereof as a first layer.

In certain embodiments, the methods will include a step of coating the tablet cores after compression, e.g., with a film coating as described above.

In general, tableting methods are well known in the art of pharmacy. Techniques and formulations generally are found in Remington's Pharmaceutical Sciences (Mack Publishing Co., Easton, PA), which is hereby incorporated by reference herein in its entirety.

A tablet can be made by compression or molding, optionally with one or more excipients. Compressed tablets may be prepared by compressing in a suitable machine the active ingredient in a free-flowing form such as a powder or granules, optionally mixed with excipients.

Therapeutic Methods

The solid oral dosage forms (in particular tablets) disclosed herein are used for treatment of HIV infection (e.g. HIV-1 infection). In certain embodiments, the solid oral dosage forms (in particular tablets) disclosed herein are used for pre-exposure prophylaxis (PrEP) to reduce the risk of sexually acquired HIV-1.

Accordingly, methods for treating a subject infected with HIV are provided, comprising administering a solid oral dosage form disclosed herein (in particular a tablet) to the subject. Similarly, a solid oral dosage form (in particular a tablet) is provided for use in such treatment methods. Also provided is the use of the compound of Formula I or a pharmaceutically acceptable salt thereof, tenofovir alafenamide or a pharmaceutically acceptable salt thereof, and emtricitabine or a pharmaceutically acceptable salt thereof, in the manufacture of an oral dosage form disclosed herein (in particular a tablet) for treatment of HIV infection. In some embodiments, the invention provides the use of tenofovir alafenamide or a pharmaceutically acceptable salt thereof, and emtricitabine or a pharmaceutically acceptable salt thereof, in the manufacture of an oral dosage form disclosed herein (in particular a tablet) for treatment of HIV infection.

In certain embodiments, the solid oral dosage forms (in particular tablets) disclosed herein are used for pre-exposure prophylaxis (PrEP) to reduce the risk of sexually acquired HIV-1. Accordingly, methods for preventing infection in a subject at risk of infection with HIV are provided, comprising administering a solid oral dosage form disclosed herein (in particular a tablet) to the subject. Similarly, a solid oral dosage form disclosed herein (in particular a tablet) is provided for use in such treatment methods. The invention also provides the use of the compound of Formula I or a pharmaceutically acceptable salt thereof, tenofovir alafenamide or a pharmaceutically acceptable salt thereof, and emtricitabine or a pharmaceutically acceptable salt thereof, in the manufacture of an oral dosage form disclosed herein (in particular a tablet) for prevention of HIV infection in a subject at risk for infection. In some embodiments, the invention provides the use of tenofovir alafenamide or a pharmaceutically acceptable salt thereof, and emtricitabine or a pharmaceutically acceptable salt thereof, in the manufacture of an oral dosage fonn disclosed herein (in particular a tablet) for prevention of HIV infection.

In certain embodiments, a method of treating a subject with HIV with the compositions disclosed herein is provided, wherein the method does not increase the risk of a drug-drug interaction in the patient. In certain embodiments, a method of treating a subject with HIV with the compositions disclosed herein is provided, wherein the method decreases the risk of a drug-drug interaction in the patient. Exemplary drug-drug interactions include interactions between the compound of Formula I, tenofovir alafenamide, or emtricitabine with rifampin, metformin, one or more hormonal contraceptives or an HCV antiviral agent (e.g., one or more of sofosbuvir, ledipasvir, velpatasvir, voxilaprevir, grazoprevir, boceprevir, elbasvir, dasabuvir, ombitasvir, paritaprevir. ABT-530, and ABT-493). In certain embodiments, a method of treating a subject with HIV is provided, wherein the subject is administered one or the compositions disclosed herein, wherein the subject is also being treated with rifampin, metformin, or an HCV antiviral agent (e.g., one or more of sofosbuvir, ledipasvir, velpatasvir, voxilaprevir, grazoprevir, boceprevir, elbasvir, dasabuvir, ombitasvir, paritaprevir, ABT-530, and ABT-493).

The methods involve administering an oral dosage form disclosed herein (in particular a tablet) to the subject, typically a human, and will generally involve repeated administrations, typically once daily. The treatment may be prophylactic or therapeutic treatment General The term "fed" in relation to administration of a solid oral dosage form to a human subject means administration of the dosage form orally under fed conditions (moderate fat meal) e.g. administration within about 30 minutes of the human consuming a standardized meal of about 300 to 600 calories and about 10 to about 15 grams of fat. In some embodiments. "fed" refers to administration within about 30 minutes of the human consuming a high fat meal.

The term "substantially free" in relation to the presence of a given component within e.g., a composition means that less than 5% by weight of the composition (e.g., less than 1% by weight of the composition) is that given component. The word "substantially" does not exclude "completely" e.g., a composition which is "substantially free" from Y may be completely free from Y. Where necessary, the word "substantially" may be omitted from the definition of the invention.

The term "segregated" as used in relation to certain components (e.g. A and B) within a tablet means that those components are physically discrete such that the presence of one component (e.g. A) does not substantially affect the stability in storage of the other component(s) (e.g. B) from which it is segregated. Typically, when components are segregated in a tablet then they will be present in separate layers in a multilayer tablet. By way of example, components A and B may be present in separate layers in a multilayer tablet, wherein (a) the layer containing component A is substantially free of component B and (b) the layer containing component B is substantially free of component A. The separate layers may be in contact with each other or may be separated e.g., by one or more additional layers.

The term "comprise" and variations thereof, such as "comprises" and "comprising", are to be construed in an open, inclusive sense, that is as "including, but not limited to".

The term "between" with reference to two values includes those two values e.g., the range "between" 10 mg and 20 mg encompasses e.g. 10, 11, 12, 13, 14, 15, 16, 17, 18, 19 and 20 mg.

The term "about" used in connection with a quantity is inclusive of the stated value and has the meaning dictated by the context (e.g., includes the degree of error associated with measurement of the particular quantity). For example, in certain nonlimiting example the term "about" in relation to a numerical value x refers to x±10%, x±5%, or x±1%.

"% w/w" means the weight of a component as a percentage of the total weight of e.g., a layer or dosage form in which the component is present. For example, a composition comprising "5% w/w X" refers to a composition in which the weight of component X is 5% of the total weight of the composition.

Reference throughout this specification to "one embodiment" or "an embodiment" means that a particular feature, structure or characteristic described in connection with the embodiment is included in at least one embodiment provided herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The term "pharmaceutically acceptable" with respect to a substance refers to that substance which is generally regarded as safe and suitable for use without undue toxicity, irritation, allergic response, and the like, commensurate with a reasonable benefit/risk ratio. "Pharmaceutically acceptable" with regard to excipients includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci . . . 66 (1), 1-19 (1977), and Remington: The Science and Practice of Pharmacy, R. Hendrickson, ed., 21st edition, Lippincott. Williams & Wilkins, Philadelphia. PA. (2005), at p. 732. Table 38-5, both of which are hereby incorporated by reference herein.

As used herein, the term "salts" includes co-crystals. The term "co-crystal" refers to a crystalline compound comprising two or more molecular components, e.g., wherein proton transfer between the molecular components is partial or incomplete.

The term "solvate" means a molecular complex comprising a compound and one or more pharmaceutically acceptable solvent molecules. Examples of solvent molecules include water and $C_{1-6}$ alcohols, e.g., ethanol. When the solvate is water, the term "hydrate" may be used.

"Treating" and "treatment" of a disease include the following:

(1) preventing or reducing the risk of developing the disease, i.e. causing the clinical symptoms of the disease not to develop in a subject that may be exposed to or predisposed to the disease but does not yet experience or display symptoms of the disease, (2) inhibiting the disease, i.e. arresting or reducing the development of the disease or its clinical symptoms, and (3) relieving the disease, i.e. causing regression of the disease or its clinical symptoms.

The term "effective amount" refers to an amount that may be effective to elicit the desired biological or medical response, including the amount of a compound that, when administered to a subject for treating a disease, is sufficient to effect such treatment for the disease. The effective amount will vary depending on the compound, the disease and its severity and the age, weight, etc. of the subject to be treated. The effective amount can include a range of amounts.

EXAMPLES

The following examples are provided for purposes of illustration, not limitation.

Example 1—Compound of Formula II Single Agent Tablets

Figure 5:
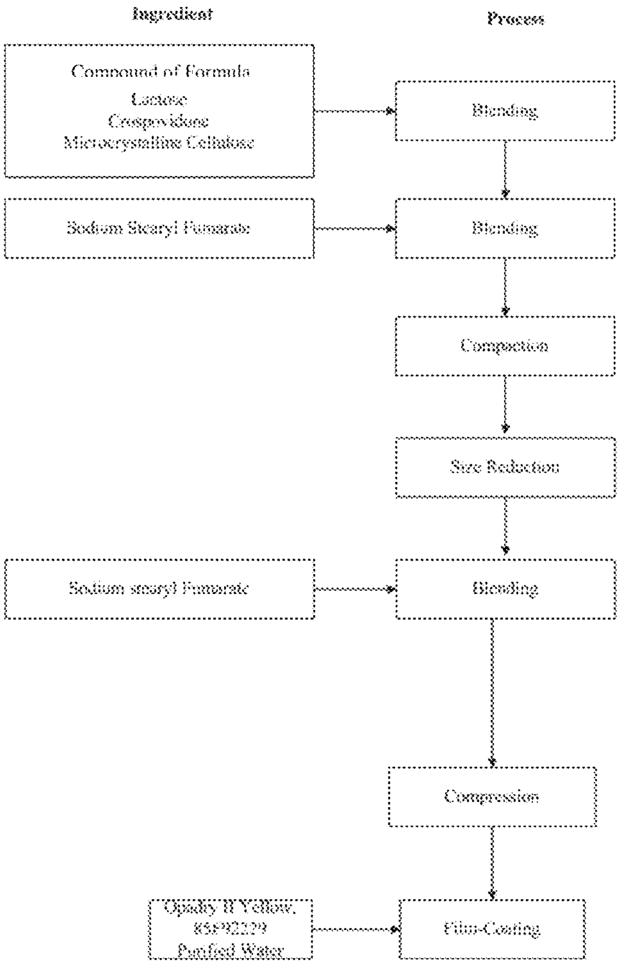
FIG. 5 is a flow diagram illustrating the preparation of a tablet formulation containing the compound of Formula II.

A formulation (tablet F1) of the compound of Formula II was prepared by dry granulation. FIG. 5 is a flow diagram illustrating the preparation of this formulation. The composition of the single agent formulation is shown in the table below:

| | Tablet Formulation F1 | |
|---|---|---|
| Component | Mass (mg/tablet) | % w/w/tablet |
| Compound of Formula II | 78.7* | 26.2 |
| Microcrystalline cellulose | 120 | 40 |
| Lactose monohydrate | 75.8 | 25.3 |
| Crospovidone | 21 | 7 |
| Sodium Stearyl Fumarate** | 4.5 | 1.5 |
| Total Weight | 300 | |

*Equivalent to 75 mg of the Compound of Formula I

**Intergranular: 2.25 mg (0.75%; Extragranular: 2.25 mg (0.75%)

In the pharmacokinetic studies of Example 3, the tablets of Formulation F1 were film coated with 12 mg Opadry II Yellow 85F92259. The total weight of the film coated tablets was 312 mg.

The Compound of Formula II was blended with intergranular excipients (lactose, microcrystalline cellulose, and crospovidone), further blended with the intergranular portion of the sodium stearyl fumarate), roller compacted, milled, and final blended with the sodium stearyl fumarate to yield a final powder blend for compression. The final powder blend had a mean particle size of 347 μm with a compressibility index of 21%. The final powder blend was compressed into tablet cores, which were film-coated as described above to a target weight gain of 4%.

Figure 6:
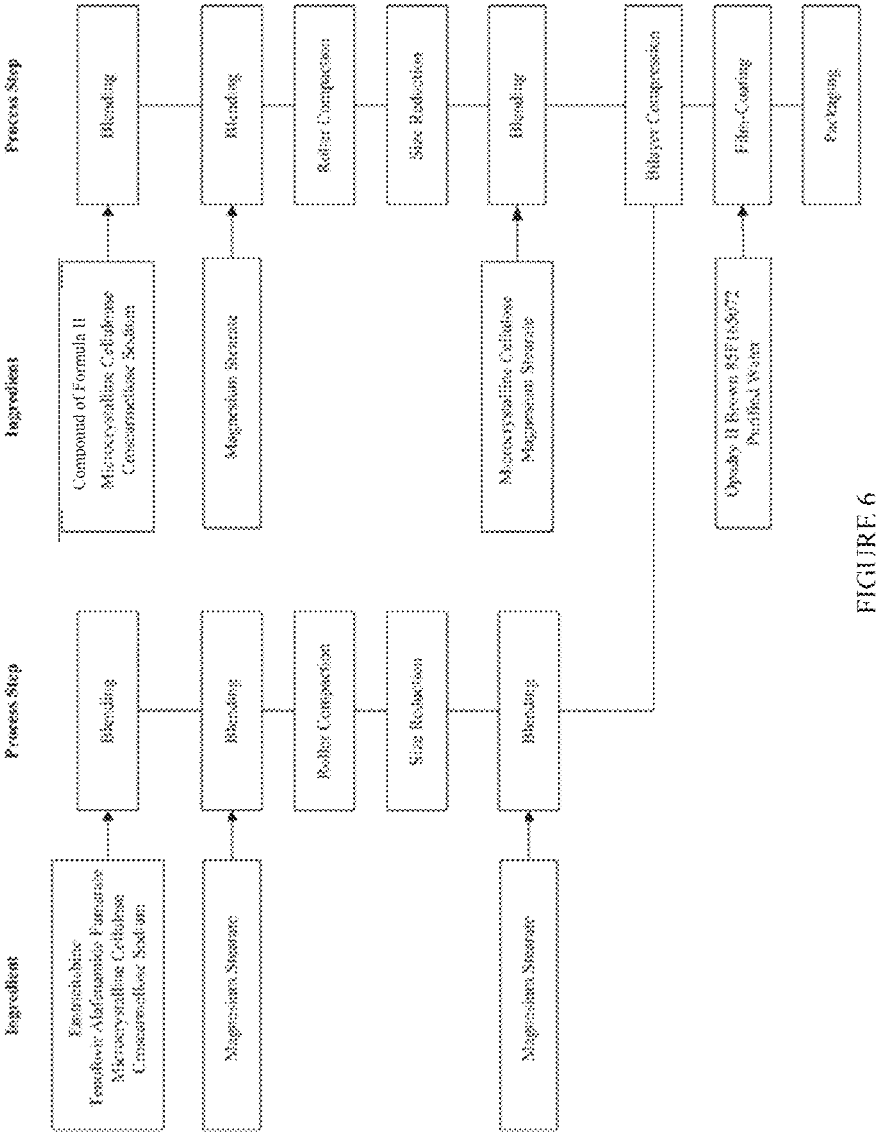
FIG. 6 is a flow diagram illustrating the preparation of a tablet formulation containing the compound of Formula II, emtricitabine, and tenofovir alafenamide hemifumarate.

Example 2—Compound of Formula II/Emtricitabine/Tenofovir Alafenamide Bilayer Tablets A bilayer formulation (tablet F2) of the compound of Formula II, emtricitabine, and tenofovir alafenamide hemifumarate was prepared using the method described in Example 8. FIG. 6 is a flow diagram illustrating the preparation of bilayer tablets. The composition of the formulation is summarized in the table below:

| | Bilayer tablet F2 (mg/tablet) | |
|---|---|---|
| Ingredient | Compound of Formula II Layer | Emtricitabine/ tenofovir alafenamide hemifumarate Layer |
| Compound of Formula II | 78.7* | |
| Emtricitabine | | 200 |
| Tenofovir alafenamide hemifumarate | | 28.1** |

-continued

| Ingredient | Bilayer tablet F2 (mg/tablet) Compound of Formula II Layer | Emtricitabine/ tenofovir alafenamide hemifumarate Layer |
|---|---|---|
| Microcrystalline cellulose | 247.8*** | 113.1 |
| Croscarmellose sodium | 21.2 | 30.2 |
| Magnesium Stearate | 5.3† | 5.7†† |
| Layer Weight | 353 | 377 |
| Tablet Core Weight | 730 | |

*Equivalent to 75 mg of the Compound of Formula I

**Equivalent to 25 mg tenofovir alafenamide

***Intergranular: 212.5 mg (29.1%); Extragranular: 2.65 mg (0.4%)

†Intergranular: 2.65 mg (0.4%); Extragranular: 2.65 mg (0.4%)

††Intergranular: 2.83 mg (0.4%); Extragranular: 2.83 mg (0.4%)

In the pharmacokinetic studies of Example 3, the tablets of Formulation F2 were film coated with 21.9 mg Opadry II Yellow 85F92259 (represented 3% weight gain). The total weight of the film coated tablets was 752 mg.

The tablets were manufactured using a dry granulation by roller compaction process. An emtricitabine/tenofovir alafenamide final powder blend was manufactured by dry granulation of emtricitabine and tenofovir alafenamide with excipients (microcrystalline cellulose, croscarmellose sodium, intergranular magnesium stearate), followed by blending with extragranular lubricant (extragranular magnesium stearate). The final powder blend of the Compound of Formula I was manufactured by dry granulation of the active component with excipients (microcrystalline cellulose, croscarmellose sodium, intergranular magnesium stearate) followed by blending with the extragranular filler and lubricant (microcrystalline cellulose and extragranular magnesium stearate). In this study, the emtricitabine/tenofovir alafenamide final powder blend was compressed as layer 1 and the final powder blend of the Compound of Formula I was compressed as layer 2 to give a final bilayer tablet core. The core was film coated as described above.

Example 2a Emtricitabine/Tenofovir Alafenamide Tablets

The composition of the emtricitabine/tenofovir alafenamide (F/TAF) fixed dose combination tablets used in subsequent studies is shown in the following table:

| Component | Tablet Formulation F3 Emtricitabine/ tenofovir alafenamide 200/25 mg (mg/tablet) |
|---|---|
| Intergranular | |
| Emtricitabine | 200 |
| Tenofovir Alafenamide Hemifumarate | 28.0 |
| Microcrystalline Cellulose | 88.7 |
| Croscarmellose Sodium | 28.0 |
| Magnesium Stearate | 2.6 |
| Extragranular | |
| Magnesium Stearate | 2.6 |
| Total Tablet Core Weight | 350 |
| Film-Coating | |
| Opadry II Blue 85F105057 | 10.5 |

Emtricitabine and tenofovir alafenamide hemifumarate were co-blended with microcrystalline cellulose and croscarmellose sodium, followed by lubrication with magnesium stearate. The roller compaction pre-blend was then roller compacted and milled using an oscillating mill. The resultant granules were lubricated with magnesium stearate and compressed into 350 mg tablet cores which that were subsequently film coated.

Example 3—Pharmacokinetic Studies

Studies were carried out to assess the pharmacokinetic profiles of the formulations F1, F2, and F3 of Examples 1, 2, and 2A. A randomized, open-label, multiple-period, fixed-sequence, crossover study was performed to evaluate the relative bioavailability of bilayer tablet formulation F2 compared with that of single agent tablet formulation F1 co-administered simultaneously with a fixed-dose combination tablet containing emtricitabine and tenofovir alafenamide (tablet formulation F3). The bioavailability was evaluated in healthy subjects.

Study Design and Duration of Treatment

Three single doses of the following tablet formulations were administered orally during up to 21 days total study duration:

(a) a fixed dosed combination tablet containing citricitabine and tenofovir alafenamide (200/25 mg-Tablet F3) and a single agent tablet containing the compound of Formula I (75 mg-Tablet F1) administered simultaneously, under fasted conditions (dosed on day 1: days 2-8 washout);

(b) a fixed dose combination tablet containing the compound of Formula I, emtricitabine, and tenofovir alafenamide (75/200/25 mg-Tablet F2) administered under fasted conditions (dosed on day 9; days 10-16 washout); and (c) a fixed dose combination tablet containing the compound of Formula I, emtricitabine, and tenofovir alafenamide (75/200/25 mg-Tablet F2) administered under fed conditions with a high-fat meal (dosed on day 17; day 21 discharge).

Criteria for Evaluation

The following plasma pharmacokinetic parameters were calculated: $C_{max}$-$AUC_{last}$, and $AUC_{inf}$.

Statistical Methods

Pharmacokinetics: Plasma concentrations and PK parameters were listed and summarized by analyte and treatment group using descriptive statistics. In addition, a parametric analysis of variance using a mixed-effects model appropriate for a crossover design was fitted to the natural logarithmic transformation of the PK parameters ($AUC_{inf}$, $AUC_{last}$, and $C_{max}$). Two-sided 90% confidence intervals (CIs) were constructed for the ratio of geometric least-squares means (GLSMs) of each PK parameter for the compound of Formula I, emtricitabine, and tenofovir alafenamide.

Results

Subject Disposition and Demographics

A total of 28 subjects were randomized and received at least 1 dose of study drug.

The results for the first cohort of the clinical study are summarized in the table below. This table presents the mean (% CV) values, Geometric Least Squares Mean (GLSM) ratios, and 90% CI values of the plasma PK parameters $AUC_{last}$, $AUC_{inf}$, and $C_{max}$ for each active ingredient, following administration of bilayer tablet formulation F2 or the single agent tablet formulation F1, co-administered with a fixed dose combination of emtricitabine and tenofovir alafenamide under fasted conditions.

| PK Parameter | Mean (% CV) Compound of Formula I/ F/TAF (75/200/25 mg) (Test) (N = 28) | Compound of Formula I (75 mg) + F/TAF (200/25 mg) (Reference) (N = 28) | % GLSM Ratio (90% CI) |
|---|---|---|---|
| Compound of Formula I | | | |
| $AUC_{last}$ (h · ng/mL) | 151,844.0 (26.9) | 119,619.4 (26.6) | 126.76 (117.82, 136.37) |
| $AUC_{inf}$ (h · ng/mL) | 156,637.5 (27.5) | 123,174.0 (26.6) | 126.82 (117.87, 136.45) |
| $C_{max}$ (ng/mL) | 7123.9 (21.6) | 5593.9 (31.0) | 130.72 (119.95, 142.45) |
| FTC | | | |
| $AUC_{last}$ (h · ng/mL) | 11,412.3 (13.5) | 11,199.3 (13.7) | 101.89 (99.50, 104.33) |
| $AUC_{inf}$ (h · ng/mL) | 11,642.8 (13.2) | 11,436.4 (13.2) | 101.78 (99.45, 104.16) |
| $C_{max}$ (ng/mL) | 2264.3 (22.7) | 2153.6 (21.5) | 104.86 (97.73, 112.50) |
| TAF | | | |
| $AUC_{last}$ (h · ng/mL) | 205.5 (45.5) | 223.6 (45.2) | 91.62 (82.13, 102.21) |
| $AUC_{inf}$ (h · ng/mL) | 206.8 (45.2) | 225.1 (45.0) | 91.56 (82.27, 101.91) |
| $C_{max}$ (ng/mL) | 253.3 (44.2) | 276.7 (51.7) | 95.47 (79.88, 114.10) |

The total exposure of the compound of Formula I, under fasted conditions, was approximately 30% higher when dosed in the bilayer tablet formulation F2, containing two additional therapeutic agents (TAF and FTC), compared to single agent tablet formulation F1, co-dosed with a fixed dose combination tablet containing TAF and FTC (F3). Under fasted conditions, the $AUC_{inf}$ and $C_{max}$ of the compound of Formula I were 27% and 31% higher, respectively, following administration of bilayer tablet formulation F2 than following administration of single-agent tablet formulation F1 with the F/TAF fixed dose combination (F3, 200/25 mg). Emtricitabine and tenofovir alafenamide exposure was similar following administration of bilayer tablet formulation F2 or single-agent tablet formulation F1 with the F/TAF FDC (F3, 200/25 mg).

Based on the data from this study, a new fixed dose formulation of the compound of Formula I, emtricitabine, and tenofovir alafenamide was developed.

The effect of food on the pharmacokinetics of the compound of Formula I was also examined in a non-randomized, open label, crossover, 2 period, fixed sequence, and single dose cohort consisting of 8 unique subjects. In this study, a single dose of the compound of Formula I was administered in two periods with fixed sequence under fasted and fed conditions respectively. A washout of at least five half-lives was required between fasted and fed sequences.

The compound of Formula I was prepared according to percent weight of the tablet formulation of Example 1, a dose equivalent to 100 mg of the compound of Formula I and excipient amounts adjusted accordingly to arrive at the designated weight percentages (100 mg/tablet). A single tablet containing the compound of Formula I (100 mg/tablet) was administered with approximately 240 mL water after an overnight fast (no food or drink, except water, for at least 10 hours) on Day 1. Subjects continued to fast until 4 hours post dose or until collection of the 4-hour postdose blood sample. On Day 9, A single tablet containing the compound of Formula I (100 mg/tablet) was administered with approximately 240 mL water after an overnight fast (no food or drink, except water, for at least 10 hours) and within 5 minutes of the subjects finishing a standard high-fat breakfast (approximately 800 calories with 50% of calories from fat).

The evaluation of the effect of food on compound of Formula I was obtained by comparing $AUC_{inf}$, $AUC_{0\text{-}last}$, and $C_{max}$ on Days 1 and 9 under fed and fasted conditions. The natural log-transformed PK parameters (i.e. $AUC_{inf}$, $AUC_{0\text{-}last}$, and $C_{max}$) were evaluated using a mixed-effects model with food as a fixed effect and subject as a random effect. The 90% CI for the geometric least square mean (GLSM) ratios for fast versus fed was constructed. The statistical comparison of the pharmacokinetic parameters of the compound of Formula I following single dose administration of this tablet formulation in fed and fasted states is presented in the table below.

| Compound of Formula I PK Parameter | Mean (% CV) Test Compound of Formula I 100 mg Fed (n = 8) | Reference Compound of Formula I 100 mg Fasted (n = 8) | % GLSM Ratio (90% CI) |
|---|---|---|---|
| $AUC_{inf}$ (hr*ng/mL) | 214,146.3 (15.9) | 117,777.1 (23.3) | 183.97 (152.05, 222.59) |
| $AUC_{last}$ (hr*ng/mL) | 209,259.9 (15.1) | 115,681.7 (24.0) | 183.58 (151.91, 221.86) |
| $C_{max}$ (ng/mL) | 11,268.8 (15.1) | 5885.0 (34.9) | 200.69 (165.93, 242.74) |

The Table above presents the GLSM ratios and associated 90% confidence intervals (CIs) for the test (fed) versus reference (fasted) treatments for the primary plasma PK parameters of the compound of Formula I. Administration of a single dose of the compound of Formula I 100 mg with food (high-calorie/high-fat breakfast) increased the GLSM values of $C_{max}$ and $AUC_{inf}$ 101% (90% CI of GLSM ratio 165.93% to 242.74%) and 84% (90% CI of GLSM ratio 152.05% to 222.59%), respectively. There were no apparent changes in clearance and $t_{1/2}$ following administration with food, indicating that food enhanced the bioavailability of the compound of Formula I by improving its solubility and/or absorption.

The effect of food on the PK of the compound of formula I, emtricitabine, and tenofovir alafenamide when administered as the tablet formulation F2 tablet was evaluated in the clinical study described above (The randomized, open-label, multiple-period, fixed-sequence, crossover study involving 28 subjects comparing bilayer tablet formulation F2 with that of single agent tablet formulation F1 co-administered simultaneously with a fixed-dose combination tablet containing emtricitabine and tenofovir alafenamide (tablet formulation F3).

The mean (% CV) values, GLSM ratios, and 90% Cl values of the plasma for PK parameters $AUC_{last}$, $AUC_{inf}$, and $C_{max}$ for the compound of Formula I, emtricitabine, and tenofovir alafenamide following administration of tablet formulation F1 under fasted conditions or with a high-fat meal are presented in the following table.

| PK Parameter | Mean (% CV) Compound of Formula I/F/TAF (75/200/25 mg) (High-Fat Meal; Test) (N = 28) | Mean (% CV) Compound of Formula I/F/TAF (75/200/25 mg) (Fasted; Reference) (N = 28) | % GLSM Ratio (90% CI) |
|---|---|---|---|
| Compound of Formula I | | | |
| $AUC_{last}$ (h · ng/mL) | 216,733.1 (23.4) | 151,844.0 (26.9) | 144.45 (134.26, 155.40) |
| $AUC_{inf}$ (h · ng/mL) | 226,142.1 (24.9) | 156,637.5 (27.5) | 145.88 (135.58, 156.95) |
| $C_{max}$ (ng/mL) | 8941.1 (16.9) | 7123.9 (21.6) | 126.74 (116.30, 138.12) |
| FTC | | | |
| $AUC_{last}$ (h · ng/mL) | 11,483.0 (15.7) | 11,412.3 (13.5) | 100.34 (97.99, 102.75) |
| $AUC_{inf}$ (h · ng/mL) | 11,706.4 (15.6) | 11,641.6 (13.2) | 100.25 (97.96, 102.59) |
| $C_{max}$ (ng/mL) | 1872.5 (20.1) | 2264.3 (22.7) | 83.18 (77.53, 89.25) |
| TAF | | | |
| $AUC_{last}$ (h · ng/mL) | 315.3 (44.0) | 205.5 (45.5) | 156.81 (140.57, 174.94) |
| $AUC_{inf}$ (h · ng/mL) | 319.7 (43.1) | 206.8 (45.2) | 158.20 (142.14, 176.08) |
| $C_{max}$ (ng/mL) | 212.2 (49.4) | 253.3 (44.2) | 83.22 (69.63, 99.46) |

Compared with administration under fasted conditions, administration of the tablet formulation F2 with a high-fat meal resulted in a 46% higher $AUC_{inf}$ and a 27% higher $C_{max}$ for the compound of Formula I. The impact of food on emtricitabine and tenofovir alafenamide exposure was similar to that previously observed.

The data presented in the two tables above also demonstrate that the effect of food on the total exposure of the compound of Formula I is reduced in bilayer tablet formulation F2, relative to the single agent tablet formulation F1. The geometric mean ratio of $AUC_{inf}$ for the compound of Formula I in single agent tablet formulation F1 was 1.84, while the geometric mean ratio of $AUC_{inf}$ for the compound of Formula I in bilayer tablet formulation F2 was 1.46. In comparison the geometric mean ratio of $AUC_{inf}$ for emtricitabine in to 0.91 and 1.00 for emtricitabine and 1.75 and 1.58 for tenofovir alafenamide in each formulation respectively (comparing the emtricitabine and tenofovir alafenamide exposures of the tablet formulation F2 with that of tablet formulation F1 codosed with the tablet formulation F3). The geometric mean ratio of $C_{max}$ for single agent tablet formulation F1 was 2.01, while the geometric mean ratio of $C_{max}$ for bilayer tablet formulation F2 was 1.27. In comparison, the geometric mean ratios of $C_{max}$ for emtricitabine and tenofovir alafenamide in tablet formulations F1 and F2 were 0.85 and 0.83, respectively. These data indicate that a fixed dosed combination tablet formulation of the compound of Formula I, emtricitabine, and tenofovir alafenamide may be taken without regard to food.

Example 4—Dissolution Studies

Studies were carried out to assess the dissolution profiles of tablets F1, F2, and F3-A. Dissolution of the compound of Formula II was measured using USP Apparatus II, in 250 ml of pH 6.5 fasted state simulated intestinal fluid (FaSSIF), at 37° C., and paddle speed of 100 rpm. FaSSIF was prepared by adding simulated intestinal fluid (SIF) powder (Biorelevant.com) to pH 6.5 phosphate buffer at approximately 4.48 g/L. Once the powder was dissolved, the volume of the resulting solution was doubled. In the case of the single agent tablet formulation F1, dissolution of the compound of Formula II was measured in the presence of the fixed dose combination tablet formulation F3 of Example 2A containing emtricitabine and tenofovir alafenamide hemifumarate. The results are shown in FIG. 1. These data show that the bilayer formulation (tablet F2) exhibited enhanced dissolution of the compound of Formula II, compared to the single agent formulation (tablet F1 codosed with F3). Tablet formulation F3-A was prepared as a single agent formulation according to the process described in Example 1 according to the table below.

| Ingredient | Tablet F3-A (mg/tablet) Compound of Formula II Layer |
|---|---|
| Compound of Formula II | 78.7* |
| Emtricitabine | |
| Tenofovir alafenamide hemifumarate | |

-continued

| Ingredient | Tablet F3-A (mg/tablet) Compound of Formula II Layer |
|---|---|
| Microcrystalline cellulose | 247.8*** |
| Croscarmellose sodium | 21.2 |
| Magnesium Stearate | 5.3† |
| Tablet Core Weight | 353 |

*Equivalent to 75 mg of the Compound of Formula I

***Intergranular: 212.5 mg (29.1%); Extragranular: 2.65 mg (0.4%)

†Intergranular: 2.65 mg (0.4%); Extragranular: 2.65 mg (0.4%)

As shown above, Tablet F3-A used the composition (excipient selection and quantities) of the Compound of Formula II Layer of Example 2 (F2). FIG. 1 further demonstrates that Tablet formulation F2 exhibited enhanced dissolution of the compound of Formula II compared to Tablet formulations F1 and F3-A. The total percentage of the compound of Formula II dissolved from formulation F1 and F3-A was comparable at approximately 60%. The total amount of the compound of Formula II dissolved from formulation F2 was approximately 10% higher.

Figure 2:
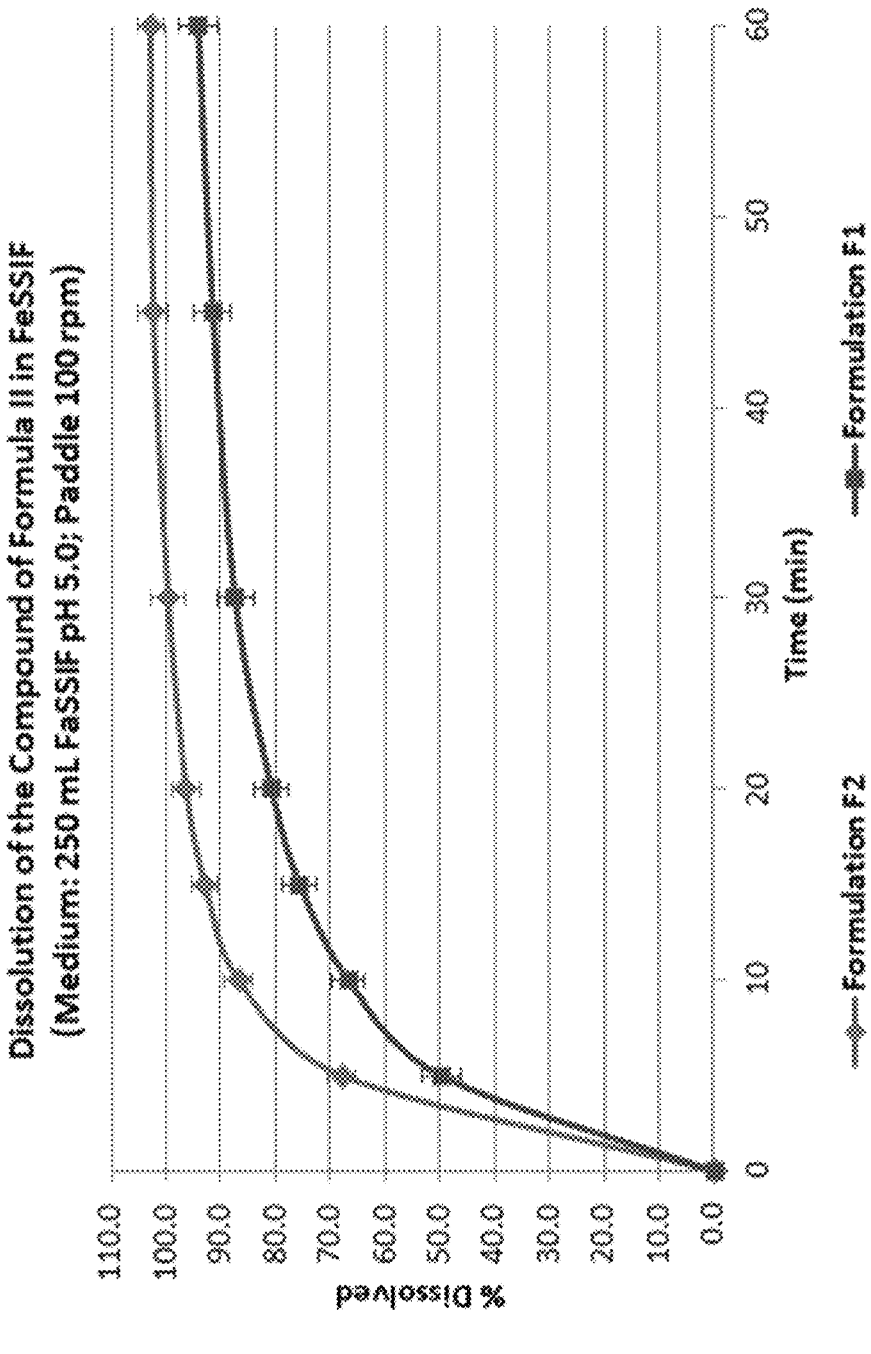
FIG. 2 shows the results of studies carried out on Formulations F1 and F2 to assess the dissolution of 78 mg of the Compound of Formula II as a single agent compared to a bi-layer using fed simulated intestinal fluid as a dissolution medium.

In a second study, dissolution of the compound of Formula II was measured using fed state simulated intestinal fluid (FeSSIF) as dissolution medium. FeSSIF was prepared by adding simulated intestinal fluid (SIF) powder (Biorelevant.com) to pH 5.0 phosphate buffer at approximately 22.405 g/L. Once the power was dissolved, the volume of the resulting solution was doubled. In this study, dissolution of the compound of Formula II was measured using USP Apparatus II, in 250 mL of pH 5.5 fed simulated intestinal fluid, at 37° C., and paddle speed of 100 rpm. As in the previous study using fasted simulated intestinal fluid, the single agent tablet formulation F1 was tested in the presence of a second tablet formulation containing emtricitabine and tenofovir alafenamide hemifumarate (tablet F3). The results are shown in FIG. 2. These data also show that the bilayer formulation (tablet F2) exhibited enhanced dissolution of the compound of Formula II, compared to the single agent formulation (tablet F1).

Example 5—Excipient Studies

To further assess the effect of specific excipients on dissolution of the compound of Formula I, three additional bilayer tablet formulations were prepared, F4, F5, and F6. Tablet formulation F4 is similar to tablet formulation F2, with croscarmellose sodium being replaced with crospovidone. Likewise, tablet formulation F5 is similar to tablet formulation F2, with magnesium stearate being replaced with sodium stearyl fumarate. Finally, tablet formulation F6 is similar to tablet formulation F2, with both croscarmellose sodium and magnesium stearate being replaced with crospovidone and sodium stearyl fumarate, respectively. Tablets F4, F5, and F6 were prepared using the method described in Example 8.

| Ingredient | Emtricitabine/ tenofovir alafenamide hemifumarate Layer (mg/tablet) | Bilayer tablet F4 | Bilayer tablet F5 | Bilayer tablet F6 |
|---|---|---|---|---|
| | | Compound of Formula I Layer (mg/tablet) | | |
| Emtricitabine | 200 | | | |
| Tenofovir alafenamide hemifumarate | 28.1 | | | |
| Compound of Formula II | | 78.7 | 78.7 | 78.7 |
| Microcrystalline cellulose | 113 | 244 | 248 | 244 |
| Croscarmellose sodium | 30.2 | | 21.2 | |
| Crospovidone | | 24.7 | | 24.7 |
| Magnesium Stearate | 5.7 | 5.3 | | |
| Sodium Stearyl Fumarate | | | 5.3 | 5.3 |
| Layer Weight | 377 | 353 | 353 | 353 |
| Tablet Core Weight | | 730 | 730 | 730 |

Figure 3:
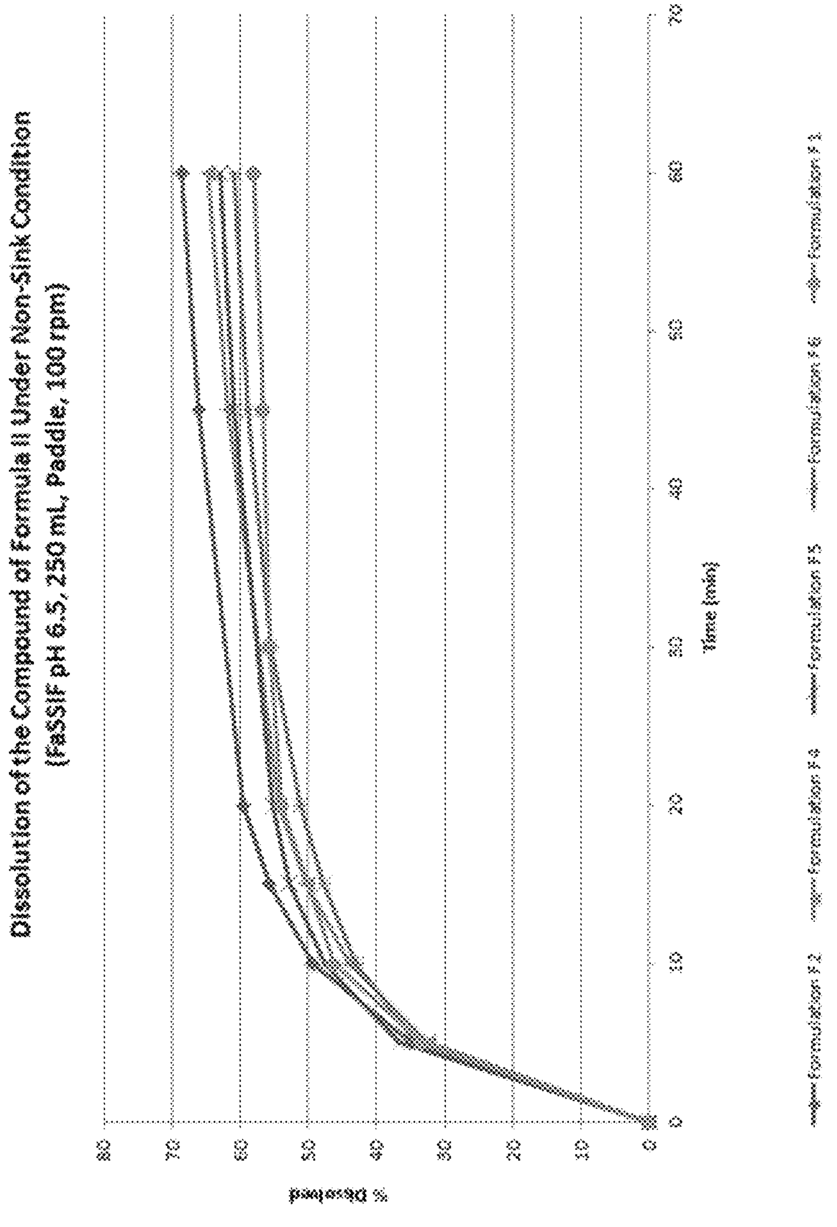
FIG. 3 shows the results of studies carried out on Formulations F1, F2, F4, F5, and F6 to assess the dissolution of 78 mg of the Compound of Formula II in tablets containing various excipients.

FIG. 3 shows the results of dissolution studies performed on tablet formulations F4, F5, and F6, as well as tablet formulation F1 and F2. These data demonstrate that the substitution of each excipient enhances the dissolution of the compound of Formula I.

Example 6—Compound of Formula I/Emtricitabine/Tenofovir Alafenamide Bilayer Tablets-50 mg Dose As a result of the higher in vivo exposure of the compound of Formula I that was observed in the pharmacokinetic studies, a bilayer formulation (tablet F7) of the compound of Formula II, emtricitabine, and tenofovir alafenamide hemifumarate was prepared incorporating a lower dose of the compound of Formula I. Tablet formulation F7 was prepared as described previously, i.e. using the method described in Example 8. The composition of the formulation is summarized in the table below:

| Ingredient | Bilayer tablet F7 (mg/tablet) Compound of Formula II Layer | Emtricitabine/ tenofovir alafenamide hemifumarate Layer |
|---|---|---|
| Compound of Formula II | 52.5* | |
| Emtricitabine | | 200 |
| Tenofovir alafenamide hemifumarate | | 28** |
| Microcrystalline cellulose | 246.3 | 113.2 |
| Croscarmellose sodium | 19.4 | 30.2 |
| Magnesium Stearate | 4.9 | 5.7 |
| Layer Weight | 323 | 377 |
| Tablet Core Weight | 700 | |
| Opadry II Brown 85F165072 | 21 | |
| Film Coated Tablet | 721 | |

*Equivalent to 50 mg of the Compound of Formula I

**Equivalent to 25 mg tenofovir alafenamide

Example 7—Compound of Formula I Single Agent Tablets (50 mg)

Dissolution studies were performed comparing the 50 mg dose bilayer tablet F7 with a 50 mg single agent tablet.

A 50 mg formulation (tablet F8) of the compound of Formula II was prepared in a similar manner as tablet formulation F1 of Example 1. The composition of the single agent formulation is shown in the table below:

| | Tablet Formulation F8 | |
|---|---|---|
| Component | Mass (mg/tablet) | % w/w/tablet |
| Compound of Formula II | 52.5 | 26.2 |
| Microcrystalline cellulose | 80 | 40 |
| Lactose | 50.5 | 25.3 |
| Crospovidone | 14 | 7 |
| Sodium Stearyl Fumarate | 3 | 1.5 |
| Total Weight | 200 | |

Figure 4:
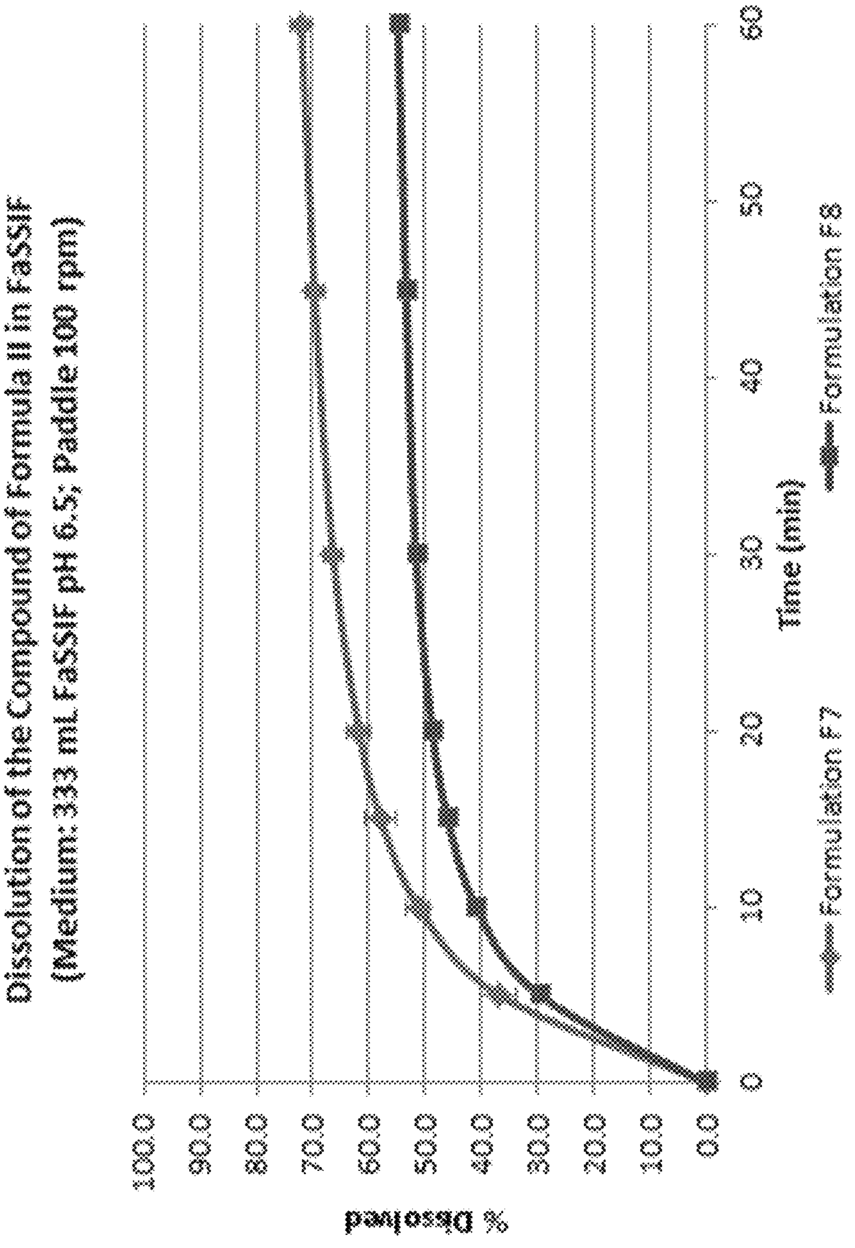
FIG. 4 shows the results of studies carried out on Formulations F7 and F8 to assess the dissolution of 52 mg of the Compound of Formula II as a single agent compared to a bi-layer using fasted simulated intestinal fluid as a dissolution medium.

FIG. 4 shows the dissolution of 50 mg bilayer tablet formulation (fixed dose combination) F7 and 50 mg single agent tablet formulation F8. Dissolution of the compound of Formula II was measured using USP Apparatus II, in 333 mL of pH 6.5 FaSSIF, at 37° C., and paddle speed of 100 rpm. Two tablets of each tablet formulation, F7 and F8 were tested. As in Example 3, in the case of the single agent tablet formulation F8, dissolution of the compound of Formula II was measured in the presence of the fixed dose combination tablet formulation of Example 2A containing emtricitabine and tenofovir alafenamide hemifumarate. These data show that the 50 mg bilayer formulation (tablet F7) exhibited enhanced dissolution of the compound of Formula II, compared to the single agent formulation (tablet F8).

Example 8—Manufacturing Process

The manufacturing/packaging procedure for the compound of Formula II/emtricitabine/tenofovir alafenamide hemifumarate tablets is divided into five unit processes:

1, mixing of the compound of Formula II drug substance with intergranular excipients, roller compaction or slugging, milling, and blending with extragranular excipients to yield the final powder blend for the compound of Formula II;

2, mixing of emtricitabine and tenofovir alafenamide hemifumarate drug substances with intergranular excipients, dry granulation, milling, and blending with extragranular excipients to yield emtricitabine/tenofovir alafenamide hemifumarate final powder blend;

3, tablet compression to yield bilayer tablet cores;

4, tablet film-coating to yield film-coated tablets; and 5, packaging.

The manufacturing process steps to produce the final drug product are detailed below.

Final Powder Blend for the Compound of Formula II (Dispensing, Blending, Dry Granulation, Milling, Final Blending)

1. Weigh the compound of Formula II and the excipients (microcrystalline cellulose and croscarmellose sodium). Correct the weight of the compound of Formula II based on the drug content factor (DCF), with a concomitant reduction in the weight of microcrystalline cellulose.
2. Blend in intergranular portion of magnesium stearate to the tumble blender and blend.
3. Dry granulate the resulting blend using a roller compactor or slug the resulting blend and mill.
4. Add extragranular microcrystalline cellulose and magnesium stearate and blend.

Emtricitabine/tenofovir alafenamide hemifumarate Final Powder Blend (Dispensing, Blending, Dry Granulation, Milling, Final Blending)

5. Weigh emtricitabine and tenofovir alafenamide hemifumarate drug substances and excipients (microcrystalline cellulose and croscarmellose sodium). Adjust the weight of emtricitabine and tenofovir alafenamide hemifumarate drug substances based on their corresponding DCF, with a concomitant adjustment to the weight of microcrystalline cellulose.

6. Blend in emtricitabine and tenofovir alafenamide hemifumarate drug substance, microcrystalline cellulose, and croscarmellose sodium to a tumble blender and blend.
7. Blend in intergranular portion of magnesium stearate to the tumble blender and blend.
8. Dry granulate the resulting blend using a roller compactor or slug the resulting blend and mill.
9. Blend in the extragranular portion of magnesium stearate.

Tableting

10. Compress the final powder blend of the compound of Formula II as the first layer and the emtricitabine/tenofovir alafenamide hemifumarate final powder blend as the second layer, with an appropriate main compression force to achieve a target hardness of 17 kP (range: 14 to 20 KP). For tablet formulations containing 50 mg of the compound of Formula II, the final powder blend is compressed to a target layer weight of 323 mg using a target total tablet weight of 700 mg. For tablet formulations containing 75 mg of the compound of Formula II, the final powder blend is compressed to a target layer weight of 353 mg using a target total tablet weight of 730 mg.

Film-Coating

11. Prepare a suspension of Opadry® II Brown 85F165072 (for tablets containing 50 mg compound of Formula I) or Opadry® II Yellow 85F92259 (for tablets containing 75 mg compound of Formula I). Film-coat the tablet cores to achieve the target tablet weight gain of 3% (range 2-4%). Dry film-coated tablets prior to cooling and discharge.

Example 9—Pharmacokinetic Studies—Cohort 2

The pharmacokinetic study of Example 3 was continued with a second treatment group (cohort) to assess the pharmacokinetic profile of formulation F7 of Example 7 compared with that of formulation F2.

Study Design and Duration of Treatment

Four single doses of the following tablet formulations were administered once per day orally during 36 days total study duration:

(a) a fixed dosed combination tablet containing emtricitabine and tenofovir alafenamide (200/25 mg—Tablet F3) and a single agent tablet containing the compound of Formula I (75 mg—Tablet F1) administered simultaneously, under fasted conditions (Treatment A) (dosed on day 1; days 2-8 washout);

(b) a fixed dose combination tablet containing the compound of Formula I, emtricitabine, and tenofovir alafenamide (50/200/25 mg—Tablet F2) administered under fasted conditions (Treatment D) (dosed on day 9; days 10-16 washout); and (b) a fixed dose combination tablet containing the compound of Formula I, emtricitabine, and tenofovir alafenamide (50/200/25 mg—Tablet F2) administered under fed conditions with a high-fat meal (Treatment E) (dosed on day 17; days 18-24 washout);

(c) a fixed dose combination tablet containing the compound of Formula I, emtricitabine, and tenofovir alafenamide (50/200/25 mg—Tablet F2) administered under fed conditions with a moderate-fat meal (Treatment F) (dosed on day 25; day 29 discharge).

Criteria for Evaluation

The following plasma pharmacokinetic parameters were calculated: $AUC_{last}$, $AUC_{inf}$, % $AUC_{exp}$, $C_{max}$, $C_{last}$, $T_{max}$, $T_{last}$, CL/F, $V_z$/F, and $t_{1/2}$.

Statistical Methods

Pharmacokinetics: Individual subject concentration data and individual subject PK parameters for each analyte (compound of Formula I, FTC, and TAF) were listed and summarized using descriptive statistics by treatment group (cohort) and treatment. Summary statistics were determined for both individual subject concentration data by time point, cohort, and treatment and individual subject PK parameters by cohort and treatment. Also, the geometric mean, 95% confidence interval (CI), and the mean, and standard deviation (SD) of the natural log-transformed values were presented for individual subject PK parameter data. The sample size for each time point was based on the number of subjects with nonmissing concentration data at that time point. The number of subjects with concentration below the level of quantitation (BLQ) was presented for each time point.

Statistical comparisons of the natural log-transformed PK parameters for each analyte and treatment comparison of interest were performed. The statistical modelling was based on the PK Analysis set for the analyte under evaluation. For each analyte, all subjects with available data for the PK parameter under evaluation were included in the modelling. The statistical comparisons using Treatment A as a reference only used data from this cohort, not from the earlier cohort of Example 3 (i.e. Treatment A was not pooled).

For each analyte and each PK parameter, a parametric (normal theory) mixed-effects ANOVA model was fitted to the natural log-transformed values of the PK parameter under evaluation. The statistical model included treatment as a fixed effect and subject as a random effect.

A total of 27 subjects completed the second treatment group of the study.

Results

Plasma pharmacokinetic parameters for each analyte are presented below. This table presents the mean (% CV) values, Geometric Least Squares Mean (GLSM) ratios, and 90% CI values of the plasma PK parameters $AUC_{last}$, $AUC_{inf}$, and $C_{max}$ for each active ingredient, following administration of bilayer tablet formulation F7 and monolayer tablet formulation F1 coadministered with F/TAF formulation F3, under fasted conditions.

| | Mean (% CV) | | |
|---|---|---|---|
| | Formulation F7 Compound of Formula I/F/TAF (50/200/25 mg), fasted (Test) (N = 27) | Formulation F1 + F3 Compound of Formula (75 mg) + F/TAF (200/25 mg)), fasted (Reference) (N = 28) | % GLSM Ratio (90% CI) (Test/Reference) |
| Compound of Formula I PK Parameter | | | |
| $AUC_{last}$ (hr · ng/mL) | 109,061.4 (21.0) | 142,396.6 (30.5) | 78.46 (73.38, 83.89) |
| $AUC_{inf}$ (hr · ng/mL) | 112,619.6 (21.9) | 146,931.6 (31.1) | 78.56 (73.44, 84.04) |
| $C_{max}$ (ng/mL) | 5228.1 (16.9) | 6791.1 (26.4) | 78.07 (73.41, 83.01) |
| FTC PK Parameter | | | |
| $AUC_{last}$ (hr · ng/mL) | 10,652.9 (13.6) | 11,035.5 (14.4) | 96.52 (93.95, 99.15) |
| $AUC_{inf}$ (hr · ng/mL) | 10,873.9 (13.6) | 11,234.6 (14.2) | 96.76 (94.22, 99.37) |
| $C_{max}$ (ng/mL) | 2220.4 (30.1) | 2166.4 (27.0) | 102.36 (93.85, 111.64) |
| TAF PK Parameter[a] | | | |
| $AUC_{last}$ (hr · ng/mL) | 207.1 (46.5) | 236.7 (45.3) | 85.37 (75.24, 96.85) |
| $AUC_{inf}$ (hr · ng/mL) | 208.8 (46.3) | 238.3 (45.0) | 85.48 (75.33, 97.00) |
| $C_{max}$ (ng/mL) | 249.2 (51.6) | 291.9 (55.4) | 84.17 (67.59, 104.81) |

In particular, these data confirmed that the exposure of the compound of Formula I in Formulation F7 was proportionally lower than that observed in Formulation F2 and were consistent with predicted exposures for the revised dose. These data were consistent with the modelling of earlier clinical data confirming that these exposures provided anti-HIV antiviral efficacy. FTC and TAF exposure were similar between Formulation F7 and Formulation F2 coadministered with F3; TAF $C_{max}$ was slightly lower (by approximately 16%) for Formulation F7 than for the coadministration of F2 and F3.

The effect of food on the pharmacokinetics of the compound of Formula I, emtricitabine and tenofovir alafenamide when administered in formulation F7 was also examined in a further treatment group of the above described clinical study.

The mean (% CV) values, GLSM ratios, and 90% CI values of the plasma for PK parameters $AUC_{last}$, $AUC_{inf}$, and $C_{max}$ for the compound of Formula I, emtricitabine, and tenofovir alafenamide following administration of tablet formulation F7 under fasted conditions or with a high-fat meal and with a moderate-fat meal are presented in the following table.

| | Mean (% CV) | | |
|---|---|---|---|
| | Compound of Formula I/F/TAF (50/200/25 mg) high fat meal (Test) (N = 27) | Compound of Formula I/F/TAF (50/200/25 mg) fasted (Reference) (N = 27) | % GLSM Ratio (90% CI) (Test/Reference) |
| Compound of Formula I PK Parameter | | | |
| $AUC_{last}$ (hr · ng/mL) | 135,117.3 (21.1) | 109,061.4 (21.0) | 123.96 (115.91, 132.57) |
| $AUC_{inf}$ (hr · ng/mL) | 140,032.4 (21.8) | 112,619.6 (21.9) | 124.41 (116.27, 133.11) |
| $C_{max}$ (ng/mL) | 5936.3 (18.3) | 5228.1 (16.9) | 113.23 (106.45, 120.43) |
| FTC PK Parameter | | | |
| $AUC_{last}$ (hr · ng/mL) | 10,213.0 (12.0) | 10,652.9 (13.6) | 96.02 (93.47, 98.65) |
| $AUC_{inf}$ (hr · ng/mL) | 10,467.0 (11.9) | 10,873.9 (13.6) | 96.41 (93.88, 99.02) |
| $C_{max}$ (ng/mL) | 1881.1 (24.2) | 2220.4 (30.1) | 85.52 (78.37, 93.31) |
| TAF PK Parameter[a] | | | |
| $AUC_{last}$ (hr · ng/mL) | 310.3 (34.9) | 207.1 (46.5) | 162.62 (143.10, 184.80) |
| $AUC_{inf}$ (hr · ng/mL) | 318.4 (32.8) | 208.8 (46.3) | 166.55 (146.54, 189.29) |
| $C_{max}$ (ng/mL) | 236.6 (65.1) | 249.2 (51.6) | 91.71 (73.46, 114.49) |

| | Mean (% CV) | | |
|---|---|---|---|
| | Compound of Formula I/F/TAF (50/200/25 mg) moderate fat meal (Test) (N = 27) | Compound of Formula I/F/TAF (50/200/25 mg) fasted (Reference) (N = 27) | % GLSM Ratio (90% CI) (Test/Reference) |
| Compound of Formula I PK Parameter | | | |
| $AUC_{last}$ (hr · ng/mL) | 135,217.3 (22.9) | 109,061.4 (21.0) | 123.56 (115.53, 132.14) |
| $AUC_{inf}$ (hr · ng/mL) | 140,197.7 (23.6) | 112,619.6 (21.9) | 124.06 (115.95, 132.74) |
| $C_{max}$ (ng/mL) | 6279.6 (18.3) | 5228.1 (16.9) | 119.90 (112.72, 127.53) |
| FTC PK Parameter | | | |
| $AUC_{last}$ (hr · ng/mL) | 10,738.3 (9.8) | 10,652.9 (13.6) | 101.17 (98.48, 103.94) |
| $AUC_{inf}$ (hr · ng/mL) | 10,973.3 (9.5) | 10,873.9 (13.6) | 101.33 (98.66, 104.06) |
| $C_{max}$ (ng/mL) | 1998.9 (18.4) | 2220.4 (30.1) | 91.84 (84.17, 100.21) |
| TAF PK Parameter[a] | | | |
| $AUC_{last}$ (hr · ng/mL) | 290.6 (41.3) | 207.1 (46.5) | 148.20 (130.41, 168.41) |
| $AUC_{inf}$ (hr · ng/mL) | 293.1 (40.9) | 208.8 (46.3) | 148.23 (130.42, 168.47) |
| $C_{max}$ (ng/mL) | 251.1 (66.7) | 249.2 (51.6) | 99.04 (79.33, 123.65) |

[a]N = 28 for the Reference group

Compared with administration under fasted conditions, administration of the tablet formulation F7 with a high-fat meal resulted in a 24% higher AUCH, and a 13% higher $C_{max}$ for the compound of Formula I. Administration of a moderate fat meal, resulted in a 24% higher AUCH and a 20% higher $C_{max}$ for the compound of Formula I. The impact of food on emtricitabine and tenofovir alafenamide exposure was similar to that previously observed.

These data confirm that a fixed dosed combination tablet formulation of the compound of Formula I, emtricitabine, and tenofovir alafenamide may be taken without regard to food.

Example 10—Compression Studies

To further investigate the properties of the compositions, the following studies investigated blend compressibility and layer adhesion.

First, various final blend compositions including the Compound of Formula I (as a sodium salt, i.e. the Compound of Formula II) were prepared with varying levels of intergranular or extragranular lactose is shown in the table below.

Compound of Formula II: Final Powder Blends Containing Lactose

| | Tablet Formulation | | | | | |
|---|---|---|---|---|---|---|
| Components | F9 | F10 | F11 | F12 | F13 | F14 |
| Intergranular % w/w | | | | | | |
| Compound of Formula II | 16.24 | 16.24 | 16.24 | 16.24 | 14.86 | 14.86 |
| Microcrystalline Cellulose | 46.25 | 56.25 | 56.25 | 56.25 | 69.12 | 60.63 |
| Lactose | 20.00 | NA | NA | NA | 0.00 | 8.50 |

-continued

| Compound of Formula II: Final Powder Blends Containing Lactose | | | | | | |
|---|---|---|---|---|---|---|
| | Tablet Formulation | | | | | |
| Components | F9 | F10 | F11 | F12 | F13 | F14 |
| Croscarmellose Sodium | 6.00 | 6.00 | 6.00 | 6.00 | 5.49 | 5.49 |
| Magnesium Stearate | 0.75 | 0.75 | 0.75 | 0.75 | 0.69 | 0.69 |
| Extragranular % w/w | | | | | | |
| Microcrystalline Cellulose | 10.00 | 10.00 | 5.00 | 15.00 | 9.15 | 9.15 |
| Lactose | NA | 10.00 | 15.00 | 5.00 | NA | NA |
| Magnesium Stearate | 0.75 | 0.75 | 0.75 | 0.75 | 0.69 | 0.69 |
| Layer weight (mg) | 323 | 323 | 323 | 323 | 353 | 353 |

Next, final blend compositions of the Compound of Formula II with varying amounts of magnesium stearate ranging from 0.75% to 0.5% were prepared as shown on the following table:

| Compound of Formula I: Final Powder Blends with Varying Levels of Magnesium Stearate | | | | | | |
|---|---|---|---|---|---|---|
| | Tablet Formulation | | | | | |
| Components | F15 | F16 | F17 | F18 | F19 | F20 |
| Intergranular % w/w | | | | | | |
| Compound of Formula II | 16.24 | 16.24 | 16.24 | 16.24 | 16.24 | 16.24 |
| Microcrystalline Cellulose | 66.25 | 66.30 | 66.40 | 66.40 | 66.50 | 66.75 |
| Croscarmellose Sodium | 6.00 | 6.00 | 6.00 | 6.00 | 6.00 | 6.00 |
| Magnesium Stearate | 0.75 | 0.70 | 0.60 | 0.60 | 0.50 | 0.50 |
| Extragranular % w/w | | | | | | |
| Microcrystalline Cellulose | 10.00 | 10.00 | 10.00 | 10.00 | 10.00 | 10.00 |
| Magnesium Stearate | 0.75 | 0.75 | 0.75 | 0.75 | 0.75 | 0.5 |
| Layer weight (mg) | 323 | 323 | 323 | 323 | 323 | 323 |

Finally, final blend compositions containing emtricitabine and tenofovir alafenamide were prepared with varying amounts of magnesium stearate ranging from 0.75% to 0.5% as shown in the table below:

| Quantitative Compositions of F/TAF Final Powder Blends | | | | |
|---|---|---|---|---|
| | Tablet Formulation | | | |
| Components | F21 | F22 | F23 | F24 |
| Intergranular % w/w | | | | |
| Tenofovir Alafenamide Hemifumarate | 7.5 | 7.5 | 7.5 | 7.5 |
| Emtricitabine | 53.1 | 53.1 | 53.1 | 53.1 |
| Microcrystalline Cellulose | 29.9 | 30.4 | 30 | 30.2 |
| Croscarmellose Sodium | 8.0 | 8.0 | 8.0 | 8.0 |
| Magnesium Stearate | 0.75 | 0.50 | 0.70 | 0.60 |
| Extragranular % w/w | | | | |
| Magnesium Stearate | 0.75 | 0.50 | 0.70 | 0.60 |
| Layer Weight (mg) | 377 | 377 | 377 | 377 |

Altering magnesium stearate content was studied to evaluate the impact on the compound of Formula I and emtricitabine/tenofovir alafenamide blend compressibility and layer adhesion. Formulations were also monitored for punch filming and sticking.

Fourteen combinations of the final powder blends described in the above tables were prepared as summarized in the table below. Critical tamp force was determined for all fourteen combinations.

| Compression Study Critical Layer 1 Tamp Force Results | | | | |
|---|---|---|---|---|
| Formulation Combination | Tablet Formulation Layer 1 | Tablet Formulation Layer 2 | Critical Tamp Force (kN) | Observation |
| A* | F21 | F15 | 1.0 | Layers adhered |
| B* | F21 | F9 | <1.5 | Delamination |
| C* | F21 | F10 | <1.5 | Delamination |
| D* | F21 | F11 | <1.5 | Delamination |
| E* | F21 | F12 | <1.5 | Delamination |
| F* | F21 | F13 | <1.5 | Delamination |
| G* | F21 | F14 | <1.5 | Delamination |
| H | F15 | F21 | 1.5 | Delamination |
| I | F15 | F22 | 2.0 | Layers adhered |
| J | F16 | F23 | 2.0 | Layers adhered |
| K | F17 | F24 | 1.5 | Layers adhered |
| L | F18 | F22 | 2.0 | Layers adhered |
| M | F19 | F22 | 2.5 | Layers adhered, sticking |
| N | F20 | F22 | 2.5 | Layers adhered, sticking |

*Note
F/TAF as layer 1 and Compound of Formula I as layer 2
IG: Intergranular
EG: Extragranular
MgSt Magnesium Stearate Combination A represents layer order and composition used as baseline for comparison of other compositions. The tablet formulation of each layer corresponds to the corresponding layer of tablet formulation F7. One objective was to investigate whether it was possible to improve on the critical tamp force of 1.0 kN observed for Combination A.

Combinations B-G represent studies in which lactose was included in the layer including the Compound of Formula I to investigate evaluate layer adhesion. Combination G included 20% lactose in the intergranular portion, with none in the extragranular portion. The ratio of lactose to microcrystalline cellulose ranged from 1:1, 3:1, 1:3 in Combinations C, D, and E, respectively. Combination G included 20 mg lactose in the intergranular portion. Delamination was observed at 1.5 kN for Combinations B-G. As a result, lower tamp forces were not further investigated. When layer order was reversed (Combination H), delamination did not occur at 1.0 kN but was observed at 1.5 kN using the layer compositions of Combination A.

In Combinations 1-N, varying the amount of magnesium stearate in each layer was investigated to determine the effect on compressibility and layer adhesion. Intergranular magnesium stearate was 0.75%. 0.70% and 0.60% in the Compound of Formula I layer of Combinations I, J, and K, respectively. Total magnesium stearate content in the F/TAF layer of each of Combinations I, J, and K was 1.0%, 1.4% and 1.2% %, respectively. Intergranular magnesium stearate was 0.6% and 0.5% in the Compound of Formula I layer of Combinations L and M, respectively (with 0.75% extragranular magnesium stearate in each). Combination N has the lowest overall level of magnesium stearate in both layers (1.0% in each layer).

It was found that reducing magnesium stearate from 0.75% to 0.5% in each of the intergranular and extragranular portions the emtricitabine/tenofovir alafenamide layer increased critical tamp force to 2.0 kN (combination I). Critical tamp force could be further improved to 2.5 kN when magnesium stearate was reduced to 0.5% extragranular and/or intergranular in the layer containing the Compound of Formula I (combinations M and N). However, despite gaining an increase in critical tamp force, decreasing magnesium stearate to 0.5% in each component of the powder blend containing the Compound of Formula I had a negative effect on sticking. Intermediate changes in magnesium stearate (Combinations J-L) had no further improvement over combination I. As a result, magnesium stearate level was decreased in the emtricitabine/tenofovir alafenamide layer only (formulation combination I). A critical layer 1 tamp force of 1377 N was ultimately determined. The table below summarizes the composition of Formulation I.

Thus, the addition of intergranular or extragranular lactose to the layer containing the Compound of Formula I had little to ono effect on layer adhesion. Decreasing magnesium stearate from each of final powder blends improved compressibility.

Quantitative Composition of Combination Formulation I

| Components | Quantity per Tablet (mg) | w/w (%) |
|---|---|---|
| Compound of Formula I Layer | | |
| Compound of Formula II[a] | 52.5[a, b] | 7.5 |
| Microcrystalline Cellulose | 246.3 | 35.2 |
| Croscarmellose Sodium | 19.4 | 2.8 |
| Magnesium Stearate | 4.9 | 0.7 |
| Subtotal | 323 | 46.1 |

-continued

Quantitative Composition of Combination Formulation I

| Components | Quantity per Tablet (mg) | w/w (%) |
|---|---|---|
| F/TAF Layer | | |
| Emtricitabine[c] | 200.0[c] | 28.6 |
| Tenofovir Alafenamide Fumaratec | 28.0[c, d] | 4.0 |
| Microcrystalline Cellulose | 115.0 | 16.4 |
| Croscarmellose Sodium | 30.2 | 4.3 |
| Magnesium Stearate | 3.8 | 0.5 |
| Subtotal | 377 | 53.9 |
| Total Bilayer Tablet Core Weight | 700 | 100 |
| Opadry II Brown 85F165072[e] | 21[f] | 3[f] |
| Purified Water[g] | —[g] | —[g] |

[a]The quantity used is adjusted on the basis of the purity of each batch of Compound of Formula II with a concomitant adjustment of the quantity of microcrystalline cellulose.

[b] Equivalent to 50 mg of Compound of Formula I free acid.

[c]The quantity used is adjusted on the basis of the purity of each batch of emtricitabine and tenofovir alafenamide hemifumarate with a concomitant adjustment of the quantity of microcrystalline cellulose.

[d] Equivalent to 25 mg of tenofovir alafenamid free base.

[e]Opadry II Brown 85F165072 contains polyvinyl alcohol, USP (40.0% w/w); titanium dioxide, USP (22.0% w/w); polyethylene glycol, NF (20.2% w/w); talc, USP (14.8% w/w); iron oxide red, NF (2.4% w/w); iron oxide black, NF (0.6% w/w).

[f]Represents a theoretical weight gain of 3% w/w (range 2% to 4% w/w) onto the tablet core weight.

[g]Sufficient purified water is used for film coating and is removed during the process All publications, patents and patent applications are incorporated by reference in their entirety, as though individually incorporated by reference. The invention has been described with reference to various specific and preferred embodiments and techniques. However, it should be understood that many variations and modifications may be made while remaining within the spirit and scope of the invention.

The invention claimed is:

1. A tablet comprising from 6.5-11.0% w/w of a compound of Formula I:

Formula I

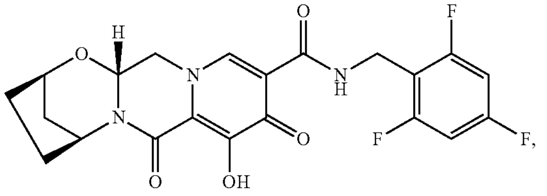

or a pharmaceutically acceptable salt thereof, 3.0-4.5% w/w tenofovir alafenamide or a pharmaceutically acceptable salt thereof, and 25-30% w/w emtricitabine or a pharmaceutically acceptable salt thereof, where the weight percentages denote a proportion of the whole tablet.

2. A tablet comprising from 7.0-11.0% w/w of a compound of Formula II:

Formula II

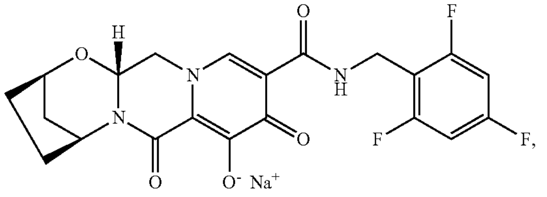

3.5-4.1% w/w tenofovir alafenamide hemifumarate, and 25-30% w/w emtricitabine, where the weight percentages denote a proportion of the whole tablet.

3. The tablet of claim 1, wherein the tablet does not contain lactose, crospovidone, or sodium stearyl fumarate.

4. The tablet of claim 1, wherein the tablet further comprises croscarmellose sodium or magnesium stearate.

5. The tablet of claim 1, wherein the tablet further comprises croscarmellose sodium, magnesium stearate, or microcrystalline cellulose.

6. The tablet of claim 1, wherein the tablet releases at least about 50% of the compound of Formula I or the pharmaceutically acceptable salt thereof in about 20 minutes, measured using USP apparatus II, in 333 mL of fasted simulated intestinal fluid, pH 6.5, at 37° C. and paddle speed of 100 rpm.

7. The tablet of claim 6, wherein the tablet releases at least about 60% of the compound of Formula I or the pharmaceutically acceptable salt thereof in about 20 minutes.

8. The tablet of claim 6, wherein the tablet releases at least about 70% of the compound of Formula I or the pharmaceutically acceptable salt thereof in about 60 minutes.

9. A tablet comprising:

(i) from about 6.4 w/w to about 8.5% w/w of a compound of Formula II

Formula II

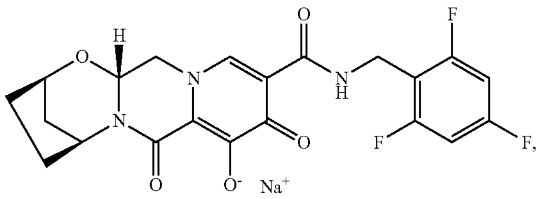

(ii) about 25% w/w to about 32% w/w emtricitabine, (iii) about 3.5% w/w to about 4.5% w/w tenofovir alafenamide hemifumarate, (iv) about 46% w/w to about 57% w/w microcrystalline cellulose, (v) about 5.9% w/w to about 8.5% w/w croscarmellose sodium, and (vi) about 1.0-2.0% w/w magnesium stearate.

10. The tablet of claim 9, further comprising a film coating.

11. The tablet of claim 1, wherein the tablet further comprises croscarmellose sodium and magnesium stearate.

12. The tablet of claim 1, wherein the tablet further comprises croscarmellose sodium, magnesium stearate, and microcrystalline cellulose.

13. The tablet of claim 1, wherein the tablet is a coated tablet.

14. The tablet of claim 1, wherein the tablet has a total weight of between about 250 and about 750 mg.

15. The tablet of claim 2, wherein the tablet does not contain lactose, crospovidone, or sodium stearyl fumarate.

16. The tablet of claim 2, wherein the tablet further comprises croscarmellose sodium or magnesium stearate.

17. The tablet of claim 1, wherein the tablet further comprises croscarmellose sodium and magnesium stearate.

18. The tablet of claim 2, wherein the tablet further comprises croscarmellose sodium, magnesium stearate, or microcrystalline cellulose.

19. The tablet of claim 2, wherein the tablet further comprises croscarmellose sodium, magnesium stearate, and microcrystalline cellulose.

20. The tablet of claim 2, wherein the tablet is a coated tablet.

21. The tablet of claim 2, wherein the tablet has a total weight of between about 250 and about 750 mg.

22. The tablet of claim 2, wherein the tablet releases at least about 50% of the compound of Formula II in about 20 minutes, measured using USP apparatus II, in 333 mL of fasted simulated intestinal fluid, pH 6.5, at 37° C. and paddle speed of 100 rpm.

23. The tablet of claim 22, wherein the tablet releases at least about 60% of the compound of Formula II in about 20 minutes.

24. The tablet of claim 22, wherein the tablet releases at least about 70% of the compound of Formula II in about 60 minutes.

25. The tablet of claim 9, wherein the tablet releases at least about 50% of the compound of Formula II in about 20 minutes, measured using USP apparatus II, in 333 mL of fasted simulated intestinal fluid, pH 6.5, at 37° C. and paddle speed of 100 rpm.

26. The tablet of claim 25, wherein the tablet releases at least about 60% of the compound of Formula II in about 20 minutes.

27. The tablet of claim 25, wherein the tablet releases at least about 70% of the compound of Formula II in about 60 minutes.

28. The tablet of claim 9, wherein the tablet has a total weight of between about 250 and about 750 mg.

29. A method of therapeutic treatment of an HIV infection comprising administering to a subject a tablet comprising:

(i) from about 6.4 w/w to about 8.5% w/w of the compound of Formula II

Formula II

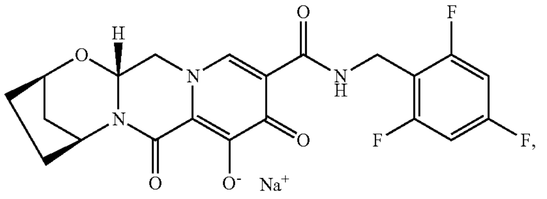

(ii) about 25% w/w to about 32% w/w emtricitabine, (iii) about 3.5% w/w to about 4.5% w/w tenofovir alafenamide hemifumarate, (iv) about 46% w/w to about 57% w/w microcrystalline cellulose, (v) about 5.9% w/w to about 8.5% w/w croscarmellose sodium, and (vi) about 1.0-2.0% w/w magnesium stearate.

* * * * *